(12) United States Patent
Salinas et al.

(10) Patent No.: US 10,632,323 B2
(45) Date of Patent: Apr. 28, 2020

(54) DEVICE PROVIDING BODY TEMPERATURE REGULATION AND/OR THERAPEUTIC LIGHT DIRECTED TO VASCULATURE

(71) Applicant: Quantum Dynamics, LLC, Cambridge, MA (US)

(72) Inventors: Ruben F. Salinas, Andover, MA (US); John J. Kruse, Petal, MS (US)

(*) Notice: Subject to any disclaimer, the term of this patent is extended or adjusted under 35 U.S.C. 154(b) by 0 days.

(21) Appl. No.: 16/208,713

(22) Filed: Dec. 4, 2018

(65) Prior Publication Data
US 2019/0175935 A1 Jun. 13, 2019

Related U.S. Application Data

(63) Continuation of application No. 15/188,653, filed on Jun. 21, 2016, now Pat. No. 10,183,174.
(Continued)

(51) Int. Cl.
*A61N 5/06* (2006.01)
*A61F 7/00* (2006.01)
(Continued)

(52) U.S. Cl.
CPC ............ *A61N 5/0613* (2013.01); *A61F 7/007* (2013.01); *A61F 7/10* (2013.01); *A61N 5/0616* (2013.01); *A61N 5/0618* (2013.01); *A61N 5/0625* (2013.01); *A61F 2007/108* (2013.01); *A61N 2005/005* (2013.01); *A61N 2005/007* (2013.01); *A61N 2005/0626* (2013.01); *A61N 2005/0645* (2013.01); *A61N 2005/0652* (2013.01);
(Continued)

(58) Field of Classification Search
CPC .. A61N 5/0613; A61N 5/0625; A61N 5/0618; A61N 5/0616; A61N 2005/0645; A61N 2005/005; A61N 2005/0626; A61N 2005/067; A61N 2005/0652; A61N 2005/0659; A61N 2005/0661; A61N 2005/0662; A61N 2005/007; A61F 7/10; A61F 7/007; A61F 2007/108
See application file for complete search history.

(56) References Cited

U.S. PATENT DOCUMENTS

2004/0122492 A1* 6/2004 Harth ................... A61N 5/0613
607/88
2016/0256706 A1* 9/2016 Harrison .............. A61N 5/0622

* cited by examiner

*Primary Examiner* — Rex R Holmes
(74) *Attorney, Agent, or Firm* — Thomas A. O'Rourke; Bodner & O'Rourke, LLP

(57) ABSTRACT

One bracelet embodiment provides therapeutic blood irradiation at a first wrist region using a first module, and body temperature regulation/irradiation at a second wrist region using a second module. A connector couples one end of the modules together, while an attachment band releasably couples the second ends together, for attachment to the wrist. The first module includes first and second distributed pluralities of lights respectively emitting 850 and 660 nm wavelengths, and a third plurality emitting 630 nm, 532 nm, and 450 nm wavelengths, positioned in a row substantially parallel to the arm of the user. The second module includes first and second rows of lights on first and second sides of a cooling unit, each emitting 405 nm wavelengths, with the two rows positioned for penetration to the radial and ulnar arteries. The bracelet includes a microprocessor, LED screen, and firmware for displaying a GUI permitting treatment protocol selections.

18 Claims, 68 Drawing Sheets

Related U.S. Application Data

(60) Provisional application No. 62/231,007, filed on Jun. 22, 2015, provisional application No. 62/338,023, filed on May 18, 2016.

(51) Int. Cl.
 *A61F 7/10* (2006.01)
 *A61N 5/00* (2006.01)
 *A61N 5/067* (2006.01)

(52) U.S. Cl.
 CPC ............... *A61N 2005/0659* (2013.01); *A61N 2005/0661* (2013.01); *A61N 2005/0662* (2013.01)

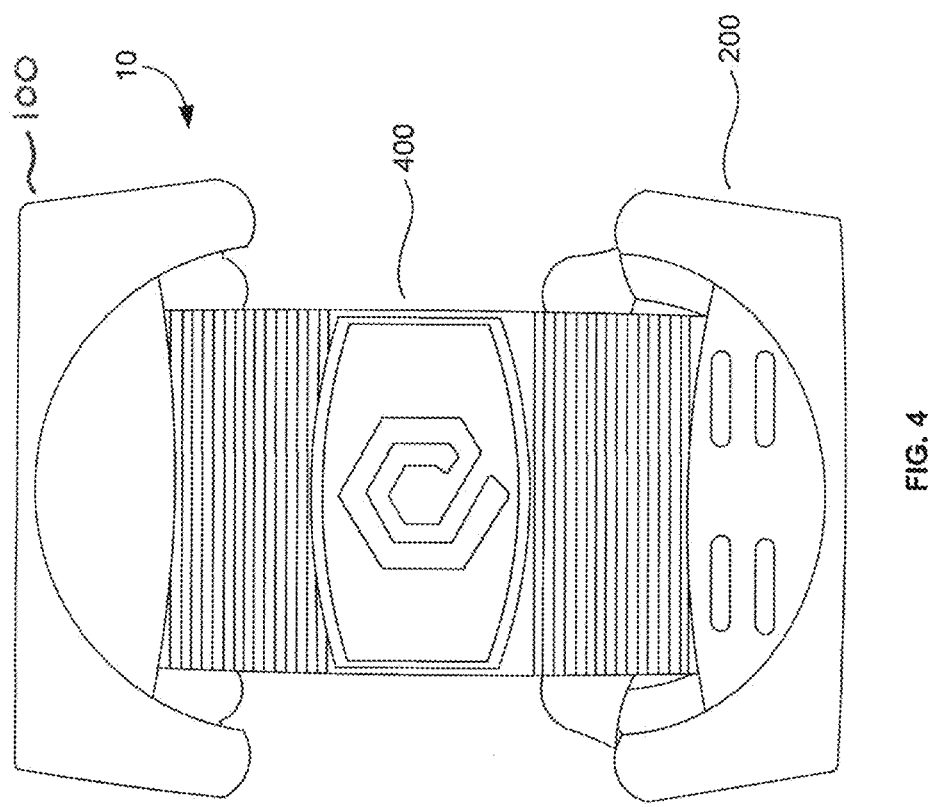

(Second Treatment Module)

(First Treatment Module)

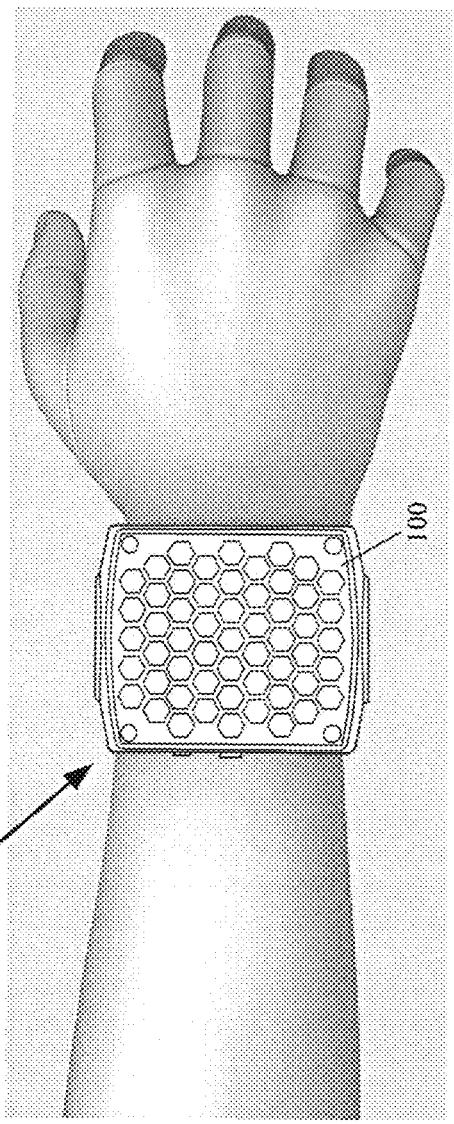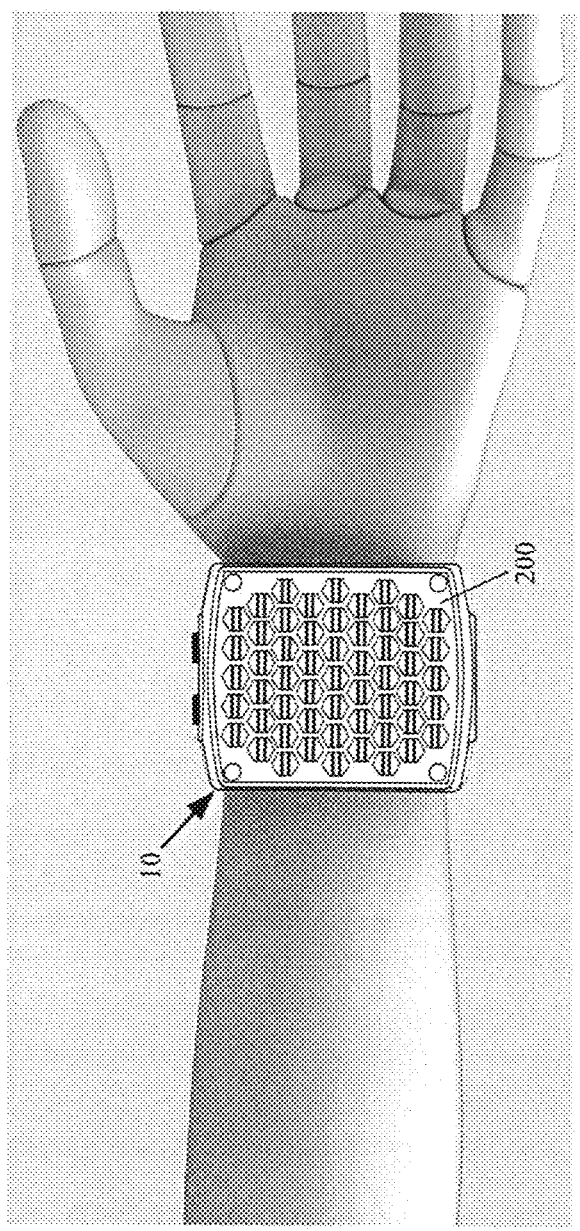

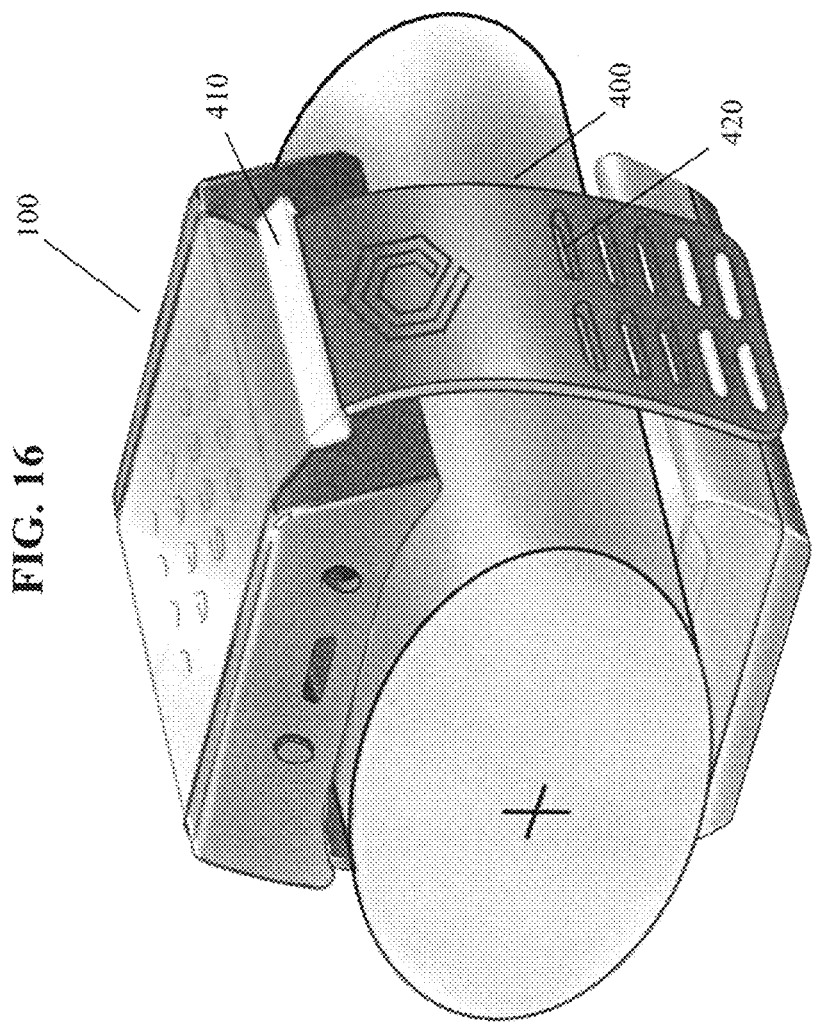
FIG. 16
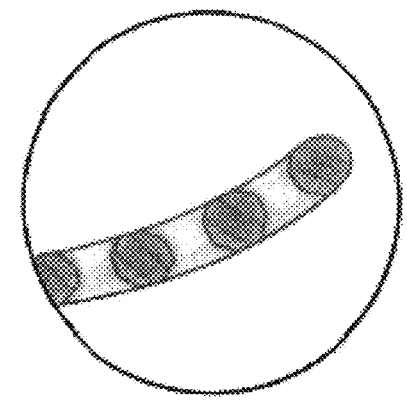
FIG. 17
FIG. 18
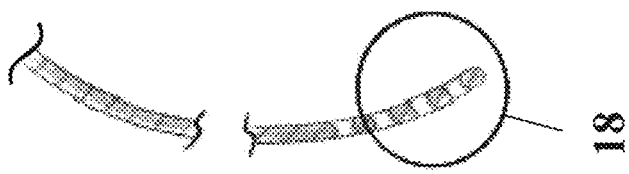
FIG. 17A

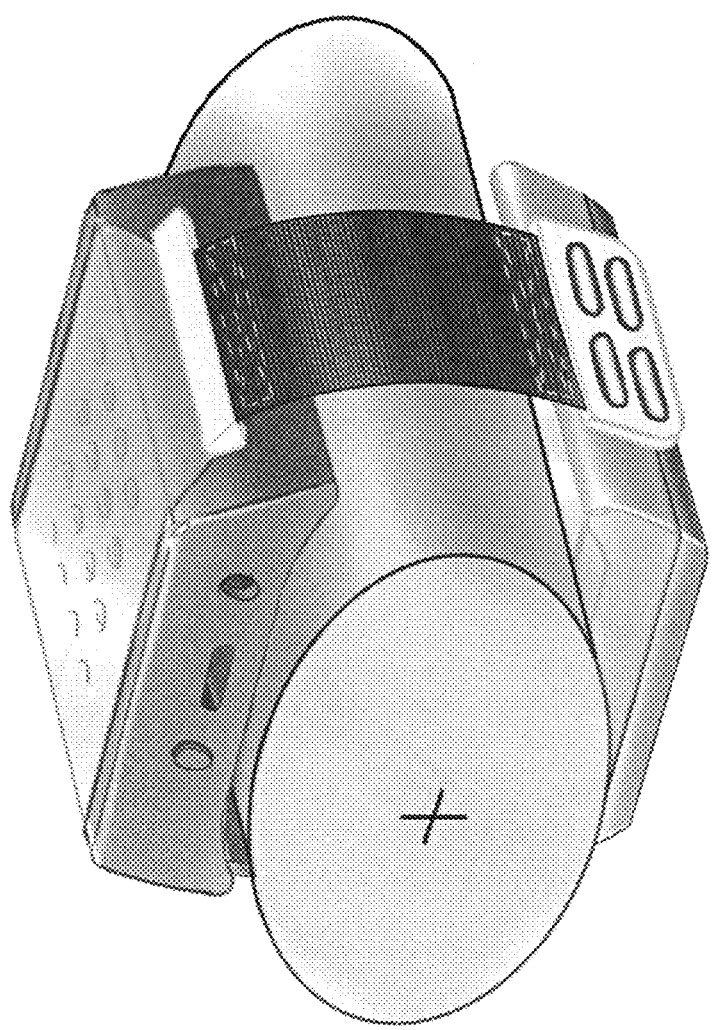
FIG. 19
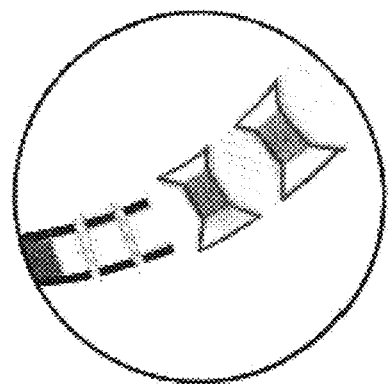
FIG. 21
FIG. 20
FIG. 20A

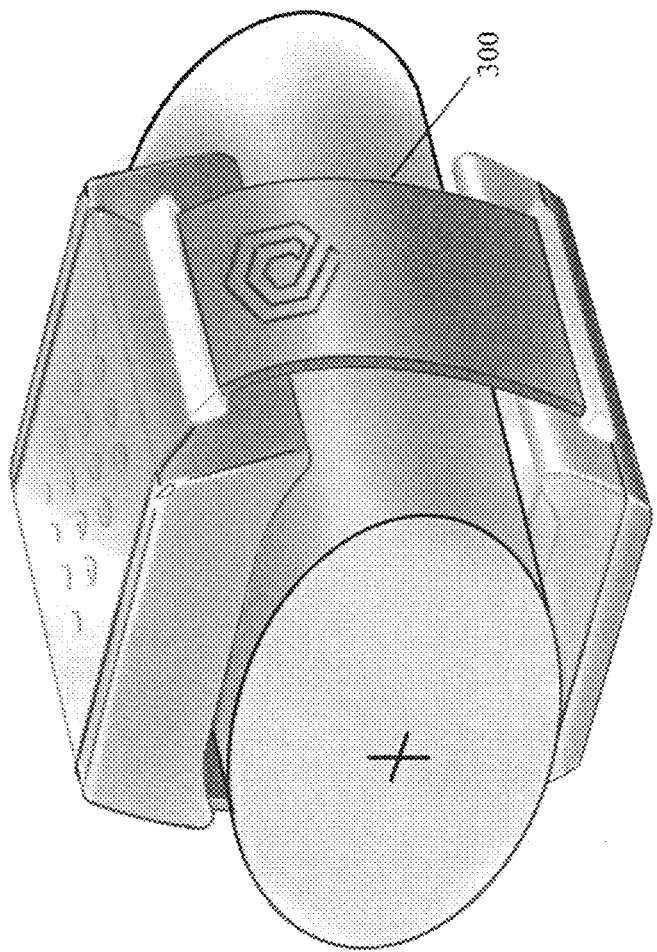
FIG. 22
FIG. 23A
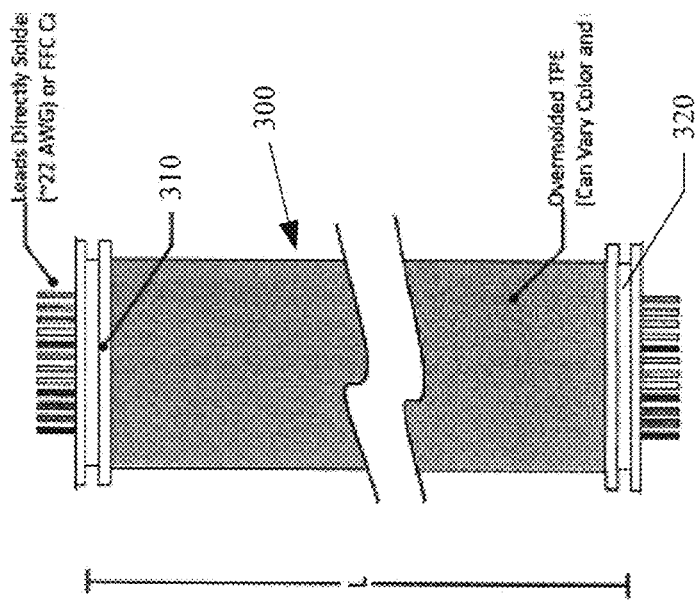
FIG. 23
FIG. 24

| Wrist Width (mm) | | |
|---|---|---|
| % | Male | Female |
| 25 | 66 | 56 |
| 50 | 69 | 58 |
| 95 | 74 | 64 |

| Hand Width (mm) | | |
|---|---|---|
| % | Male | Female |
| 25 | 109 | 99 |
| 50 | 112 | 102 |
| 95 | 117 | 107 |

| Dorsum (mm) | | |
|---|---|---|
| % | Male | Female |
| 25 | 76 | 71 |
| 50 | 79 | 74 |
| 95 | 81 | 79 |

| Palm (mm) | | |
|---|---|---|
| % | Male | Female |
| 25 | 109 | 99 |
| 50 | 112 | 102 |
| 95 | 117 | 107 |

FIG. 29A
| % | Wrist Thickness (mm) | |
|---|---|---|
| | Male | Female |
| 25 | 38 | 31 |
| 50 | 43 | 38 |
| 95 | 51 | 43 |
FIG. 29B
| % | Wrist Circumference (mm) | |
|---|---|---|
| | Male | Female |
| 25 | 158 | 137 |
| 50 | 175 | 150 |
| 95 | 193 | 162 |
FIG. 29C
| Band Length Analysis | |
|---|---|
| Demographic | Length (mm) |
| 25% F | 47 |
| 50% F | 54 |
| 25% M | 56 |
| 95% F | 60 |
| 50% M | 63 |
| 95% M | 72 |
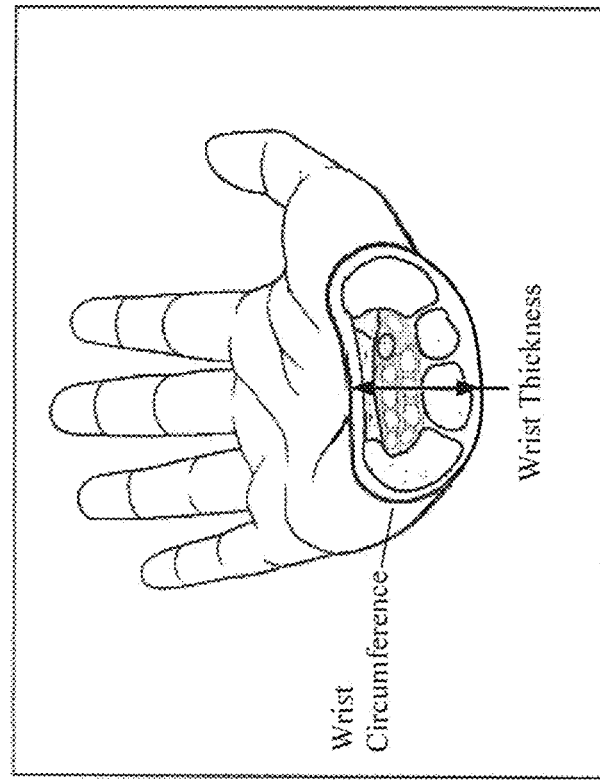
FIG. 29
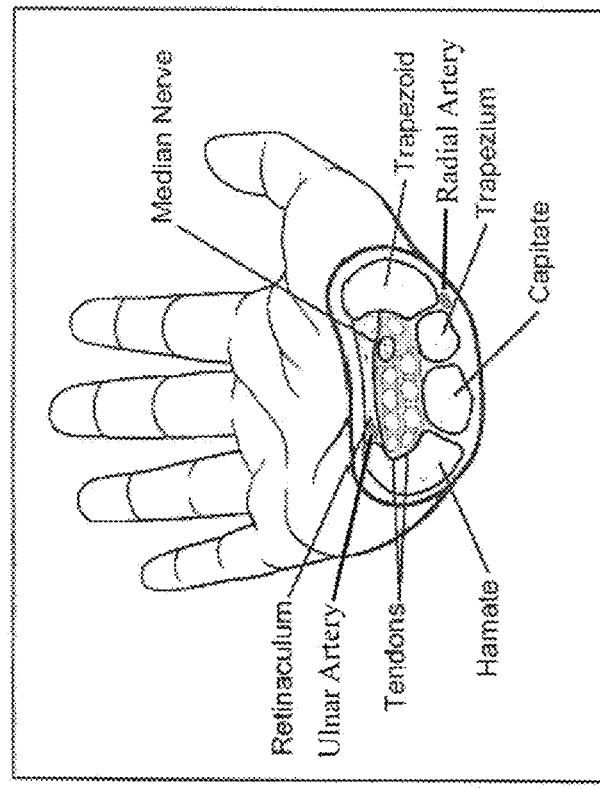
FIG. 30

| Wrist Device Area : Ideal / Maximum | | |
|---|---|---|
| | 95th Percentile Male | 5th Percentile Female |
| Ideal Wrist Device Area | 51mm$^2$ | 64mm$^2$ |
| Max Wrist Device Area | 73mm$^2$ | 64mm$^2$ |

| Volume Key (mm) | | |
|---|---|---|
| L | W | H |
| 51 | 51 | 19 |
| 64 | 64 | 19 |
| 73 | 73 | 19 |

FIG. 46
Housing LED Window Attribute Comparison

| Lens Material | Borosilicate | Quartz | Polycarb | Sapphire | Silica |
|---|---|---|---|---|---|
| Light Transmission (%) | 90-94 | 90 | 86 | 90 | 88 |
| Thermal Expansion | 3.25 x 10⁻⁶/K | 0.57 x 10⁻⁶/K | 65 x 10⁻⁶/K | 5.3 x 10⁻⁶/K | 0.52 x 10⁻⁶/K |
| Knoop Hardness | 480 | 522 | 520 | 1500-2000 | 522 |
| (Dent Resistance) | | | | | |
| Mohs Hardness | 7 | 6 | <2.5 | 9 | 6.5 |
| (Scratch Resistance) | | | | | |
| Young's Modulus | 64 Gpa | 72.7 Gpa | 2.4 Gpa | 470 Gpa | 74 Gpa |
| Compressive Strength | 100 Mpa | 1100 Mpa | 55 Mpa | 2000 Mpa | 1.13 Mpa |
| Tensile Strength | 7 Mpa | 48 Mpa | 80 Mpa | 275 Mpa | 49 Mpa |
| Price | — | — | — | — | — |

Housing Window Light Transmission Comparison

FIG. 49

Battery Research: Power Budget for Concept 1

| | | | | | | | |
|---|---|---|---|---|---|---|---|
| IR LED | 1.5 | 1 | 0.2 | 0.3 | 15 | 22.5 | 4.5 |
| Red 660 LED | 1.8 | 1 | 0.1 | 0.18 | 15 | 27 | 2.7 |
| Red 630 LED | 2.1 | 1 | 0.15 | 0.315 | 5 | 10.5 | 1.575 |
| Green Led | 3.1 | 1 | 0.15 | 0.465 | 5 | 15.5 | 2.325 |
| Blue LED | 2.9 | 1 | 0.15 | 0.435 | 5 | 14.5 | 2.175 |
| UV LED | 3.1 | 1 | 0.1 | 0.31 | 12 | 37.2 | 3.72 |
| TEC | 7.4 | | | 4.07 | 1 | 7.4 | 4.07 |
| PCBs | | | | 0.5 | 1 | | 0.5 |
| | | | | 1.65 | | | 21.565 |

| | 1 | 7.4 | 2914 |
| --- | --- | --- | --- |
| | 1.333 | 7.4 | 3885 |
| | 2 | 7.4 | 5828 |

*note -- for the purposes of the Power Budget, LEDs were assumed to be on at their lowest power setting for the entire therapy session. The TEC was assumed to be cycled @ 1/2Ds with a 33% duty cycle.

FIG. 50

Battery Research: Power Budget for Concept 2

| | | | | | | |
|---|---|---|---|---|---|---|
| IR LED | 1.5 | 0.2 | | 0.3 | 9 | 2.7 |
| Red 660 LED | 1.8 | 0.1 | | 0.18 | 9 | 1.62 |
| Red 630 LED | 2.1 | 0.15 | | 0.315 | 5 | 1.575 |
| Green LED | 3.1 | 0.15 | | 0.465 | 5 | 2.325 |
| Blue LED | 2.9 | 0.15 | | 0.435 | 5 | 2.175 |
| UV LED | 3.1 | 0.1 | | 0.31 | 4 | 1.24 |
| TEC | 7.4 | | | 4.07 | 1 | 4.07 |
| PCBs | | | | 0.5 | 3 | 0.5 |
| | | 1.65 | | | 7.4 | 16.205 |

| | | | |
|---|---|---|---|
| 1 | 7.4 | | 3190 |
| 1.333 | 7.4 | | 2919 |
| 2 | 7.4 | | 4380 |

*note – for the purposes of the Power Budget, LEDs were assumed to be on at their lowest power setting for the entire therapy session. The TEC was assumed to be cycled @ 120s with a 33% duty cycle.

App – Activity Feed

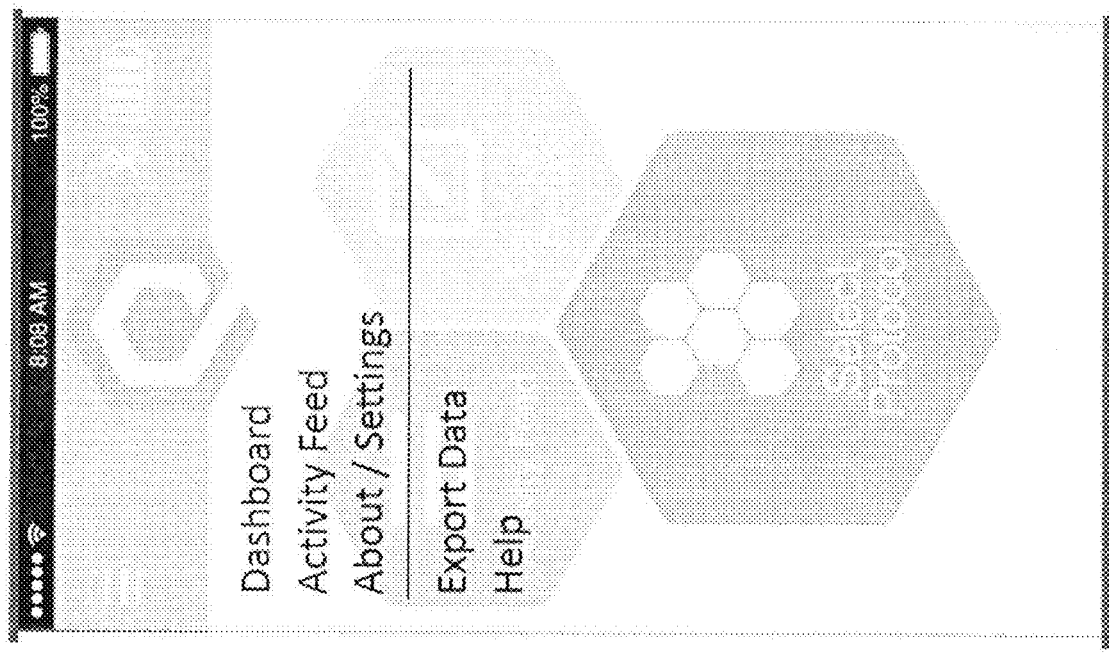

FIG. 71

Programmable parameters table

| Time | 1 Min | 3 Min | 5 Min | 15 Min | 30 Min | 60 Min | ###### |
|---|---|---|---|---|---|---|---|
| Pulse | Cont. | 1 Hz | 3 Hz | 5 Hz | 10 Hz | 20 Hz | 100 Hz |
| Duty Cycle | 50% | 60% | 70% | 80% | 90% | 100% | Cont. |
| 405nm Power | 0% | 20% | 40% | 60% | 80% | 100% | |
| 532nm Power | 0% | 20% | 40% | 60% | 80% | 100% | |
| 630nm Power | 0% | 20% | 40% | 60% | 80% | 100% | |
| 660nm Power | 0% | 20% | 40% | 60% | 80% | 100% | |
| 850nm Power | 0% | 20% | 40% | 60% | 80% | 100% | |

FIG. 72

| Protocols | Performance 30 | Performance 60 | Performance 90 | Performance 120 | Wellness/Sleep/Relax | Jetlag | Muscle Activation | Spot Treatment | Custom |
|---|---|---|---|---|---|---|---|---|---|
| Time (mins) | 30 | 60 | 90 | 120 | 30 | 30 | 15 | 15 | Custom |
| Pulse | Cont. | Cont. | 100 Hz | 100 Hz | 10 Hz | 100 Hz | Cont. | Cont. | Custom |
| Duty Cycle | 100% | 100% | 80% | 60% | 10% | 50% | 50% | 50% | Custom |
| 405nm Power | 100% | 100% | 80% | 60% | 0% | 100% | 0% | 0% | Custom |
| 532nm Power | 100% | 100% | 80% | 60% | 100% | 0% | 0% | 0% | Custom |
| 630nm Power | 100% | 100% | 80% | 60% | 0% | 0% | 100% | 100% | Custom |
| 660nm Power | 100% | 100% | 80% | 50% | 20% | 100% | 100% | 100% | Custom |
| 850nm Power | 100% | 100% | 80% | 60% | 100% | 100% | 100% | 100% | Custom |

DEVICE PROVIDING BODY TEMPERATURE REGULATION AND/OR THERAPEUTIC LIGHT DIRECTED TO VASCULATURE

CROSS REFERENCES TO RELATED APPLICATIONS

This application is a continuation of U.S. application Ser. No. 15/188,653, filed Jun. 21, 2016, now issued as U.S. Pat. No. 10,183,174, which claims priority on U.S. Provisional Application Ser. No. 62/231,007, filed on Jun. 22, 2015, and on U.S. Provisional Application Ser. No. 62/338,023, filed on May 18, 2016, all disclosures of which are incorporated herein by reference.

FIELD OF THE INVENTION

The present invention relates to methods and apparatus for regulating body temperature, and for applying low level light therapy (LLLT), also known as photobiomodulation, over tissue to improve immune function, blood rheology, to regulate sleep and reduce jetlag symptoms, to improve athletic performance, and reduce inflammation, and for neuromodulation/sense of well-being, to improve homeostasis in the body, and for applying LLLT over injuries and lesions to improve wound and soft tissue healing, and to provide relief for acute and chronic pain. The invention is also directed to a portable and convenient apparatus with a user interface, and a system and methodology by which the user can self-administer light and facilitate cooling of the body/blood without any need for medical or technical supervision.

BACKGROUND OF THE INVENTION

One of the earliest studies of blood irradiation therapy was published in 1981 by Russian scientists, i.e., Mishalkin, E., editor, "Application of direct laser irradiation in experimental and clinical heart surgery (in Russian)," Novosibirsk: Nauka. The studied technique required insertion of a cannula that contained a plastic laser catheter into a vein in the forearm of a human patient, and feeding the low intensity laser light into the blood stream through the cannula. This was an early mode of treatment of cardiovascular diseases, in which both the microcirculation and the rheological properties of blood were improved.

Later published studies further demonstrated that blood rheology can be improved particularly with green or blue wavelengths of laser light (see, Mi, et al., "A comparative study of 632.8 and 532 nm laser irradiation on some rheological factors in human blood in vitro," Journal of Photochemistry and Photobiology, 74:1: 7-12 (2004); and Gasparyan, L, "Laser irradiation of the blood," Laser Partner Clinixperience, 58 (2003)).

Later reported studies also suggested that it does not matter if the light energy is coherent (i.e., laser light), but that the light energy instead be of an effective wavelength and be delivered at the correct dosage. For example, incoherent red from a Light Emitting Diode (LED) is expected to perform as well as laser light to produce low-power laser clinical effects; and the primary difference between laser light and LED light is that the laser's coherent beam produces "speckles" of relatively high power density which can cause local heating of inhomogeneous tissues (see, Karu, T. I., "The Science of Low Power Laser Therapy," Gordon and Breach Scientific Publications, London (1998)). Other studies/reports have described additional benefits and aspects of LLLT (see e.g., Michael R. Hamblin, "Mechanisms of Low Level Light Therapy," (2008); Scott Roberts, "LED Light Therapy"; and Tiina Karu, "Action Spectra, Their Importance for Low Level Light Therapy"). The studies have also shown that use of 405-450 nm wavelengths (the violet-blue region of the spectrum) are effective with respect to cytochrome c-oxidase.

The studies have also shown that the basis for the effectiveness of the wavelengths of the LLLT relates to quantum mechanical theory (QMT), in that per QMT, light is composed of photons, the energy of which depends upon its wavelength. The photons of the light directed onto living tissue will either be absorbed or scattered, and only the photons that are absorbed may interact with the living tissue. The absorbed photons, typically for the red and NIR wavelengths, may interact in one of three ways—i) the energy of the photon may create heat; ii) the molecular absorption of a photon may result in emission of a different photon having a longer wavelength; or iii) the photon may trigger any one of a number of processes known as photochemistry, which is particularly relevant for the blood.

The normal circulating blood, i.e., blood containing non-aggregated red blood cells (RBCs), performs many important life functions in the mammalian body. Blood provides a supply of oxygen to living tissues via the hemoglobin internally carried by RBCs. Blood provides a supply of nutrients such as glucose, amino acids, and fatty acids. These nutrients are dissolved in the blood or are bound to plasma. Blood acts to remove waste products such as carbon dioxide, urea, and lactic acid. Blood performs diverse immunological functions, including the circulation of multiple kinds of white blood cells, as well as the detection and binding of foreign material by antibodies. Blood provides the cascade of proteins needed for blood clotting or coagulation as part of the body's self-repair mechanisms. Blood provides the entities for messenger functions, including the transport of hormones and the chemical signaling of tissue damage. Blood serves to regulate body pH via blood acidity. Blood regulates the core body temperature. Blood also performs many hydraulic (fluid mechanical) functions.

A blood sample from an unhealthy subject shows that his/her red blood cells may be joined together and form an aggregate, and the presence of such RBC aggregates creates "high viscosity" and a marked resistance to flow for the circulating blood in that individual. The aggregated RBCs in blood of such an unhealthy subject would form irregular clusters or masses of cells, causing at least some functional roles of blood to become severely compromised. It is therefore medically desirable and clinically therapeutic if such RBC aggregates in the circulating blood could be made to dissociate and disaggregate into separated and individual red blood cells.

The present invention is particularly configured to provide portable biostimulation using low level light therapy (LLLT), also known as photobiomodulation, at particularly beneficial wavelengths, using particular power levels and pulsing at a duty cycle for the application of the necessary amount of energy, at an optimal delivery location to achieve in-vivo reversal of red blood cell aggregation, without invading the tissues or organs of the living subject—a clinical result which leads to a lower blood viscosity and improved blood circulation. In one embodiment of the present invention, light energy is configured for location-specific delivery using a bracelet to irradiate arterial and venous blood located beneath the skin of the wrist/forearm (e.g., the radial and ulnar arteries). The present invention may also be advantageously utilized upon any other region of the body, and thus may be similarly adapted and directed to use on the neck, the torso, or any other portion of any of a person's limbs, including, but not limited to, the foot, ankle, calf muscle, knee, thigh, etc. In addition the components described herein may also be utilized in a helmet-like/helmet worn device to be worn on the person's head for treatment thereto. Therefore, any description hereinafter that is described with reference to the wrist region, is not intended to be limited to such applicability.

The vasculature lying adjacent to the wrist is particularly receptive to biostimulation. The quantity of blood flow at that location is quite large; and the rate of blood flow is routinely higher per unit area of tissue in comparison to the rate of blood flow into other anatomic locales such as the brain, or the liver, or the muscles. Therefore, the therapeutic benefits of such irradiation light therapy are quickly spread throughout the whole body via the blood circulation system.

The benefits of the particular red wavelength(s) of light used herein are: a) the wavelength(s) are readily absorbed by the mitochondria and stimulatory therein; b) the wavelength(s) also stimulate growth; c) the wavelength(s) do not penetrate deep below the skin surface and into the tissue below; d) the wavelength(s) are non-thermal, and therefore do not create any burns.

The benefits of the infrared wavelength(s) used herein are: a) the wavelength(s) are absorbed through the cell walls (acting differently between cells) and therefore cell response is more wavelength specific, responding differently to different wavelengths; and b) the wavelength(s) are more penetrative through the tissue, for treatment through intact skin, possibly being more stimulatory than red light.

The wavelength(s) in or near the start of the ultraviolet spectrum used herein are particularly beneficial, as it has been shown that both the light frequencies in the red and infrared range most typically used in LLLT as well as wavelengths in the violet and blue range, may influence the localized production and release of nitric oxide, and may stimulate vasodilation through the effect of the nitric oxide on cyclic guanosine monophosphate (cGMP), which is a cyclic nucleotide derived from guanosine triphosphate (GTP), which acts as a messenger, and is regarded as an activation mechanism for intracellular protein kinases. The bracelet (or any other form) of the present invention is therefore designed to be effective for patients who would benefit from increased localized nitric oxide availability, and thus may include wavelengths at and/or in the ultraviolet spectrum, and also blue wavelengths of light. Also, Tiina Karu notes the following in "Action Spectra, Their Importance for Low Level Light Therapy"):

"Recall that in the wavelength range 310-500 nm, a maximum stimulating effect was obtained with a radiation dose one order of magnitude less than in the longer-wave spectral range (3, 4). This is noted in FIG. 3 by Curves 1 and 2. The bands in the action spectrum were identified in (20, and reviewed in 9) by analogy with the metal-ligand systems absorption spectra characteristic of this spectral range. The regions 400-450 nm and 620-680 nm are characterized by the bands pertaining to complexes with charge transfer in a metal-ligand system, and within 760-830 nm, these are d-d transitions in metals (21-23). The region 400-420 nm is typical of π-π* transitions in a porphyrin ring (24)."

Research has shown that to be efficacious, the intensity of the light applied to treat injuries at a skin surface may preferably be between 4 mW/cm$^2$ and 15 mW/cm$^2$, which would require, assuming 5% penetration through the skin, application of light at an intensity of 80 mW/cm$^2$ at the low end (net penetration of 4 mW/cm$^2$), and an intensity of 300 mW/cm$^2$ at the high end (net penetration of 15 mW/cm$^2$). It has furthermore been found that apart from the deleterious effect of heating, that long duration pulses may not be optimal for treatment, i.e., pulses such as 50 microsecond on and 250 microsecond off (less than a 50% duty cycle), with an average intensity of 30 mW/cm$^2$ may desirably provide a total of 180 mW/cm$^2$ during each 50 microsecond cycle.

The Mammalian body temperature is normally controlled by an internal autonomic regulatory system referred to herein as the thermoregulatory system. Normally, when body and or environmental temperatures are high, dilation of certain blood vessels favors high blood flow to the noted heat exchange surfaces, thus increasing heat loss to the environment and temperature reduction in the deep body core region. Conversely, as environmental and/or body temperatures fall, vasoconstriction reduces blood flow to these surfaces and minimizes heat loss to the environment.

However, there are situations in which it is desirable to manipulate the transfer of heat across skin surfaces, to modulate the body temperature, where particular applications may include the treatment of normal and abnormal physiological conditions, e.g., disease and/or discomfort, particularly for alleviation or treatment of hot flashes, treatment of exercise or work induced hyperthermia, treatment of stroke, treatment of cystic fibrosis symptoms, treatment of multiple sclerosis symptoms, and the like. By "treatment" it is meant that it results in at least an alleviation in one or more of the symptoms associated with the condition being treated, e.g. a reduction in discomfort, amelioration or elimination of symptoms, etc. Core body cooling, (or heating) may be useful not only for therapeutic treatment regimens, but also as a component of improving athletic or industrial performance. Where the herein disclosed device is also used for body temperature regulation during a workout, it may serve: to increase exercise efficiency and capacity; to extend exercise times including longer time to reach 50% strength reduction; to help the user to achieve a higher peak force in resistance training; to lower creatine kinase blood levels (muscle damage index); to naturally and safely stimulate the production of body and brain chemicals that increase physical energy and to attain a sense of well-being derived from the release of certain neurotransmitters such as serotonin and dopamine.

Therefore, another aspect of the present invention is its ability to manipulate the transfer of heat across skin surfaces to modulate body temperatures. The device may include a cooling apparatus, such as a cold pack, an ice pack, or a thermoelectric cooling unit, positioned in proximity to the skin of the wearer of the device. The device may be configured to provide thermal pulses to the wearer's skin surface (e.g., a 33% duty cycle @120 seconds—30 second on and 90 seconds off, or instead, may preferably be a 120 second cycle, with 20 seconds on and 100 seconds off).

In some cases, the average rate of the initial temperature adjustment may be greater in magnitude than the average rate of the return temperature adjustment. Also, the thermal pulse may include a first temperature adjustment at the region of the at least one thermoelectric unit adjacent the skin surface from a first temperature to a second temperature at a first average rate of between about 0.1° C./sec and about 10.0° C./sec, and a second temperature adjustment from the second temperature to a third temperature at a second average rate of between about 0.1° C./sec and about 10.0° C./sec, wherein a difference in magnitude between the first temperature and the third temperature may be less than 25% of a difference in magnitude between the first temperature and the second temperature.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment of the present invention, a bracelet may be configured for therapeutic blood irradiation at a first wrist region of the user using a first treatment module, and for body temperature regulation at a second wrist region of a user using a second treatment module. Alternatively, the first treatment module may operate to provide body temperature regulation and the second treatment module may operate to provide therapeutic blood irradiation, and further still, an embodiment of the device (e.g., for the neck) may have a single module configured to provide both therapeutic blood irradiation and the body temperature regulation. It will be understood, therefore, that either the first or the second treatment modules may have either a body temperature regulation and/or a therapeutic blood irradiation function. Accordingly, for purposes of illustration only, in the remainder of the description of the present invention herein, reference may be made to the first treatment module in connection with therapeutic blood irradiation and the second treatment module in connection with body temperature regulation functions, without intending to so limit the present invention to only one such embodiment.

A connector band may flexibly couple the first treatment module to the second treatment module, for positioning on the wearer's wrist, and the connector band may be further configured to electrically couple the second treatment module to the first treatment module. The flexible connector band may include means for adjusting a length of the band, to accommodate different size wrists for different size users. An attachment band may be fixedly secured to the first treatment module, and may be configured for a portion thereof to be releasably coupled to the second treatment module, so that the user may attach the bracelet to his/her wrist. The attachment band may be formed of a thermoplastic elastomer, and may also be configured to be adjustably coupled to the second treatment module, to further accommodate different wrist sizes.

The first treatment module may broadly include one or more light sources configured to emit one or more selective wavelengths of light from a first side of the first treatment module. The one or more light sources may be LEDs, quantum dots, and/or laser diodes. The one or more light sources of the first treatment module may be positioned to provide therapeutic blood irradiation over a predefined area. The one or more light sources may be configured to generate light at any wavelength within each of the ultraviolet, the visible, and the infrared spectrums (i.e., the one or more light sources can generate an unlimited number of wavelengths). In one embodiment, the one or more light sources may emit the selective wavelengths of light within the range of about 350 nm to about 1000 nm, and may preferably emit the selective wavelengths of light within the range of about 450 nm to about 850 nm. More preferably, the one or more light sources may emit wavelengths of light selected from: about 450 nm, about 532 nm, about 630 nm, about 660 nm, about 660 nm, and about 850 nm. Use within this specification of the relative term "about" in connection with a numeric value is intended to mean±20% of the stated numeric value; therefore the one or more light sources may emit wavelengths of light selected from: 450 nm±20 nm, 532 nm±20 nm, 630 nm±20 nm, 660 nm±20 nm, 660 nm±20 nm, and 850 nm±20 nm. In one embodiment, the one or more light sources may emit wavelengths of light at the wavelengths of 850 nm, 660 nm, 630 nm, 532 nm, and 450 nm. The one or more light sources that may emit the light at the 850 nm and the 660 nm wavelengths/ranges may use a total amount of power in the range of about 300 mW to about 500 mW, and may, in one embodiment, use a total of 415 mW. The one or more light sources that may emit the light at the 630 nm, the 532 nm, and the 450 nm wavelengths/ranges may use a total amount of power in the range of about 300 mW to about 500 mW, and may, in one embodiment, use a total of 335 mW.

Examples of the lights that may be used include IR LED's (a descriptive name) sold under the trademark names of: OSRAM: SFH 4253-Z, OSRAM: SFH 4716AS, VISHAY VSMY3850-GS08, EVERLIGHT ELECTRONICS HIR-006/L298-P01/TR and QT BRIGHTTEK: QBHP684U-IRU.

Other examples of the lights that may be used include red (e.g., 660 nm) LED's (a descriptive name) sold under the trademark names of: OSRAM: LH CPDP-2T3T-1, OSRAM: LH WSAM-1T3T-1-Z, LUMILEDS: LXZI-PA01, EVERLIGHT ELECTRONICS: ELSH-Q91E1-OLPNM-JD3D8, CREE XP-E and CREE: XQEPHR-00-0000-000000901.

Further examples of the lights that may be used include RGB LED's (a descriptive name) sold under the trademark names of: OSRAM: LE RTDUW S2W, OSRAM: LRTDC9TP-EAFB-GHQN, KINGBRIGHT: AAD1-9090BRGC-01/3, CREE XM-L, and LED ENGIN Inc.: LZP-00MD00-0000.

Still further examples of the lights that may be used include UV LED's (a descriptive name) sold under the trademark names of: BIVAR: SM0603UV-400, LITE-ON: LTPL-C034UVH405, VISHAY: VLMU3100-GS08 and LUMILEDS: LHUV-0400-0400

In one embodiment, the one or more light sources of the first treatment module may be a plurality of lights sources that are configured to emit the 850 nm wavelength/ranges of light, a plurality of lights sources configured to emit the 660 nm wavelength/ranges of light, and a plurality of lights sources configured to emit the 630 nm, 532 nm, and 450 nm wavelengths/ranges of light. The plurality of lights sources configured to emit the 850 nm wavelength/ranges of light may be distributed in three rows to provide irradiation over a desired area, which in one embodiment may be a substantial portion of a 25 square centimeter area. The plurality of lights sources configured to emit the 660 nm wavelength/ranges of light may also be distributed in three rows to provide irradiation over a substantial portion of the 25 square centimeters. Furthermore, the plurality of lights sources configured to emit the 630 nm, 532 nm, and 450 nm wavelengths/ranges of light may be positioned in a row that may be oriented to be substantially perpendicular to a line between the flexible connector band and the flexible attachment band (i.e., it may be oriented along the axis of the device—being parallel to the arm of the user when worn on his/her wrist).

The second treatment module may broadly include a cooling device, such as a cooling pack (i.e., a bag configured to separate water from ammonium nitrate, calcium ammonium nitrate, or urea, whereby agitating the bag causes mixing of the components to produce an endothermic reaction, and thus cooling), an ice pack, and/or a thermoelectric cooling (TEC) unit, which may be configured to draw away heat and thereby cool a first side of the second treatment module. A gasket may be positioned around a side of the cooling unit, and may be thermally insulating to better ensure the directionality of the heat transfer from one side of the TEC to the other side. Also, a thermally conductive material may be positioned on at least a portion of the first side of the second treatment module, to more effectively draw heat away from the wearer's wrist and towards the first side of the cooling unit. A heat sink may furthermore be used to draw heat away the second side of the thermoelectric cooling unit towards a second side of the second treatment module, to be dispersed therefrom. A peel and stick disposable cushion may be releasably secured to the first side of the second treatment module.

The cooling unit in the second treatment module may be substantially centered therein. The second treatment module may also broadly include a first row of light sources on a first side of the cooling unit, and a second row of light sources on a second side of the cooling unit, with each of the two rows oriented to be substantially perpendicular to a line between the connector band and the attachment band (i.e., being oriented along the axis of the device—being parallel to the arm of the user when worn on his/her wrist). These first and second rows of light sources in the second treatment module may thus be respectively positioned to achieve optimal penetration to the radial and ulnar arteries in the wearer's wrist, and may be configured to emit light at a wavelength of 405 nm.

The bracelet may also broadly include an LED screen, and a microprocessor that may be coupled to the LED screen, the cooling unit, and the light sources. Firmware and/or software implemented therein may cause the display of a Graphical User Interface (GUI) on the LED screen, to permit selection by the user from one or more preprogrammed treatment protocols and/or a customized treatment option, where the customized treatment may permit selection of a treatment time, a cooling temperature, and a light intensity for each of the wavelengths.

The first side of the first treatment module may have a contoured surface configured to roughly conform to the posterior (dorsal) aspect of the wearer's wrist, and the first side of the second treatment module may have a contoured surface configured to roughly conform to the anterior (ventral) aspect of the wearer's wrist. The contoured surface may also be configured to suitably be applied to the person's ankles, or neck, or other body region, which may be accommodated by a band extender.

The bracelet may be configured to be powered by a 2000 mAh, 7.4 V lithium polymer battery, which may be configured to provide adequate power for body temperature regulation and therapeutic blood irradiation for any of the desired treatment protocols, which may be for a portion of an hour, for a full hour, or even longer.

BRIEF DESCRIPTION OF THE DRAWINGS

The description of the various example embodiments is explained in conjunction with appended drawings, in which:

FIG. 4 illustrates a view showing the attachment module of the bracelet of FIG. 1;

FIG. 8A illustrates a view of the bracelet of FIG. 1 attached to a user's wrist, showing the first treatment module in contact with the posterior (dorsal) aspect of the wearer's wrist;

FIG. 8B illustrates a view of the bracelet of FIG. 1 attached to a user's wrist, showing the second treatment module in contact with the anterior (ventral) aspect of the wearer's wrist;

FIG. 16 illustrates a perspective view of the bracelet of FIG. 1, attached to the wrist of a user, showing the attachment band;

FIG. 17 is a cross-sectional view through the attachment band shown in FIG. 16;

FIG. 17A shows a table of different lengths that may be used for the attachment band of FIG. 17;

FIG. 18 shows a portion of the cross-sectional view of FIG. 17 enlarged;

FIG. 19 illustrates a perspective view of the bracelet of FIG. 1, attached to the wrist of a user, showing an alternative embodiment of the attachment band;

FIG. 20 is a cross-sectional view through the attachment band of FIG. 19;

FIG. 20A shows a table of lengths for the attachment band of FIG. 20;

FIG. 21 shows a portion of the cross-sectional view of FIG. 20 enlarged;

FIG. 22 illustrates a perspective view of the bracelet of FIG. 1, attached to the wrist of a user, showing the connector band;

FIG. 23 is a front view of the connector band of FIG. 19, shown by itself, and with the electrical cables protruding therefrom;

FIG. 23A shows a table of lengths for the connector band of FIG. 23;

FIG. 24 is a cross-sectional view through the connector band of FIG. 23;

FIG. 28 D is a view showing a table of palm distances for the $25^{th}$, the $50^{th}$, and the $95^{th}$ percentile male and female;

FIG. 29 illustrates a cross-sectional view of a person's hand, showing the wrist thickness and wrist circumference;

FIG. 29A is a view showing a table of wrist thicknesses for the $25^{th}$, the $50^{th}$, and the $95^{th}$ percentile male and female;

FIG. 29B is a view showing a table of wrist circumferences for the $25^{th}$, the $50^{th}$, and the $95^{th}$ percentile male and female;

FIG. 29C is a view showing a table of band length analyses for the $95^{th}$, the $50^{th}$, and the $95^{th}$ percentile male and female;

FIG. 30 illustrates a cross-sectional view of a person's hand, showing tendons and nerves therein, and also showing the radial and ulnar arteries;

FIG. 46 is a view showing a table comparing window attributes for various different materials that may be used for the window of the first and second treatment modules;

FIG. 49 is a chart showing budgeting of power from the battery to each of the light sources of both the first and second treatment modules for the positioning shown in FIGS. 32 and 36;

FIG. 50 is a chart showing budgeting of power from the battery to each of the light sources of both the first and second treatment modules for the positioning shown in FIGS. 38 and 42;

FIG. 70 is a top level dashboard screen that may be reached by toggling the three parallel lines at the top left side of the screen of FIG. 56, and which may provide the user with additional options;

FIG. 71 depicts a table of data for programmable parameters for the treatments modules of the present invention;

FIG. 72 depicts a table of data for treatment protocols that may be used by the present invention.

DETAILED DESCRIPTION OF THE INVENTION

Figure 1:
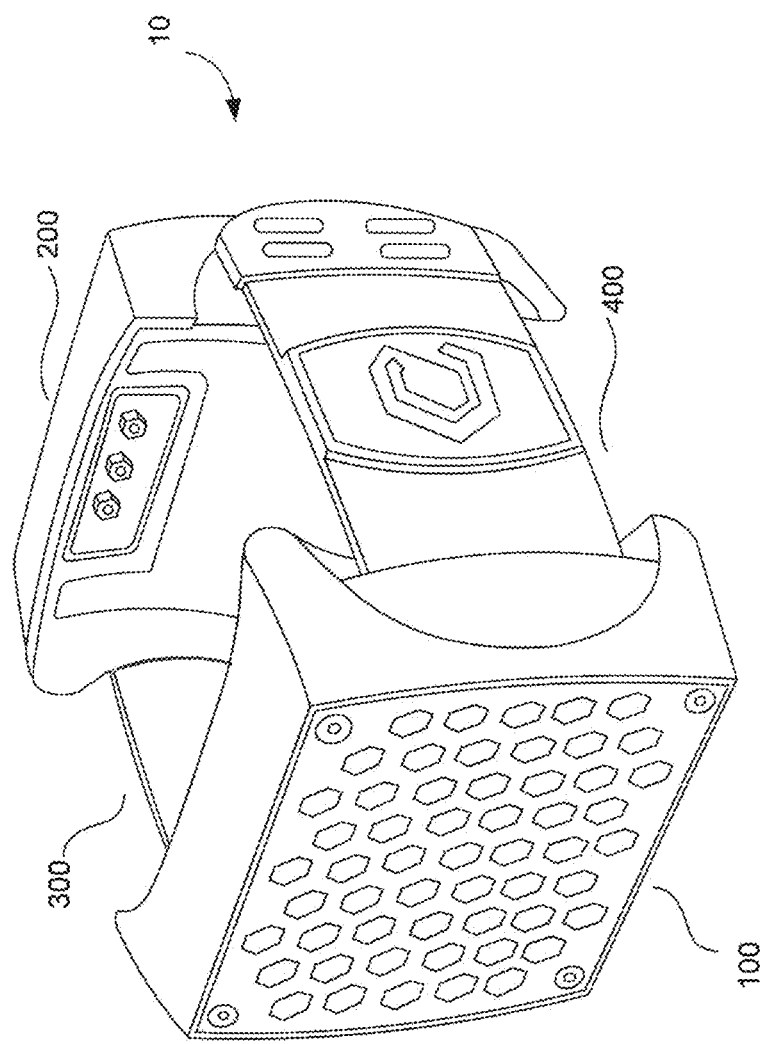
FIG. 1 illustrates a first perspective view of the bracelet of the present invention, being configured with a first treatment module for therapeutic blood irradiation directed at least to a first wrist region of a user, a second treatment module for additional targeted blood irradiation and for body temperature regulation at a second wrist region of the user.
Figure 2:
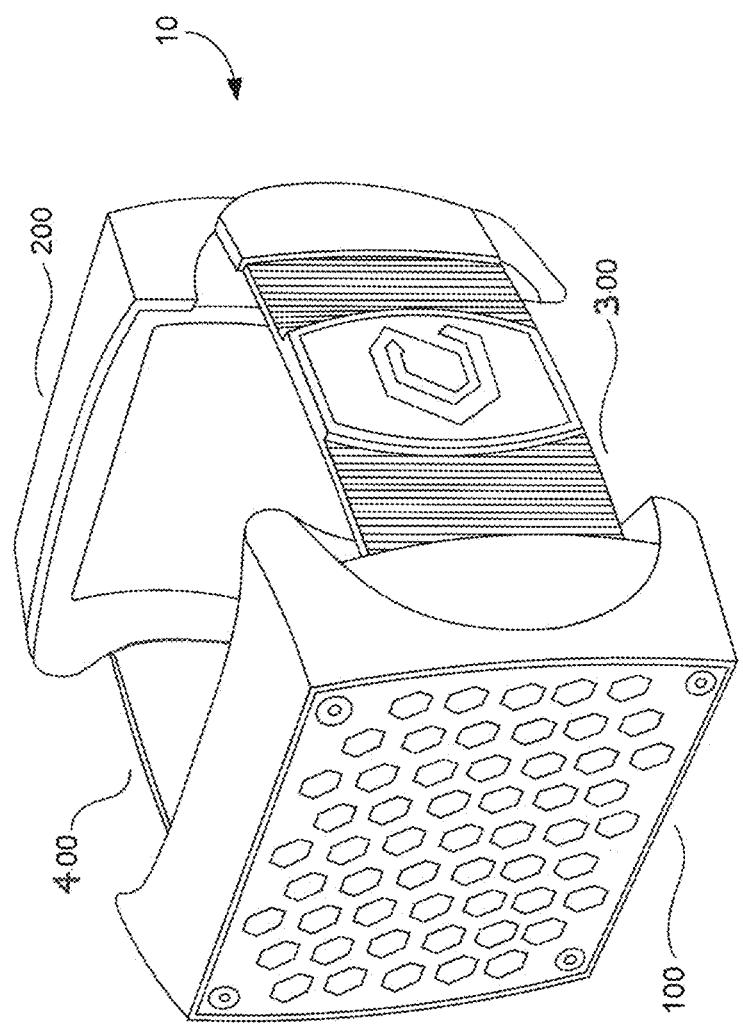
FIG. 2 illustrates a second perspective view of the bracelet of FIG. 1.
Figure 3:
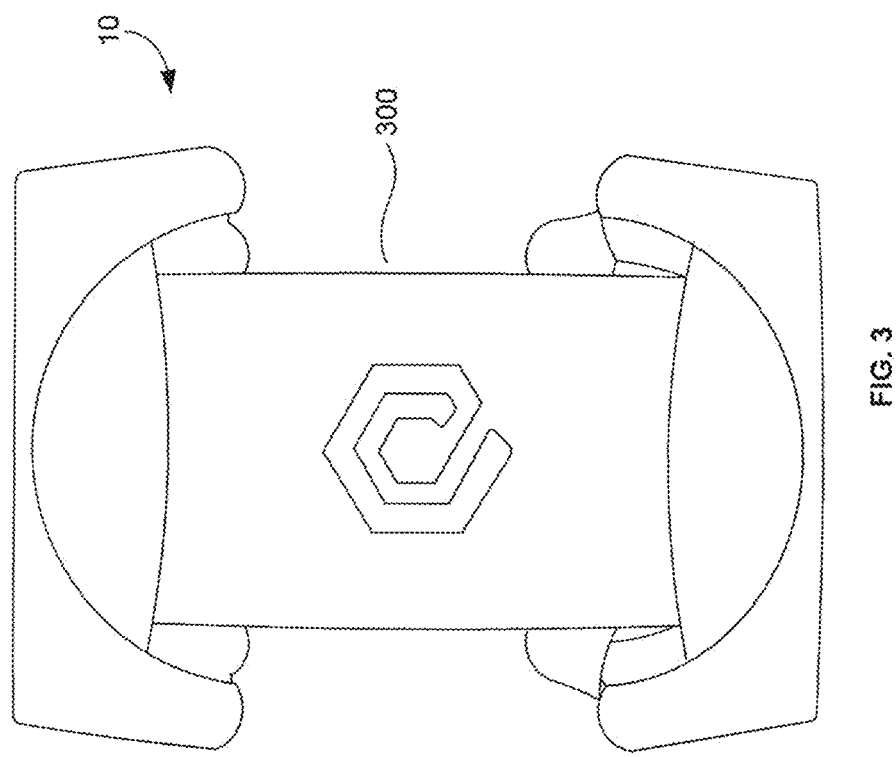
FIG. 3 illustrates a view showing the connector band of the bracelet of FIG. 1, connecting the first and second treatment modules.
Figure 6:
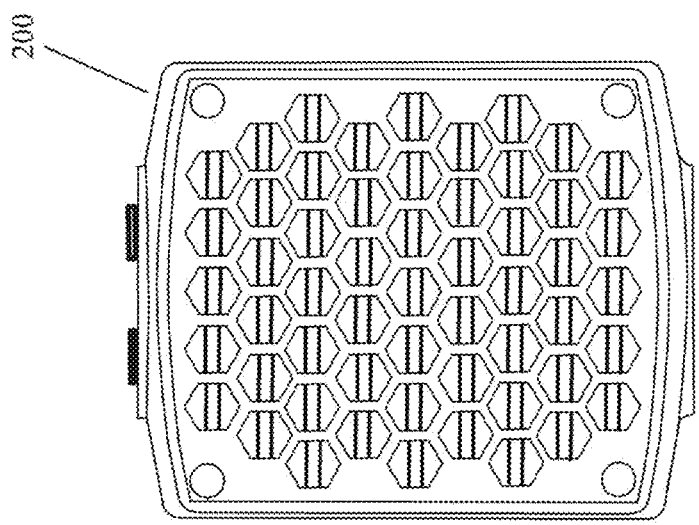
FIG. 6 illustrates a front view of the second treatment module of the bracelet of FIG. 1.
Figure 5:
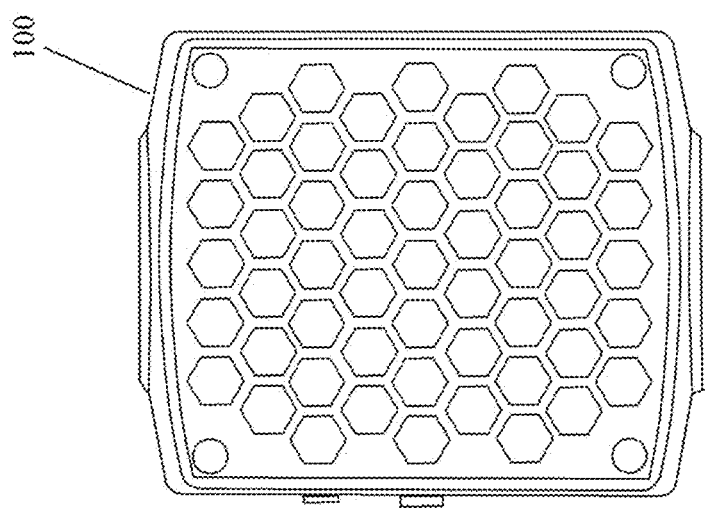
FIG. 5 illustrates a front view of the first treatment module of the bracelet of FIG. 1.

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C", and "A, B, and/or C" mean all of the following possible combinations: A alone; or B alone; or C alone; or A and B together; or A and C together; or B and C together; or A, B and C together.

Also, all references (e.g., patents, patent publications, and non-patent literature) that are cited within this documents are incorporated herein in their entirety by reference.

Furthermore, the described features, advantages, and characteristics of any particular embodiment disclosed in this specification, may be combined in any suitable manner with any of the other embodiments disclosed herein.

In accordance with one embodiment, a bracelet of the present invention may be configured for therapeutic blood irradiation at a first wrist region of the user using a first treatment module, and for additional therapeutic blood irradiation at a second wrist region of a user using a second treatment module. In another embodiment, the bracelet may be configured for therapeutic blood irradiation at the first wrist region using the first treatment module, and for body temperature regulation at the second wrist region using the second treatment module. In yet another embodiment, the bracelet may be configured for therapeutic blood irradiation at the first wrist region using the first treatment module, and for additional therapeutic blood irradiation and body temperature regulation at the second wrist region using the second treatment module.

Other embodiment presented herein include:
a. First and second therapeutic module present in a common housing;
b. A single therapeutic module having due functions of light irradiation and body temperature regulation;
c. A flexible member, such as a band, that has regions of the flexible member that are light irradiating and regions that are body temperature regulating.
d. A single module blood irradiation embodiment;
e. A single module body temperature embodiment.

As shown in FIGS. 1-7, a connector band 300 of bracelet 10 may flexibly couple the first treatment module 100 to the second treatment module 200, for suitable positioning of the modules on the wearer's wrist, and a flexible attachment band 400 may have a first end be fixedly secured to the first treatment module, and may be configured for a portion thereof to be releasably coupled to the second treatment module, so that the user may attach the bracelet to his/her wrist. In another embodiment, a single band (i.e., a substrate) may be used, which may have a suitable opening formed therein to receive one treatment module. In yet another embodiment, the single band/substrate may be formed with two suitable openings to respectively receive each of the first and second treatment modules therein.

Figure 9A:
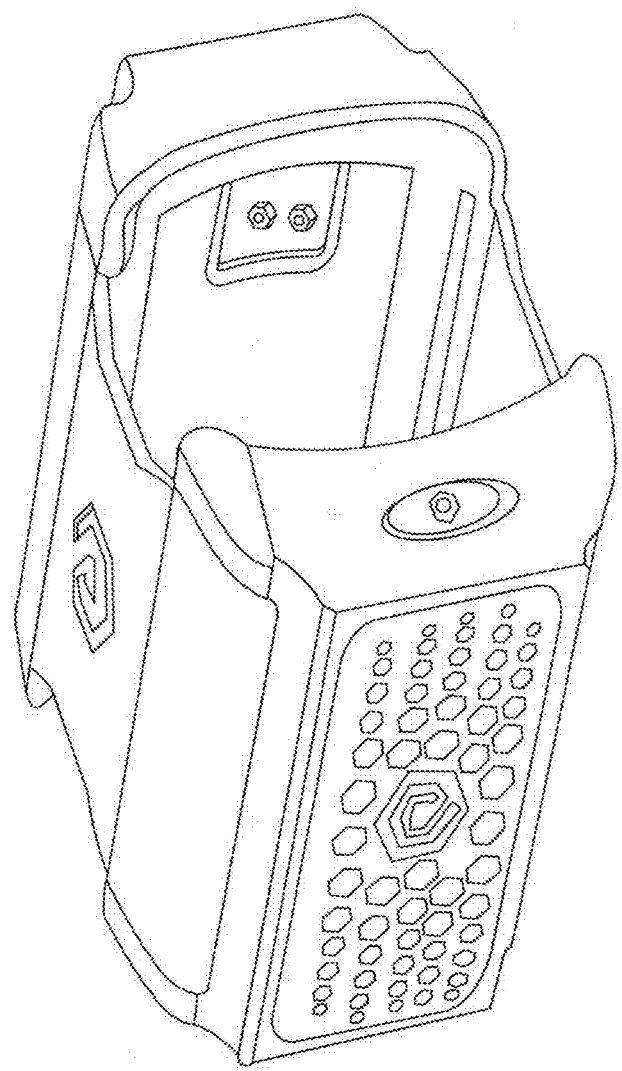
FIG. 9A illustrates an alternate embodiment of the device of FIG. 1.
Figure 9B:
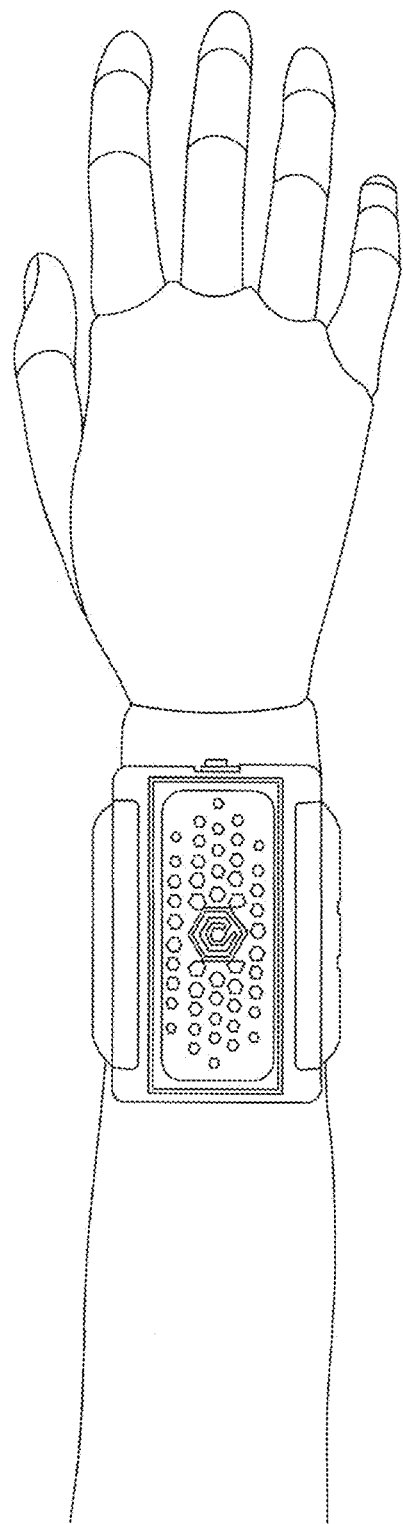
FIG. 9B illustrates a view of the bracelet of FIG. 9A attached to a user's wrist, showing the first treatment module in contact with the posterior (dorsal) aspect of the wearer's wrist.

FIGS. 8 and 9 show the bracelet 10 releasably secured to the wrist of a user, such that the treatment side of the first treatment module 100 may be positioned against the posterior (dorsal) aspect of the wearer's wrist, and to have the treatment side of the thermal module positioned against the anterior (ventral) aspect of the wearer's wrist. One reason for such positioning is that the major arterial vessels are more proximal to the surface of the skin below the ventral side of the wrist; therefore, heat removal to regulate body temperature may be more advantageously effected close to those vessels.

Figures 10, 11:
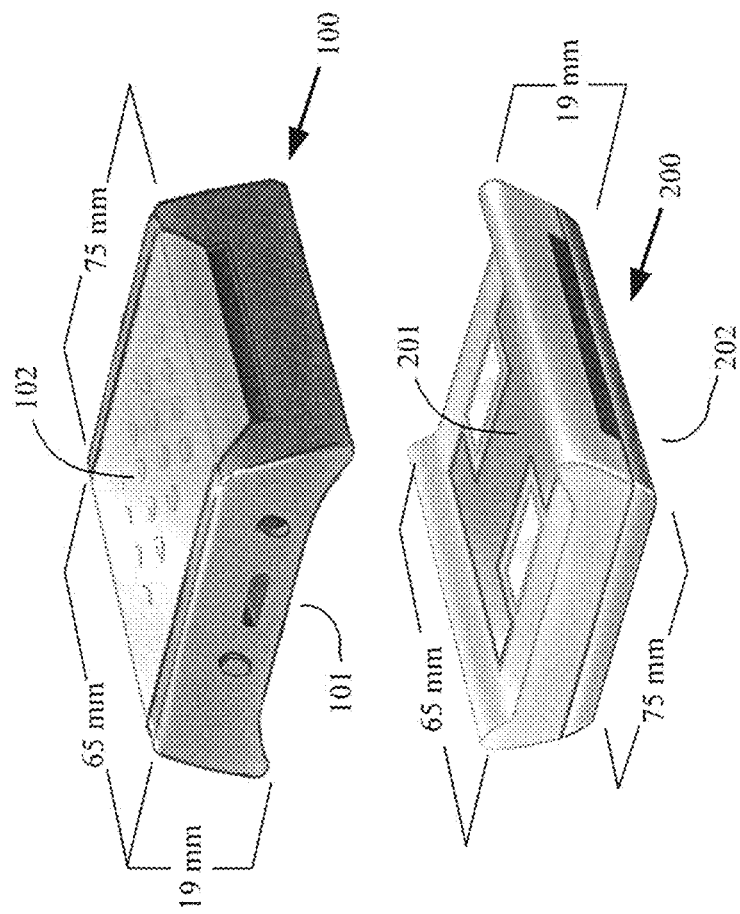
FIG. 10 illustrates a perspective view of the first treatment module, showing rough dimensions of a first embodiment of the module.
FIG. 11 illustrates a perspective view of the second treatment module, showing rough dimensions of a first embodiment of the module.

As seen in FIG. 10, the first side 101 (i.e., the treatment side) of the first treatment module 100 may have a contoured surface that may be roughly configured to conform to and wrap partially around the posterior (dorsal) aspect of the wearer's wrist. As seen in FIG. 11, the first side 201 (i.e., the treatment side) of the second treatment module 200 may have a contoured surface that may be roughly configured to conform to and wrap partially around the anterior (ventral) aspect of the wearer's wrist.

Figure 12:
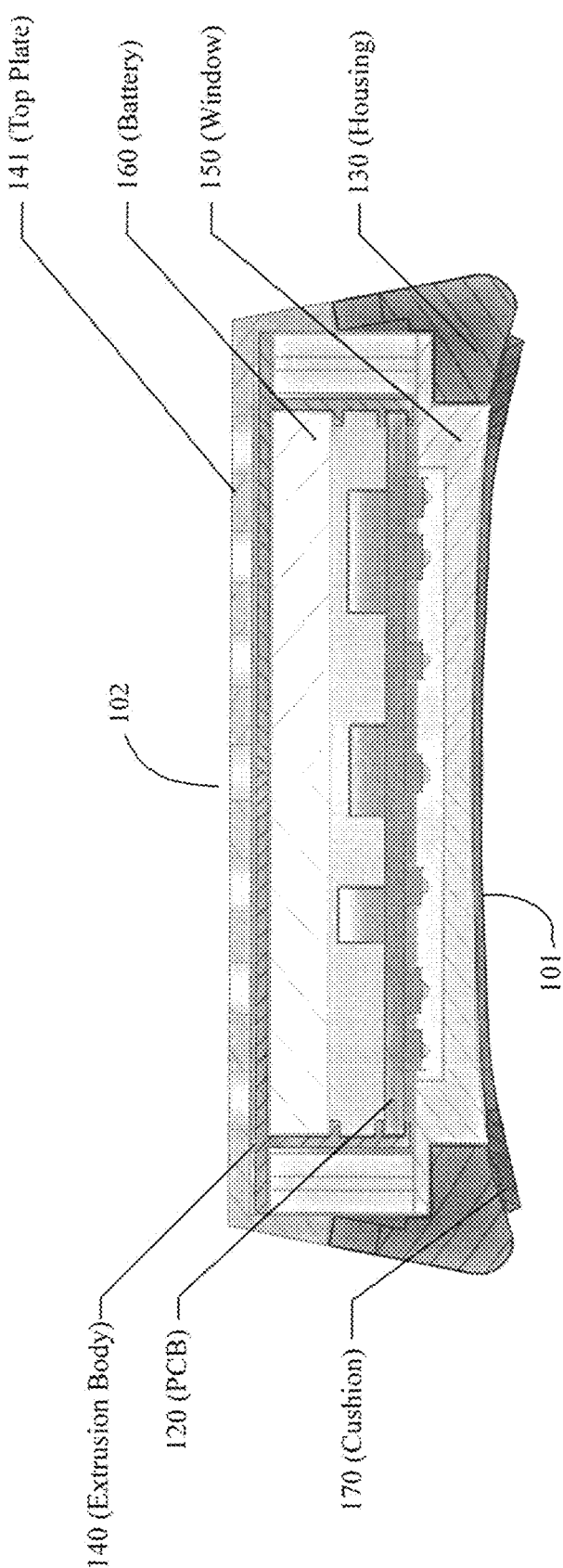
FIG. 12 is a cross-sectional view through the first treatment module.
Figure 25:
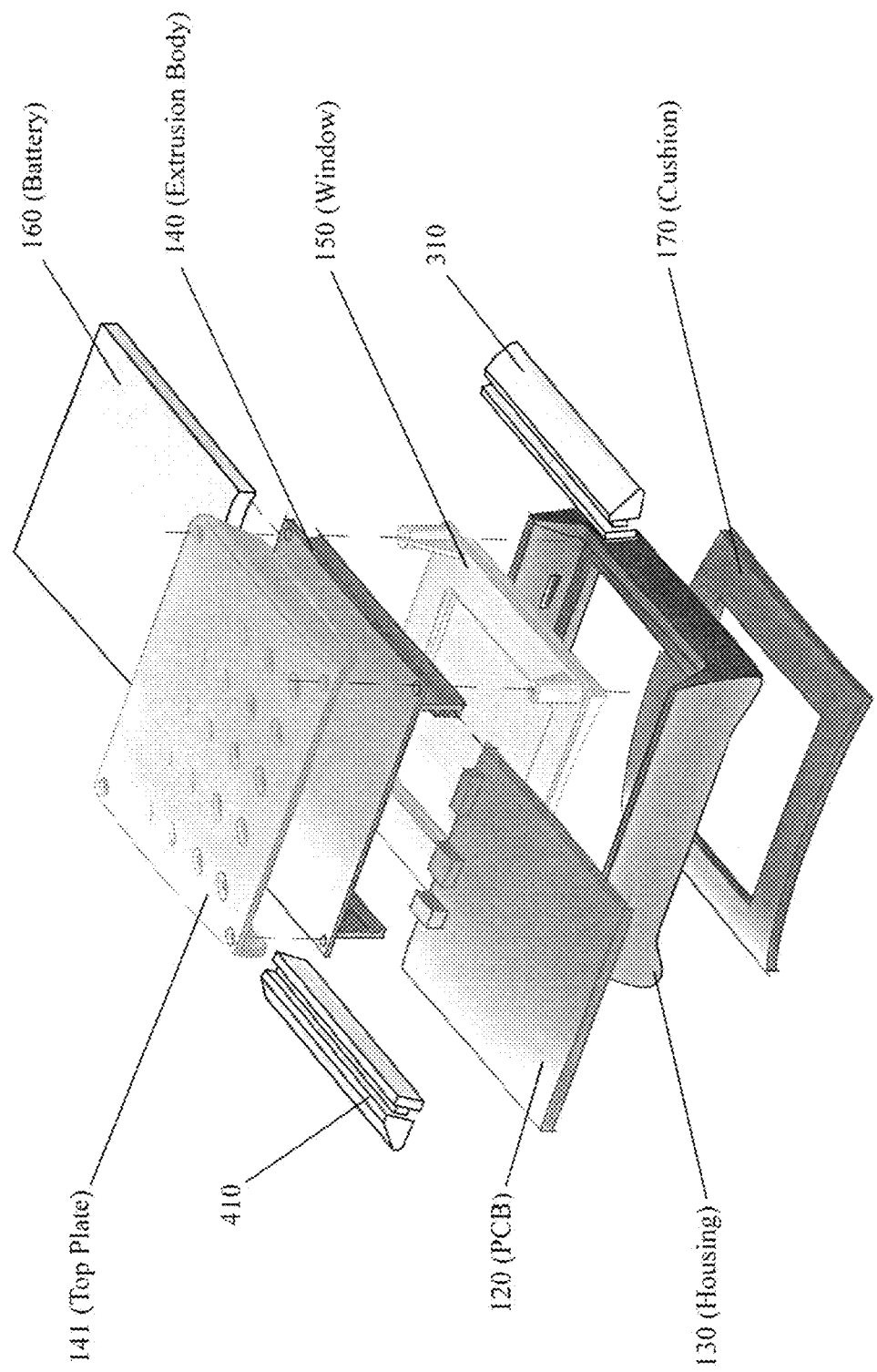
FIG. 25 is an exploded view illustrating the parts of the first module.

As seen in FIG. 12 (and the exploded view of FIG. 25), the first treatment module 100 may broadly include one or more light sources configured to emit one or more selective wavelengths of light from the first side 101 of the first treatment module. The one or more light sources may be configured to generate light at any wavelength within each of the ultraviolet, the visible, and the infrared spectrums (i.e., the one or more light sources can generate an unlimited number of wavelengths). In one embodiment, the one or more light sources may emit the selective wavelengths of light within the range of about 350 nm to about 1000 nm, and may preferably emit the selective wavelengths of light within the range of about 450 nm to about 850 nm. In one embodiment, the one or more light sources may more preferably emit wavelengths of light selected from: about 450 nm, about 532 nm, about 630 nm, about 660 nm, about 660 nm, and about 850 nm. Use within this specification of the relative term "about" in connection with a numeric value is intended to mean±20% of the stated numeric value; therefore the one or more light sources may emit wavelengths of light selected from: 450 nm±20 nm, 532 nm±20 nm, 630 nm±20 nm, 660 nm±20 nm, 660 nm±20 nm, and 850 nm±20 nm. In one embodiment, the one or more light sources may emit wavelengths of light at the wavelengths of 850 nm, 660 nm, 630 nm, 532 nm, and 450 nm. The one or more light sources that may emit the light at the 850 nm and the 660 nm wavelengths/ranges may use a total amount of power in the range of about 300 mW to about 500 mW, and may, in one embodiment, use a total of 415 mW. The one or more light sources that may emit the light at the 630 nm, the 532 nm, and the 450 nm wavelengths/ranges may use a total amount of power in the range of about 300 mW to about 500 mW, and may, in one embodiment, use a total of 335 mW.

In one embodiment, the RGB lighting provided by the range of wavelengths about 630 nm, 532 nm, and 450 nm may be replaced by light sources configured to emit only light at the green and blue wavelengths (i.e., the 532 nm, and 450 nm wavelengths/ranges), or the 630 nm wavelength light sources may instead be inactivated, if desired.

Figure 32:
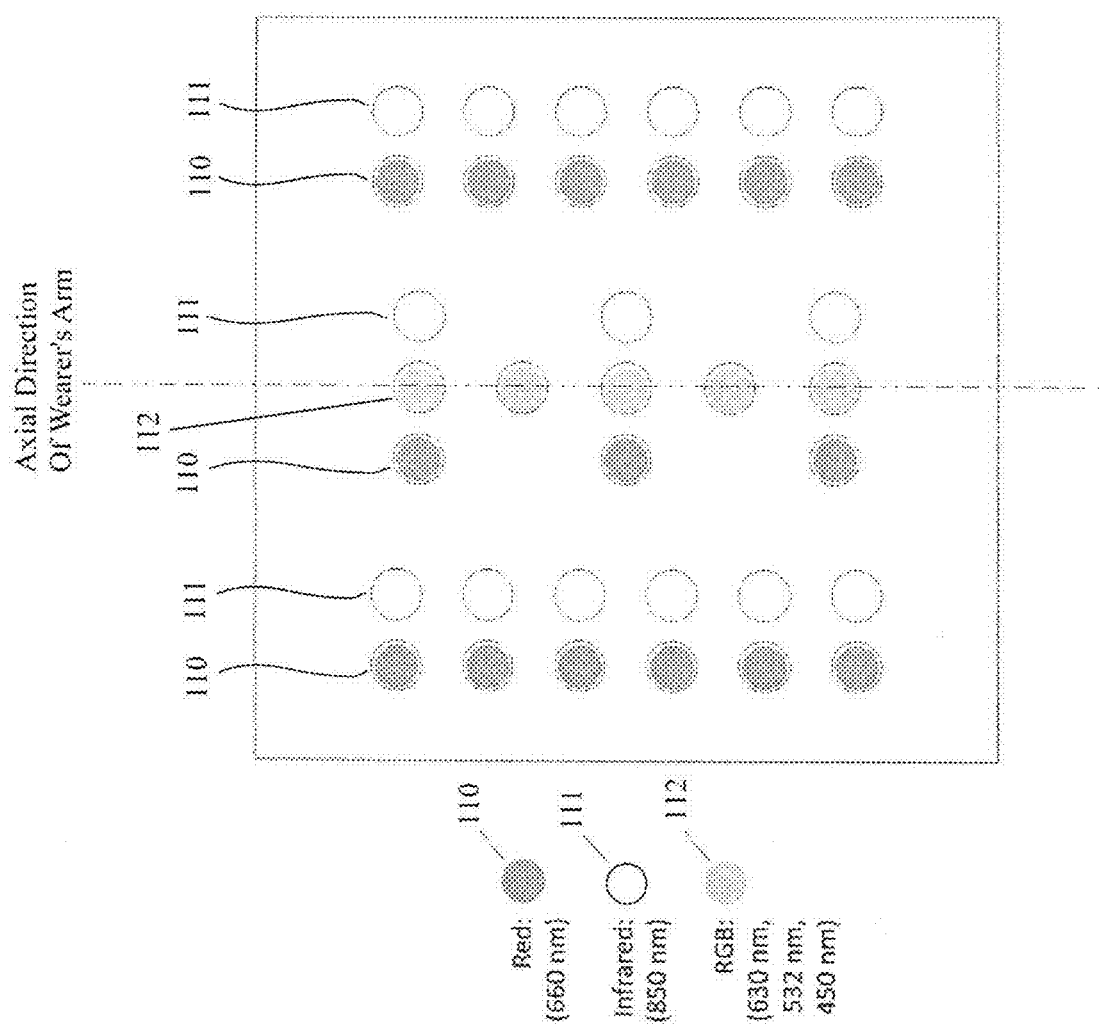
FIG. 32 is a view showing placement of the plurality of light sources in the first treatment module, including light sources selectively positioned to provide 660 nm wavelength/range and 880 nm wavelength/range through the device area, and 450, 532, and 630 nm wavelengths/ranges along central axial locations.

In one arrangement of the light sources for the first treatment module 100, shown in FIG. 32, there may be a plurality of light sources. In one embodiment of the invention, there may be five light sources 112 that may be positioned in a row that may be along the axis of the module that is to be aligned with the axis of the person's arm (i.e., being in a row oriented to be substantially perpendicular to the axial line 10X in FIG. 7 that is through the center of the connector band 300 and the attachment band 400). There may also be two rows of six light sources 110 and one row of three light sources 110, each row being similarly oriented, with each of the two rows of six lights 100 positioned distally from, and on opposite sides of, the row of five light sources 112, and with the row of three light sources 110 being positioned adjacent to one side of the row of five light sources 112. There may also be two rows of six light sources 111 and one row of three light sources 111, each being similarly oriented, but symmetrically positioned, as seen in FIG. 32. It will be appreciated that other light arrangements are possible with the scope of the present invention. For example the alignment of the lights may be rotated from 0 to 180 degrees in either direction about the person's arm.

Figure 33:
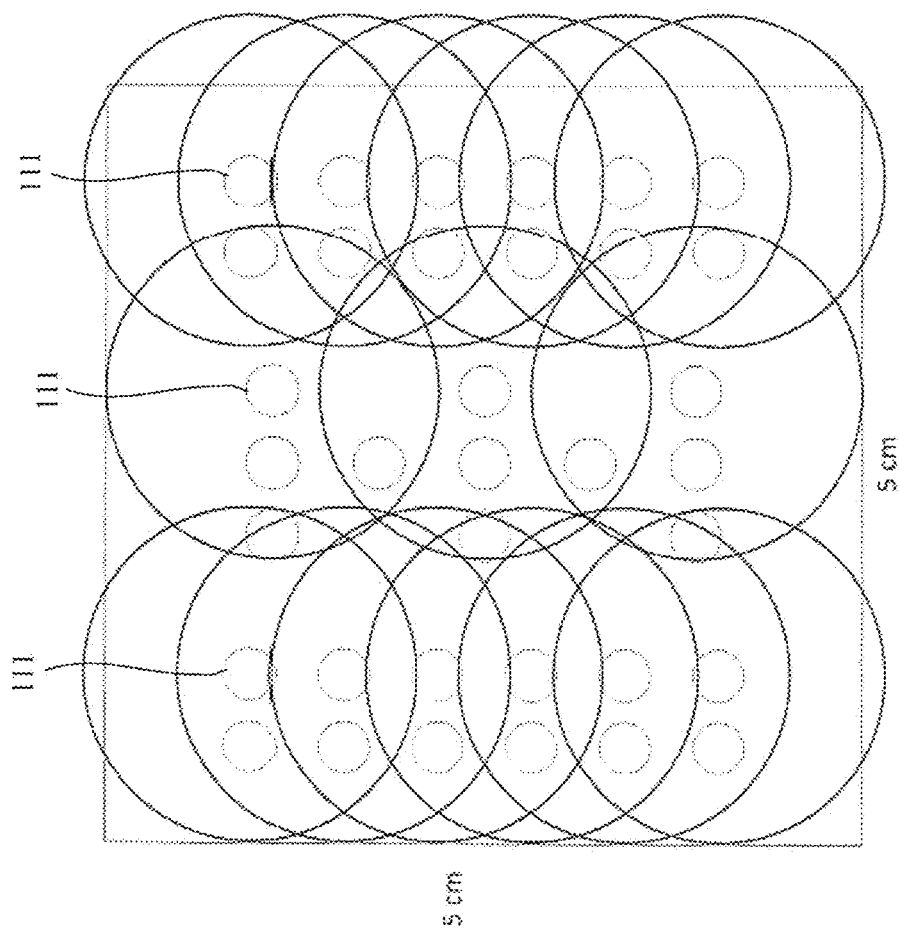
FIG. 33 is a view illustrating the percentage of coverage within a 25 cm square area provided by the light sources in the first module that are configured to emit the 850 nm wavelength/range.
Figure 34:
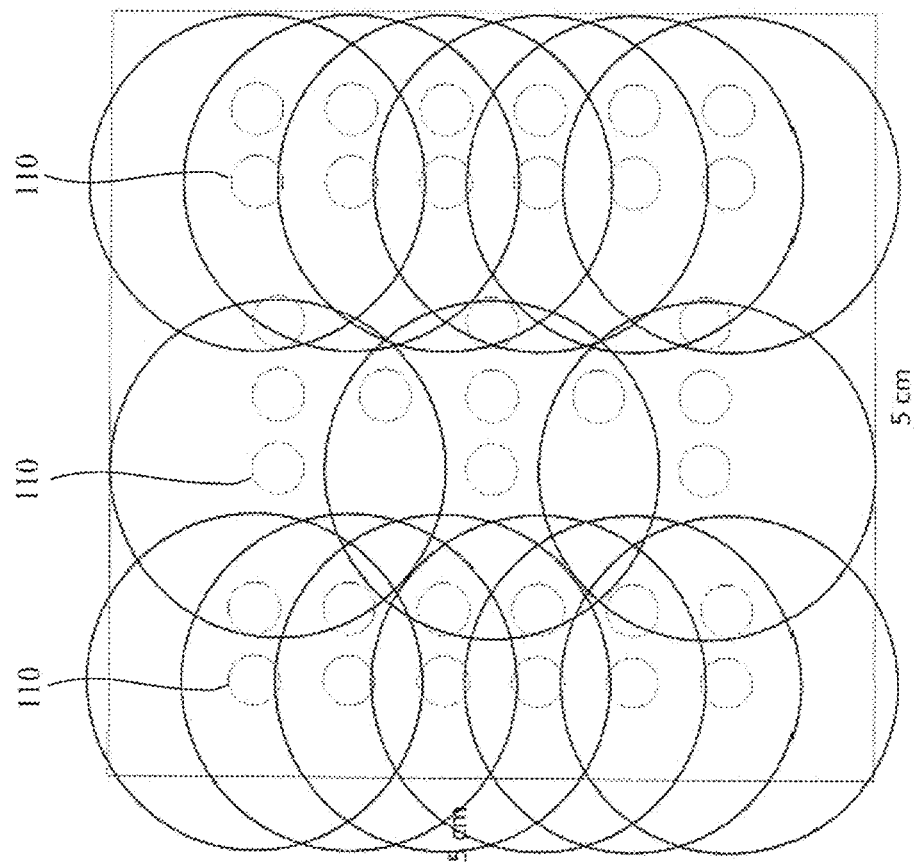
FIG. 34 is a view illustrating the percentage of coverage within a 25 cm square area provided by the light sources in the first module that are configured to emit the 660 nm wavelength/range.

As seen in FIGS. 33-34, the described positioning of the light sources 110 and 111 for the first treatment module 100 may serve to provide coverage of those wavelengths over a substantial portion of the treatment area of the arm. In one example, a 25 square centimeter area may be used. This can vary if desired by patient size and for other reasons as well. Preferably there is about 95% coverage or greater of the treatment area. Tests have shown efficacy of those wavelengths being distributed to the circulating blood at a suitable power density, which is arrived at using the power levels and pulsing provided herein over the 25 square centimeter area.

Figure 35:
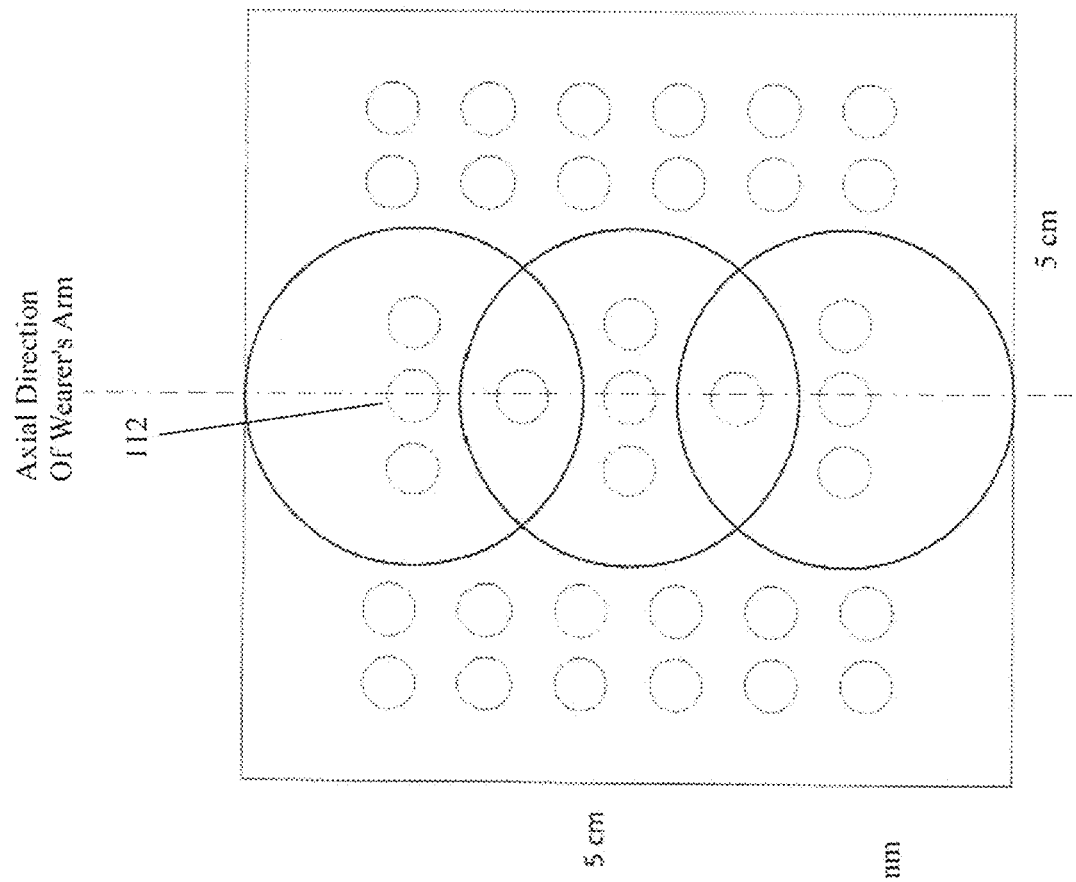
FIG. 35 is a view illustrating the axial coverage within the 25 cm square area provided by the light sources in the first module that are configured to emit the 450, 532, and 631 nm wavelengths/ranges.
Figure 38:
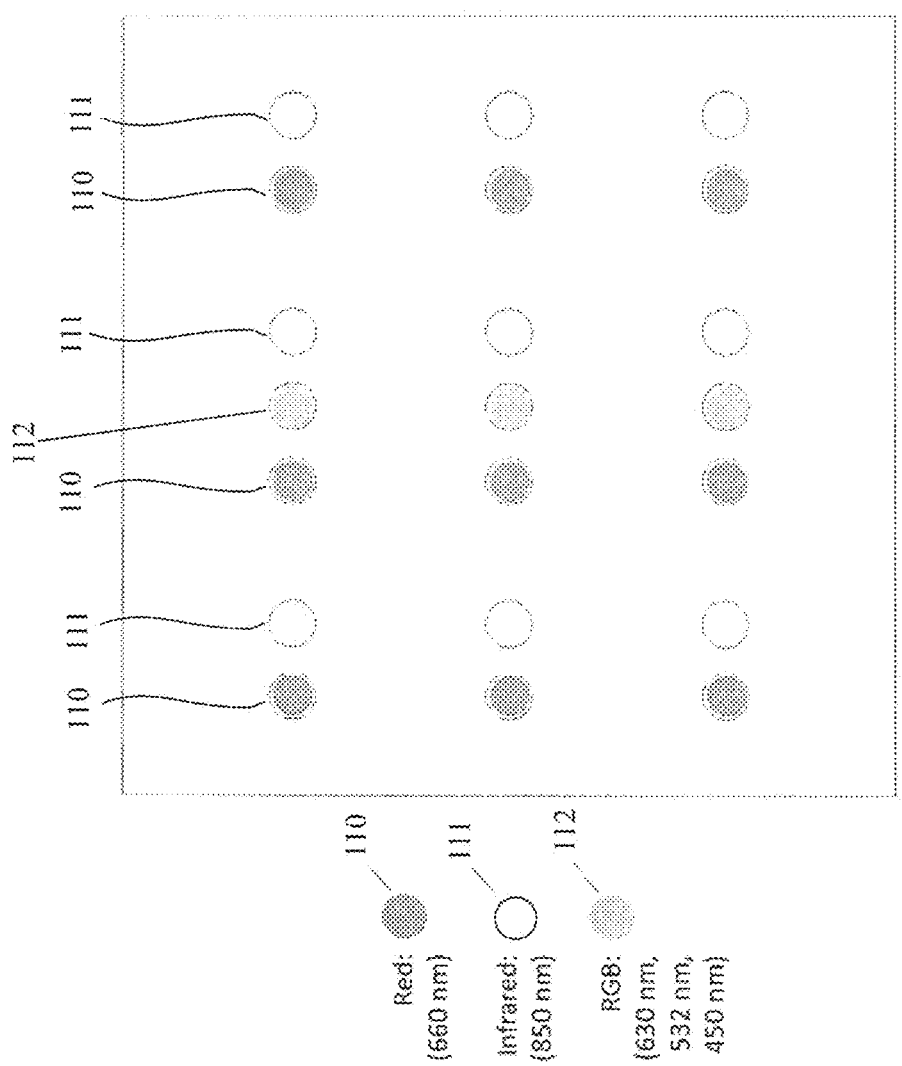
FIG. 38 is a view alternative showing placement of the plurality of light sources in the first treatment module, as an alternative to the placement shown within FIG. 32.
Figure 39:
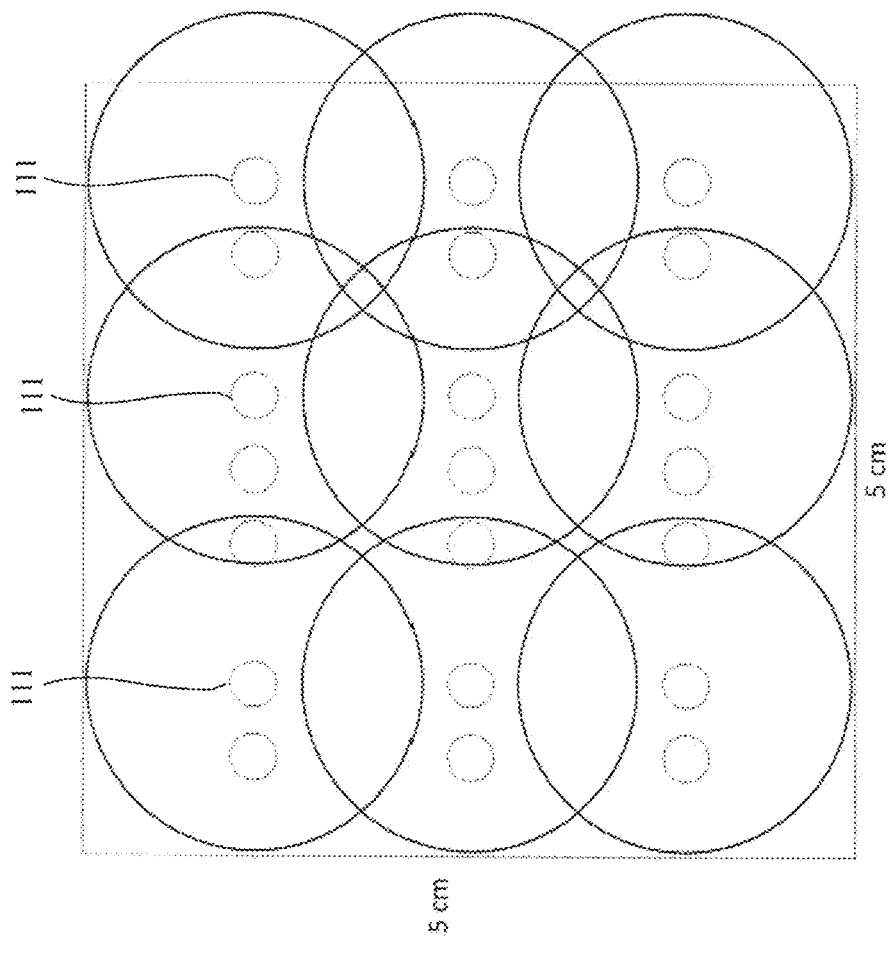
FIG. 39 is a view illustrating the percentage of coverage within a 25 cm square area provided by the 850 nm light sources in the first module, when positioned as shown in FIG. 38.
Figure 40:
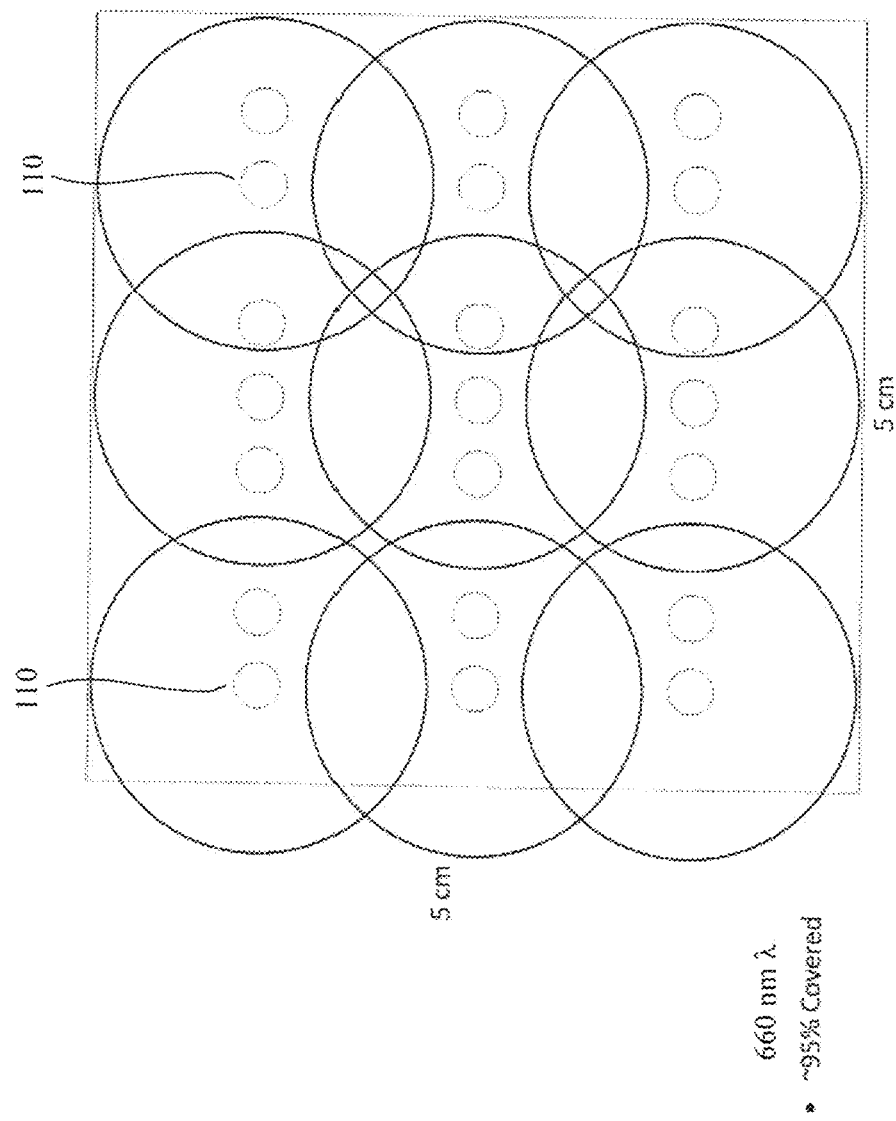
FIG. 40 is a view illustrating the percentage of coverage within an area provided by the 660 nm light sources in the first mobile, which may be rectangular or square shaped, when positioned as shown in FIG. 38.
Figure 41:
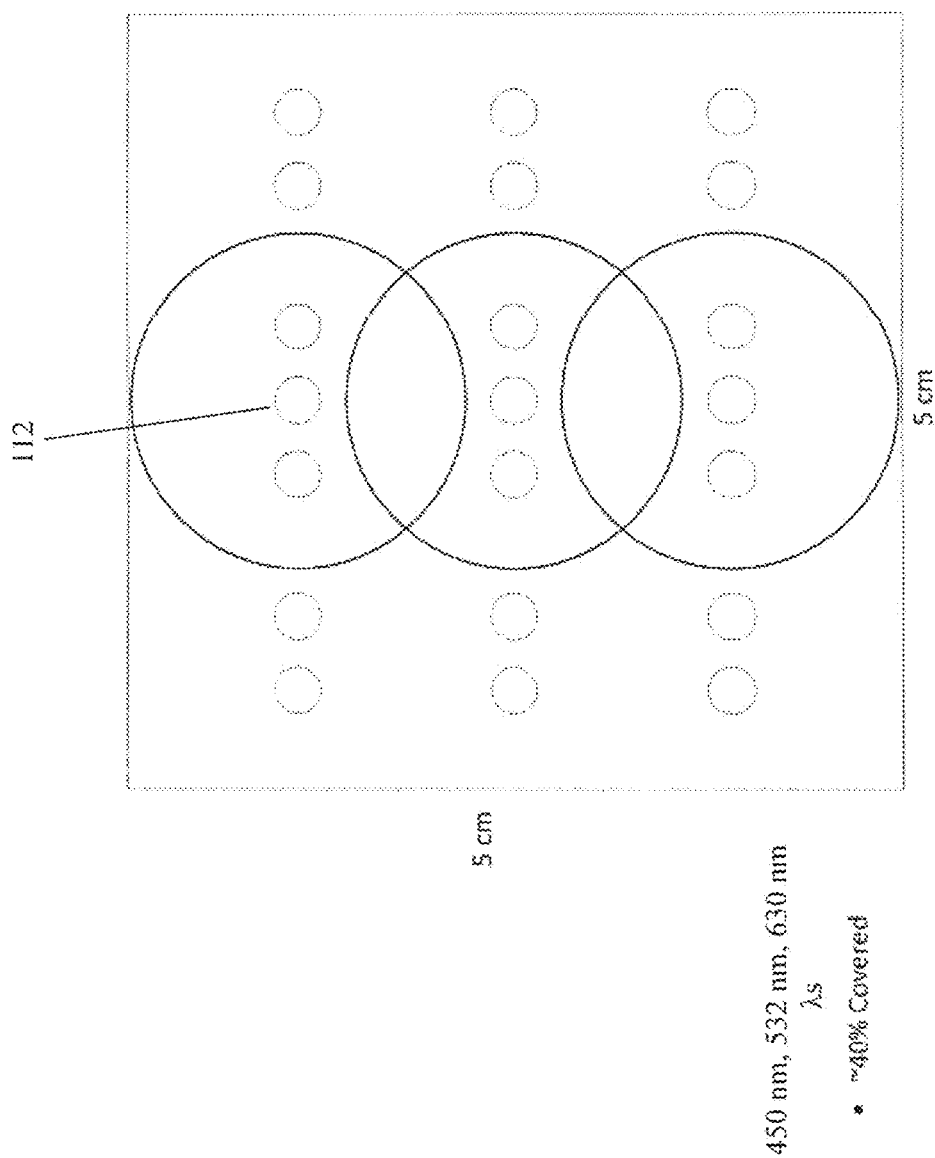
FIG. 41 is a view illustrating the axial coverage within the 25 cm square area provided by the light sources in the first module, as positioned in FIG. 38, which light sources are configured to emit the 450, 532, and 631 nm wavelengths/ranges.
Figure 42:
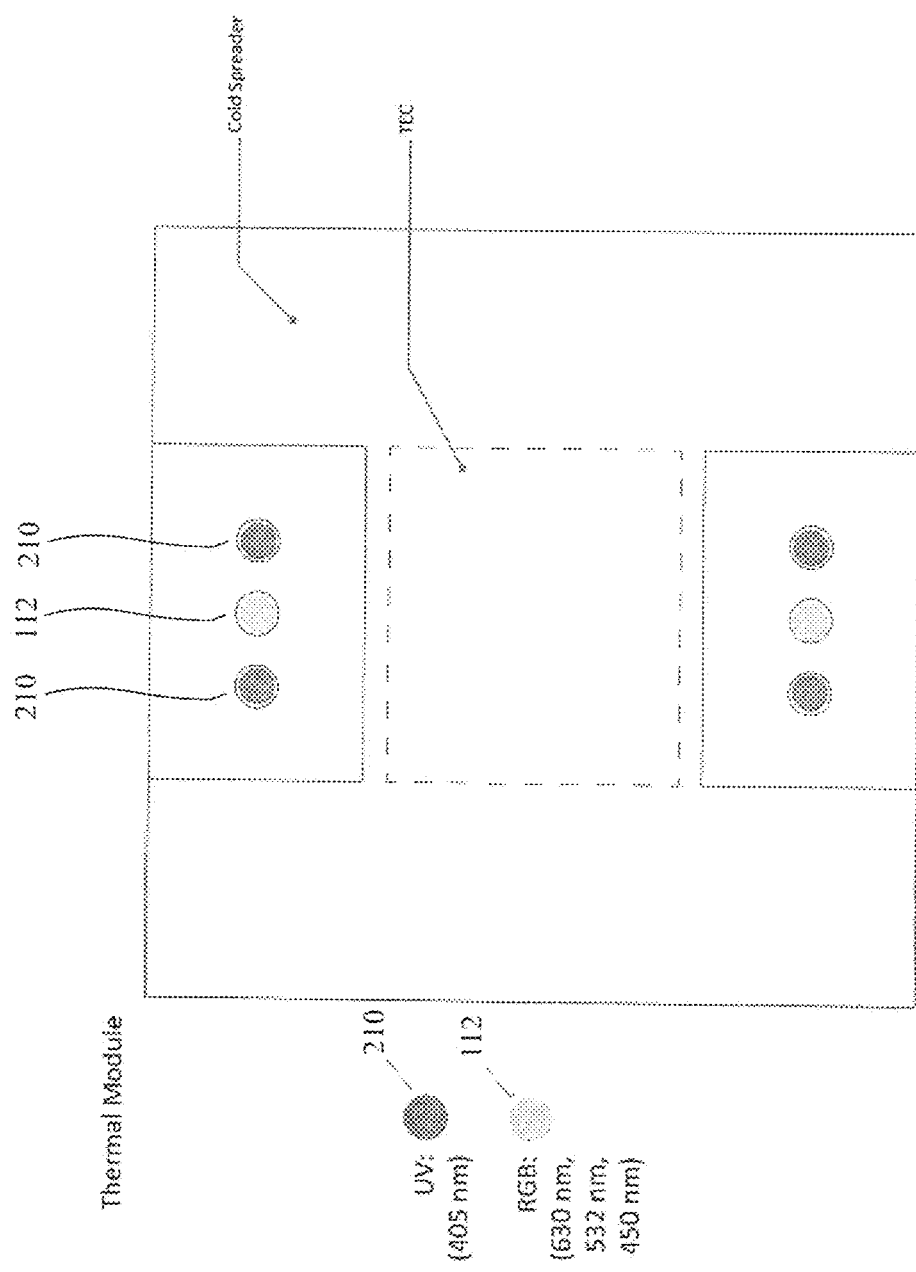
FIG. 42 is a view showing placement of the plurality of light sources in the second treatment module, as an alternative to the placement shown within FIG. 36.
Figure 43:
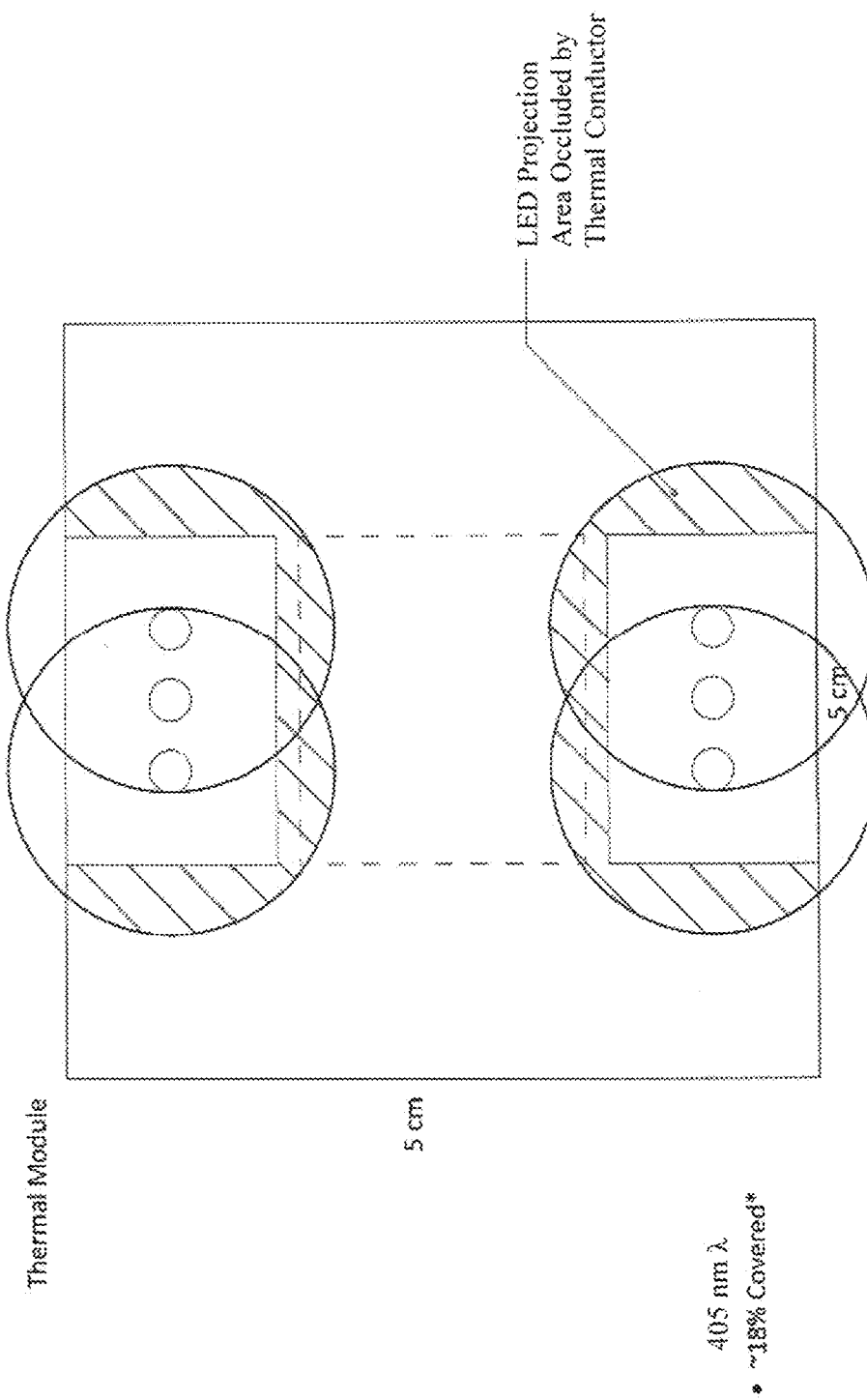
FIG. 43 is a view showing that selective placement of the plurality of light sources in the second treatment module provides 405 nm wavelength irradiation directed roughly towards each of the radial and ulnar arteries in the wrist.
Figure 44:
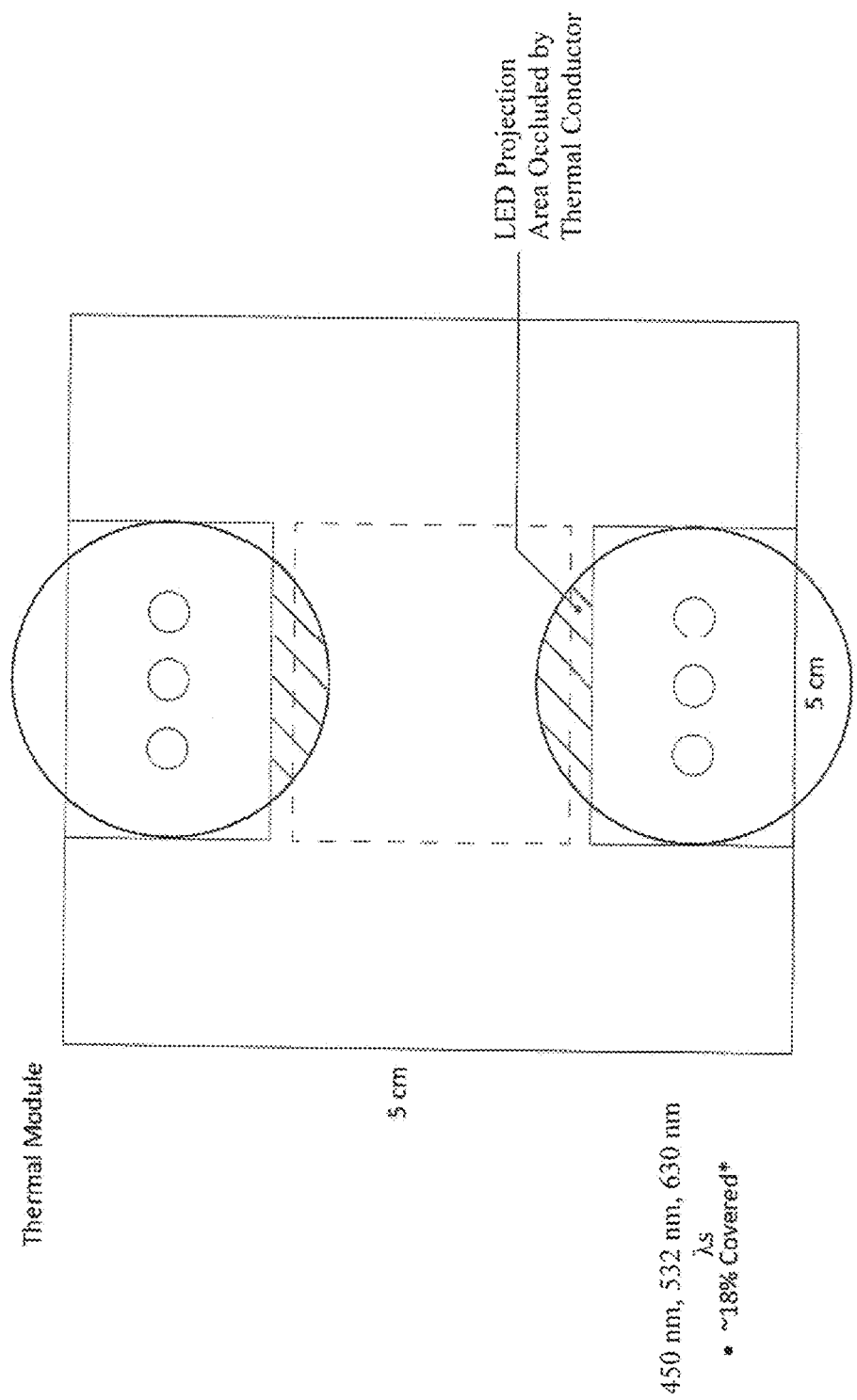
FIG. 44 is a view illustrating the aligned axial coverage within the 25 cm square area provided by the light sources in the second module, as positioned in FIG. 42, which are configured to emit the 450, 532, and 631 nm wavelengths/ranges.
Figure 45:
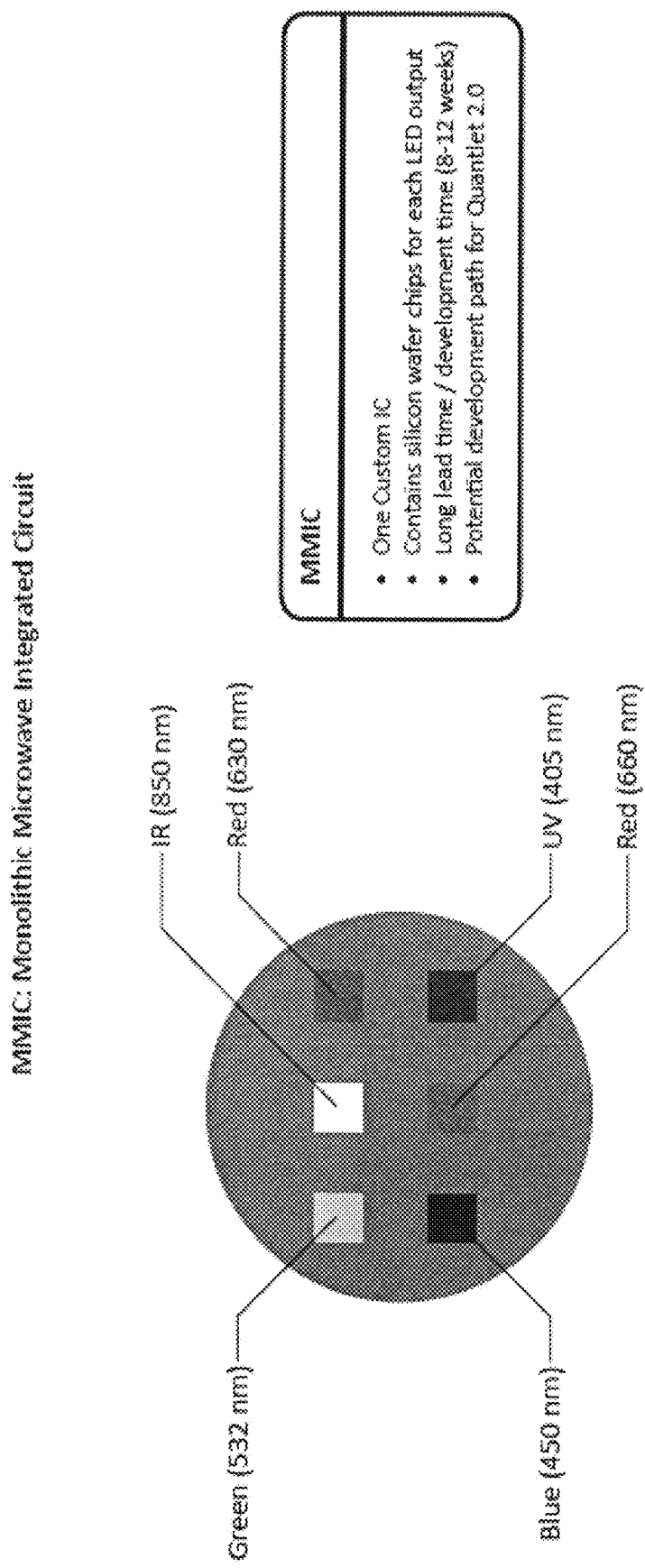
FIG. 45 is a view illustrating a monolithic microwave integrated circuit with light sources positioned thereon, which may be used in an alternative embodiment.

As seen in FIG. 35, the positioning of the light sources 112 may serve to distribute those wavelengths over the central (axial) portion of the user's wrist. The central positioning for the 532 nm and 450 nm wavelengths/ranges allow for a higher impact to blood in the capillaries near the epidermis/skin surface. Those are found throughout, and by centrally locating those light sources, more scattering of those wavelengths of light from tissue may occur. (Note, an alternate embodiment with alternative positioning and quantities of light sources is shown in FIG. 38, which is comparable, but uses fewer light sources).

Figure 13:
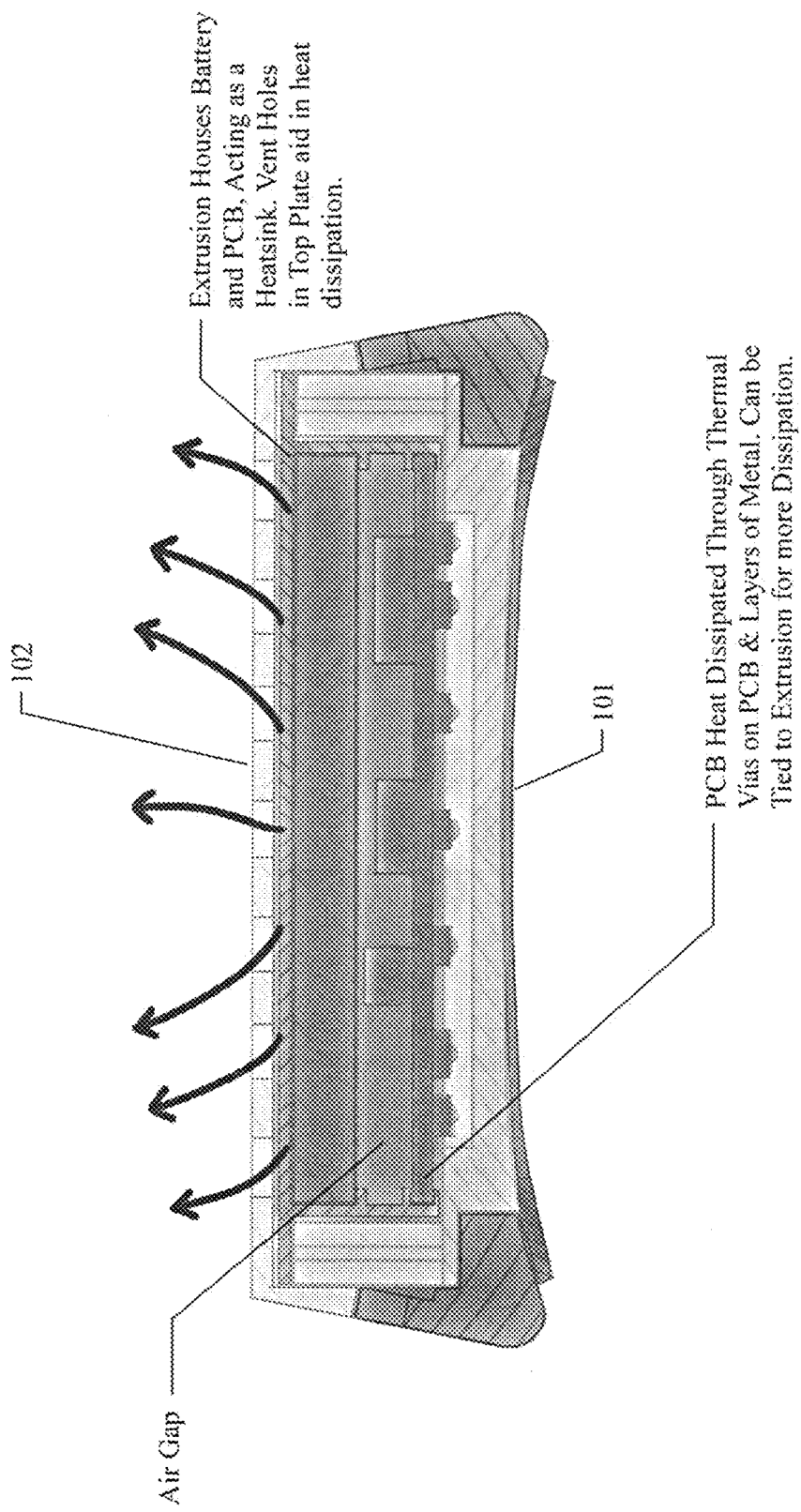
FIG. 13 is the cross-sectional view of FIG. 12, showing the heat dissipation from the light sources away from a second side of the module.
Figure 47:
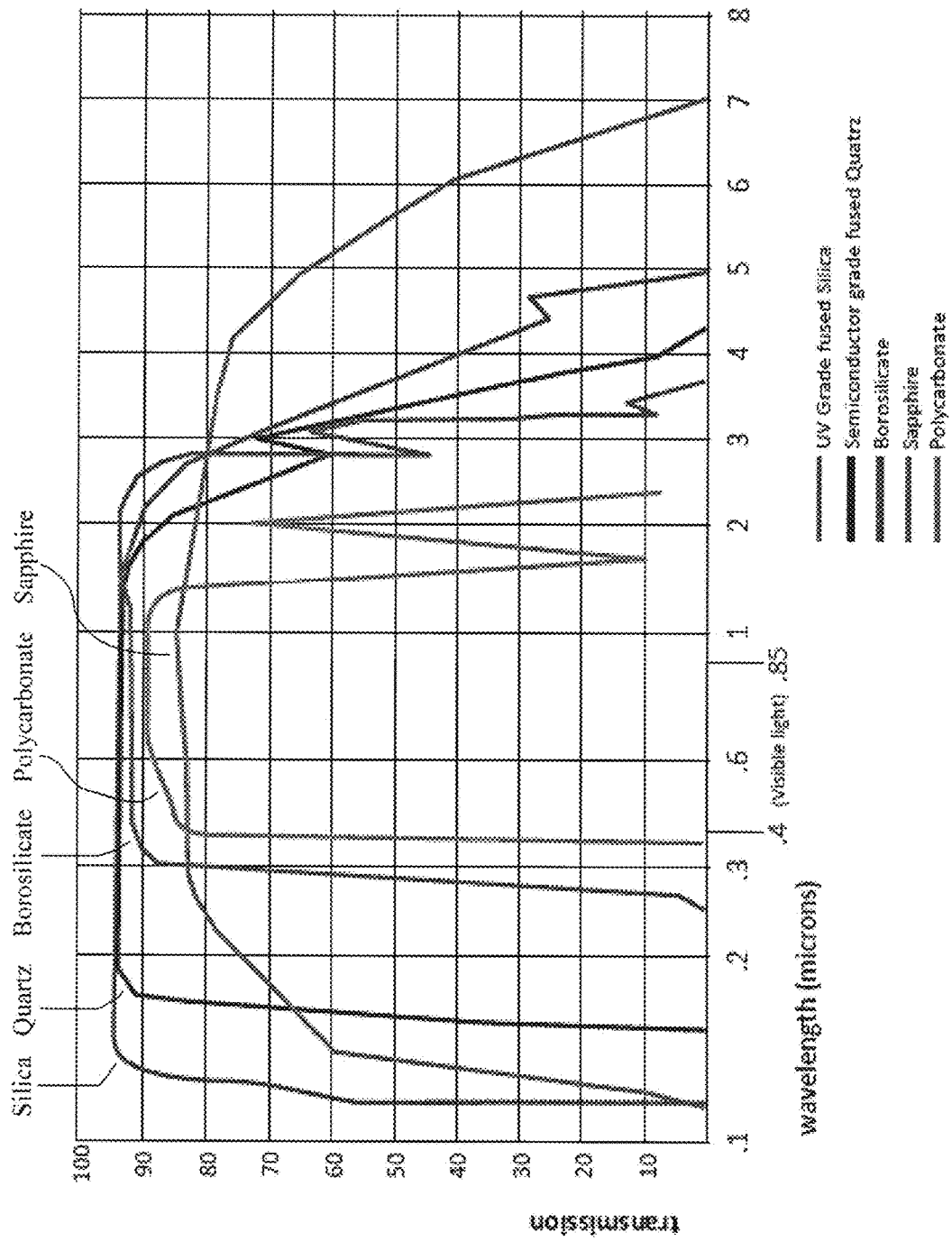
FIG. 47 is a graph showing the transmissivity of visible light through various different materials that may be used for the window of the first and second treatment modules.
Figure 48:
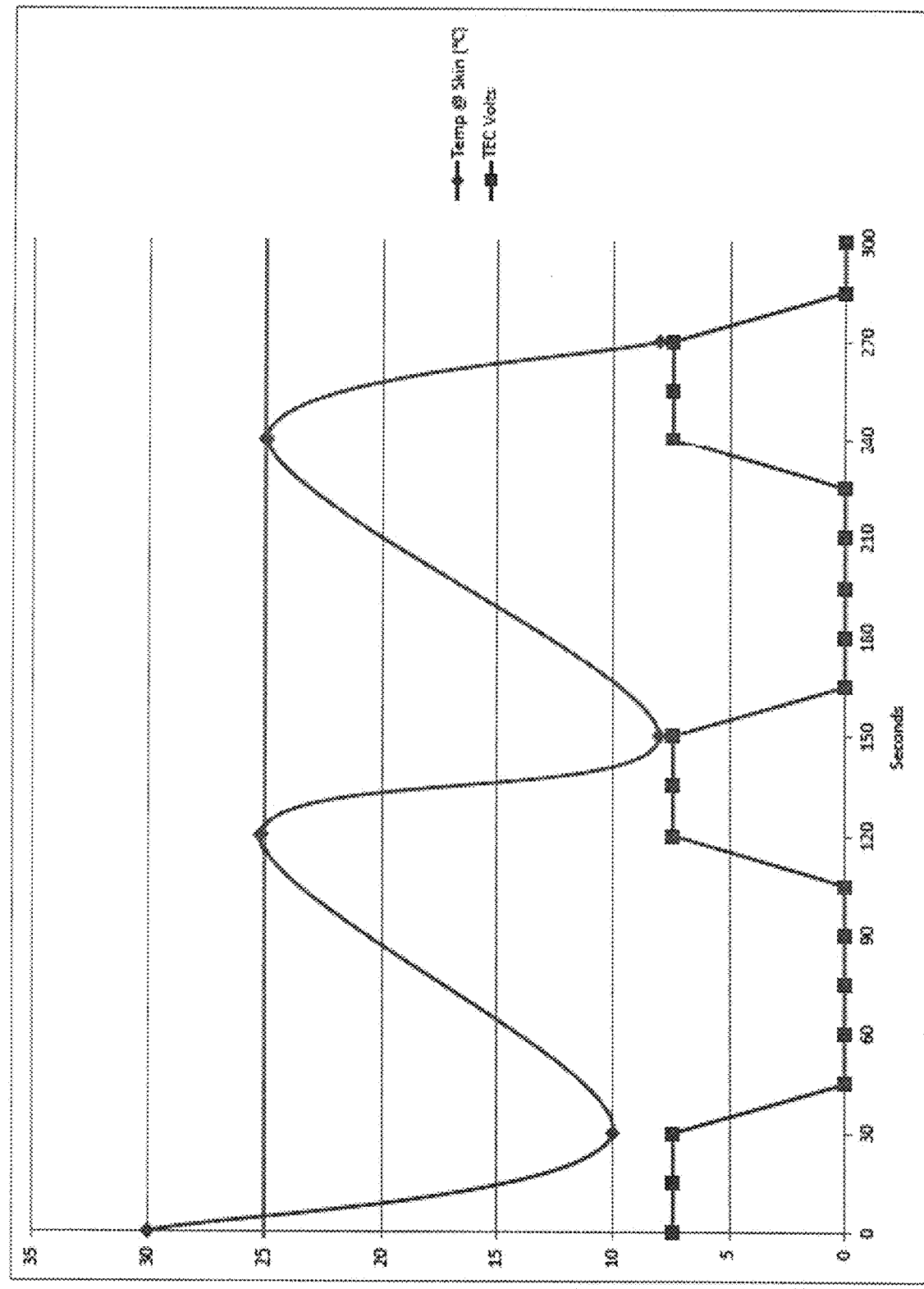
FIG. 48 is a graph showing the relationship between skin temperature and voltage supplied to the cooling unit by the battery for the second treatment module.
Figure 51:
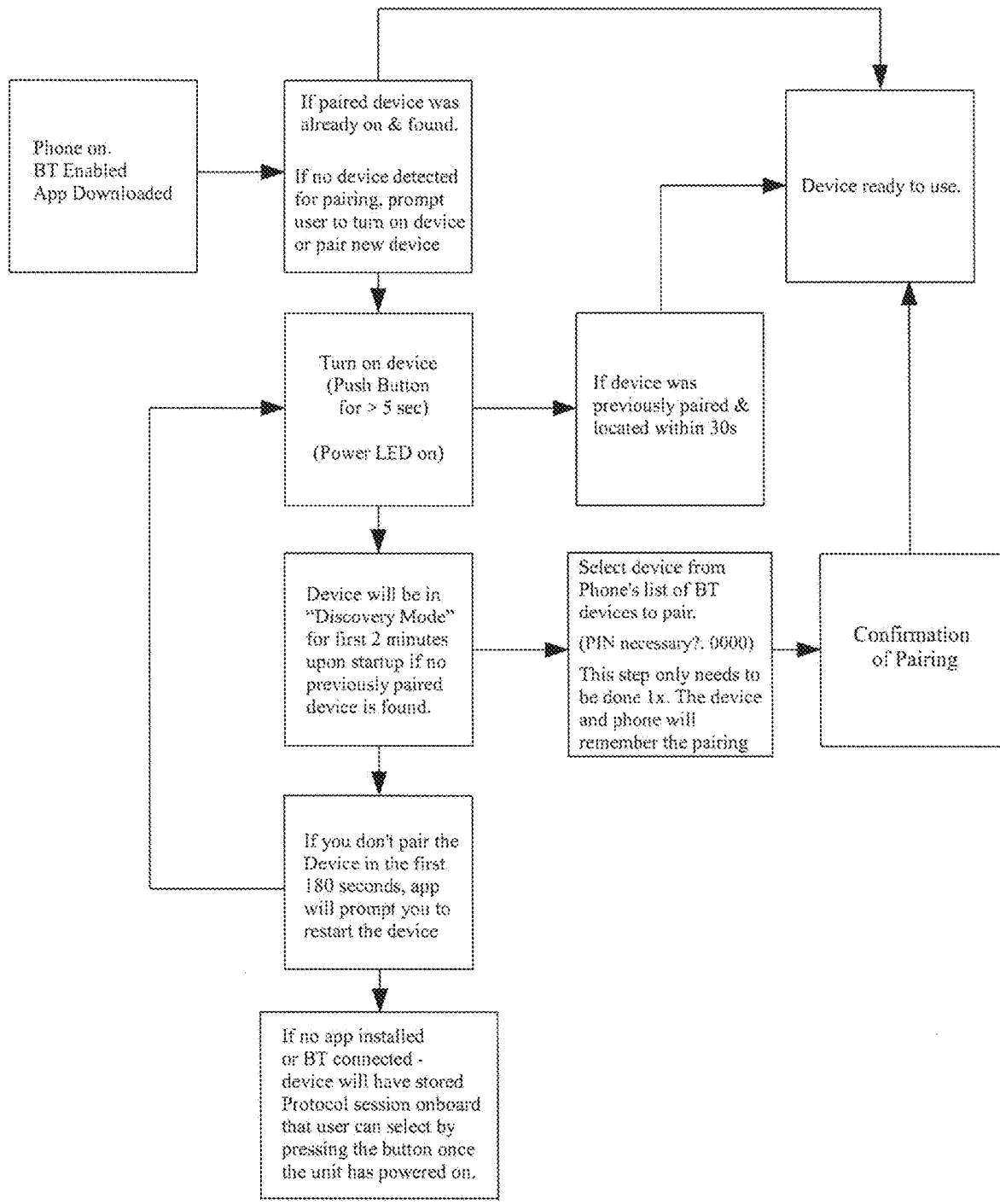
FIG. 51 is a flow chart of options available to the user on the Initialization/Startup Screen of the graphic user interface (GUI)
Figure 52:
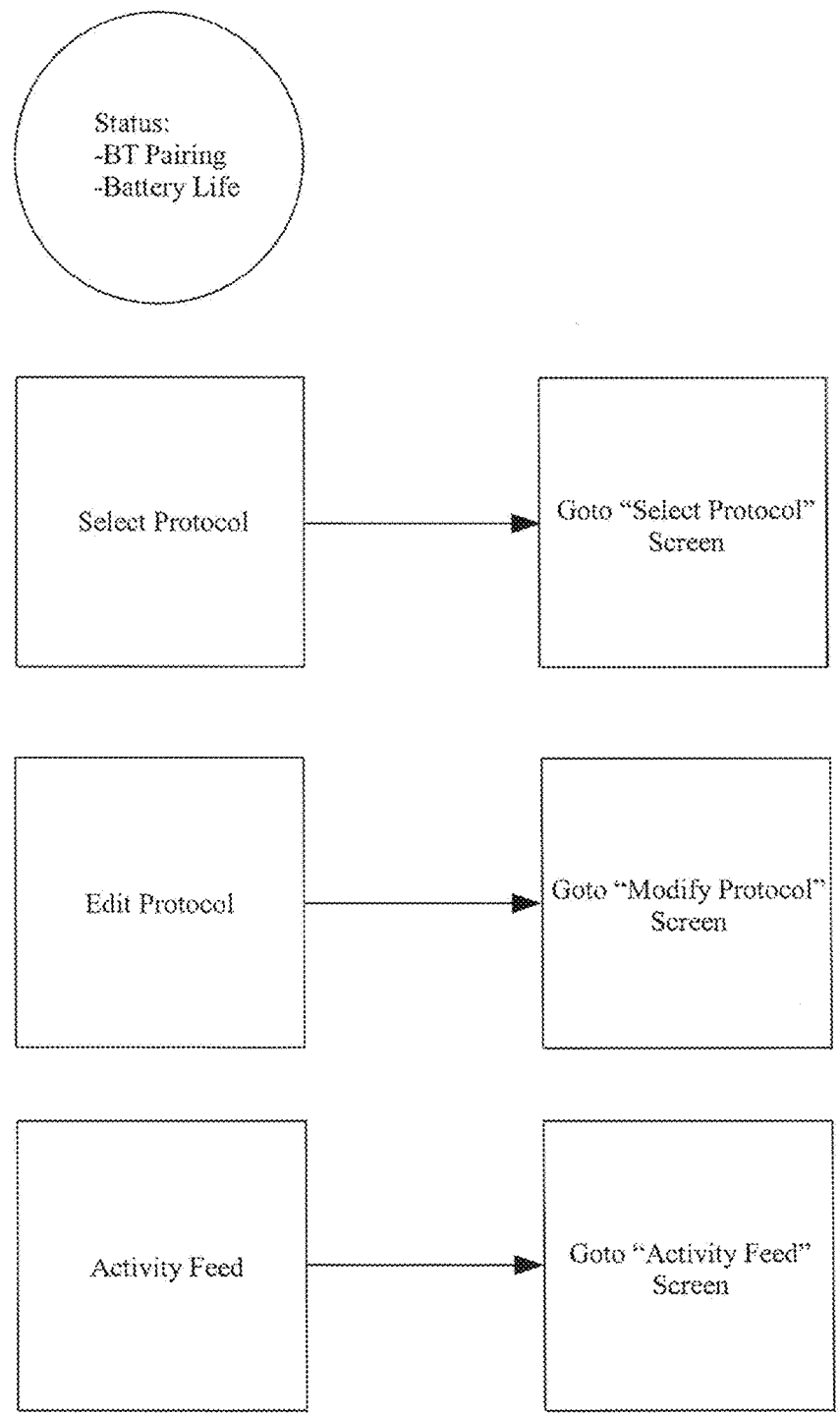
FIG. 52 is a flow chart of options available to the user on the Main Screen of the GUI.
Figure 53A:
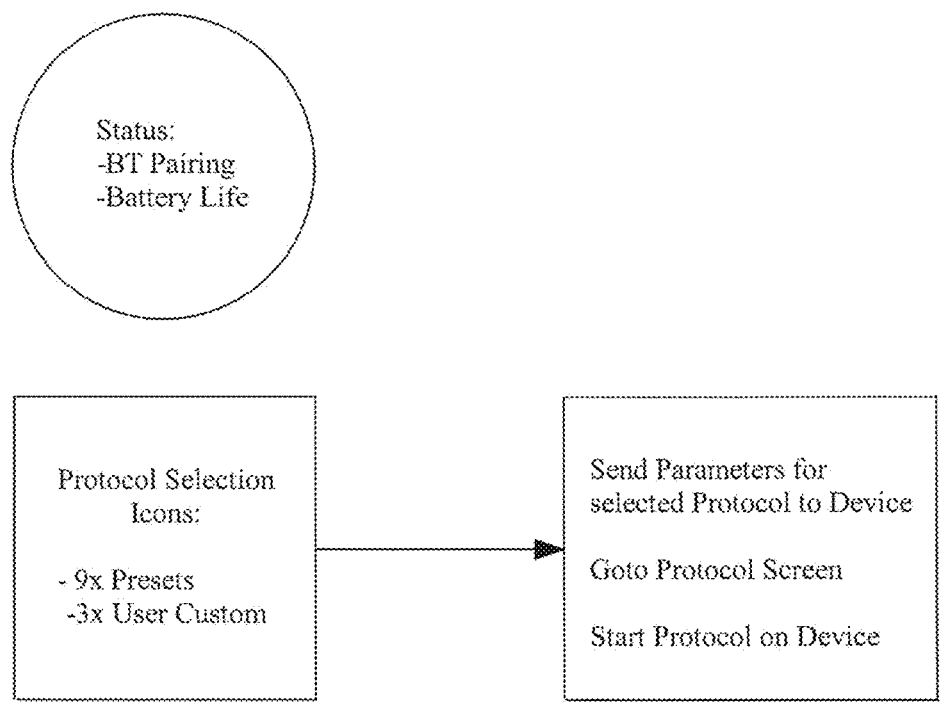
FIG. 53A is a flow chart of options available to the user on the Protocol Selection Screen of the GUI.
Figure 53B:
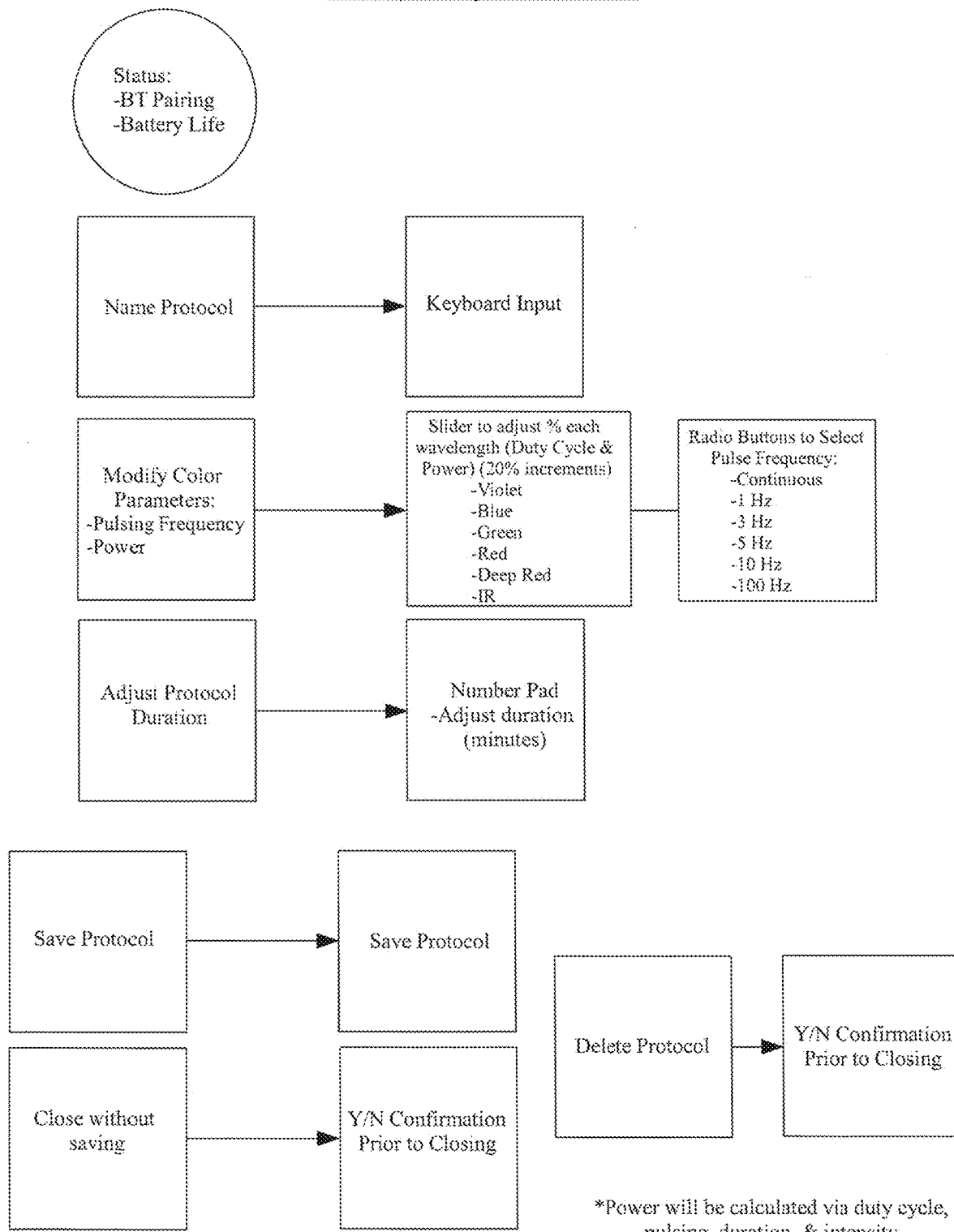
FIG. 53B is a flow chart of the Modify Protocol Screen of the GUI.
Figure 53C:
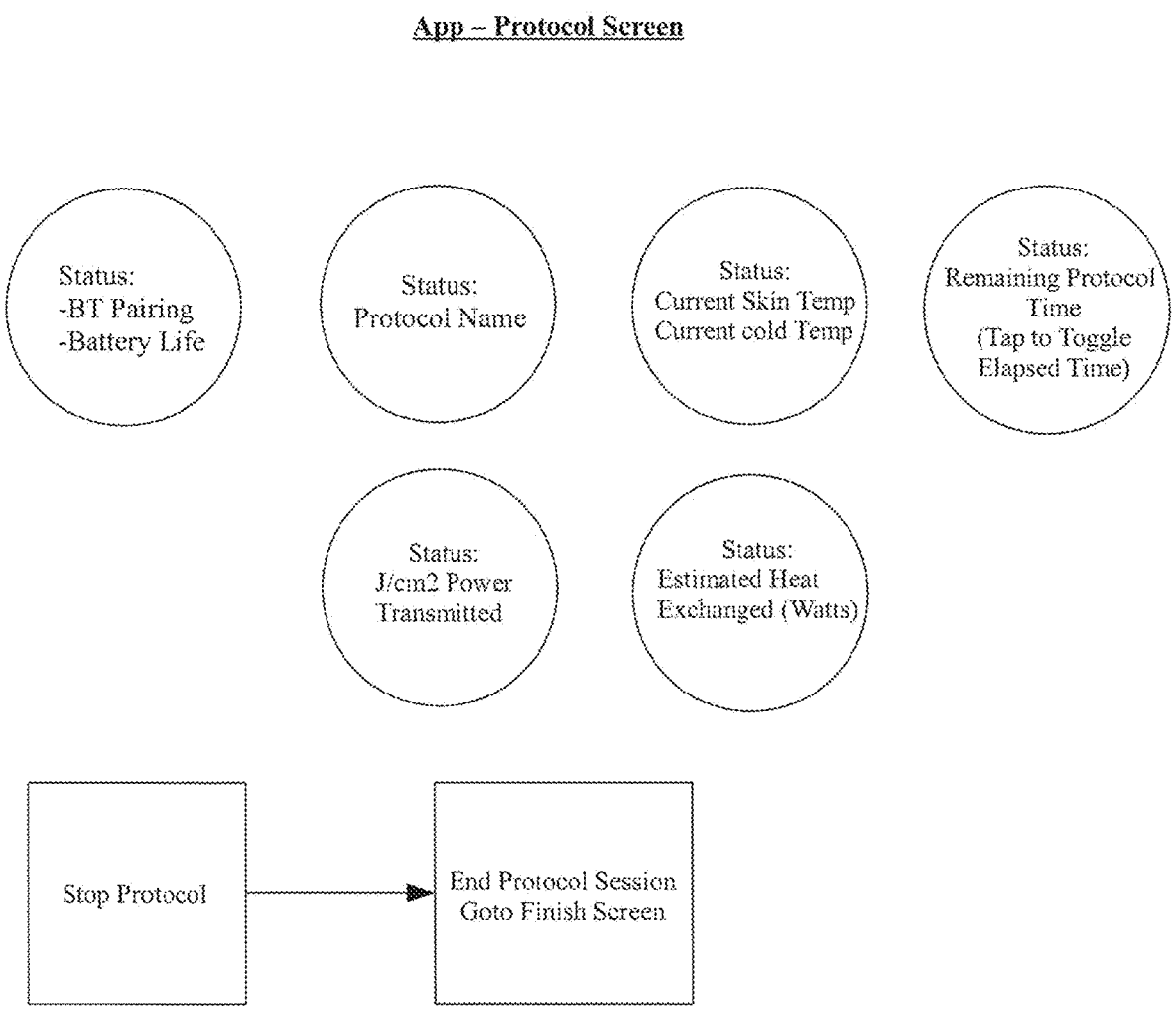
FIG. 53C is a flow chart of the Protocol Screen of the GUI.
Figure 54:
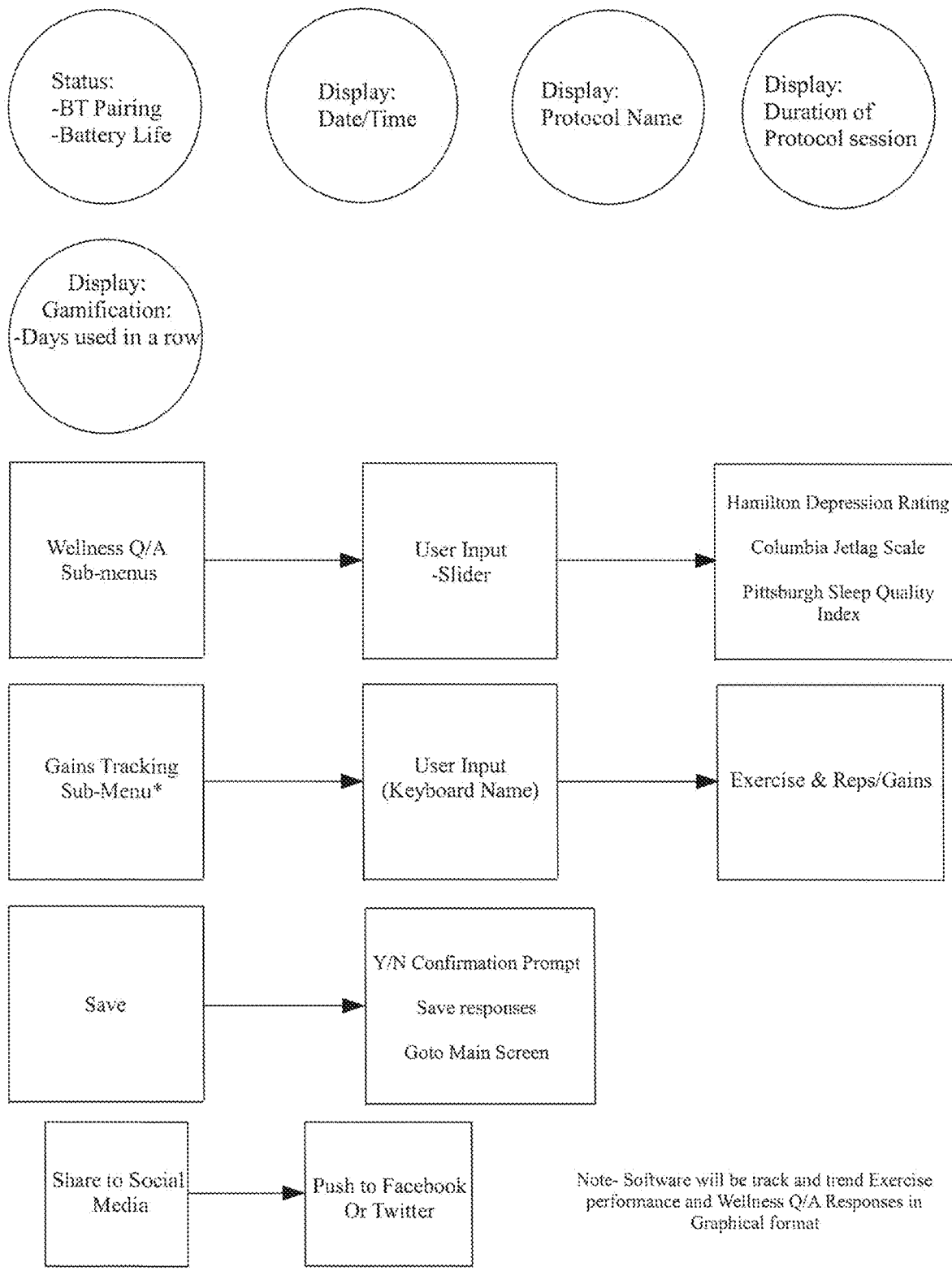
FIG. 54 is a flow chart of options available to the user on the Finish Screen of the GUI.
Figure 55:
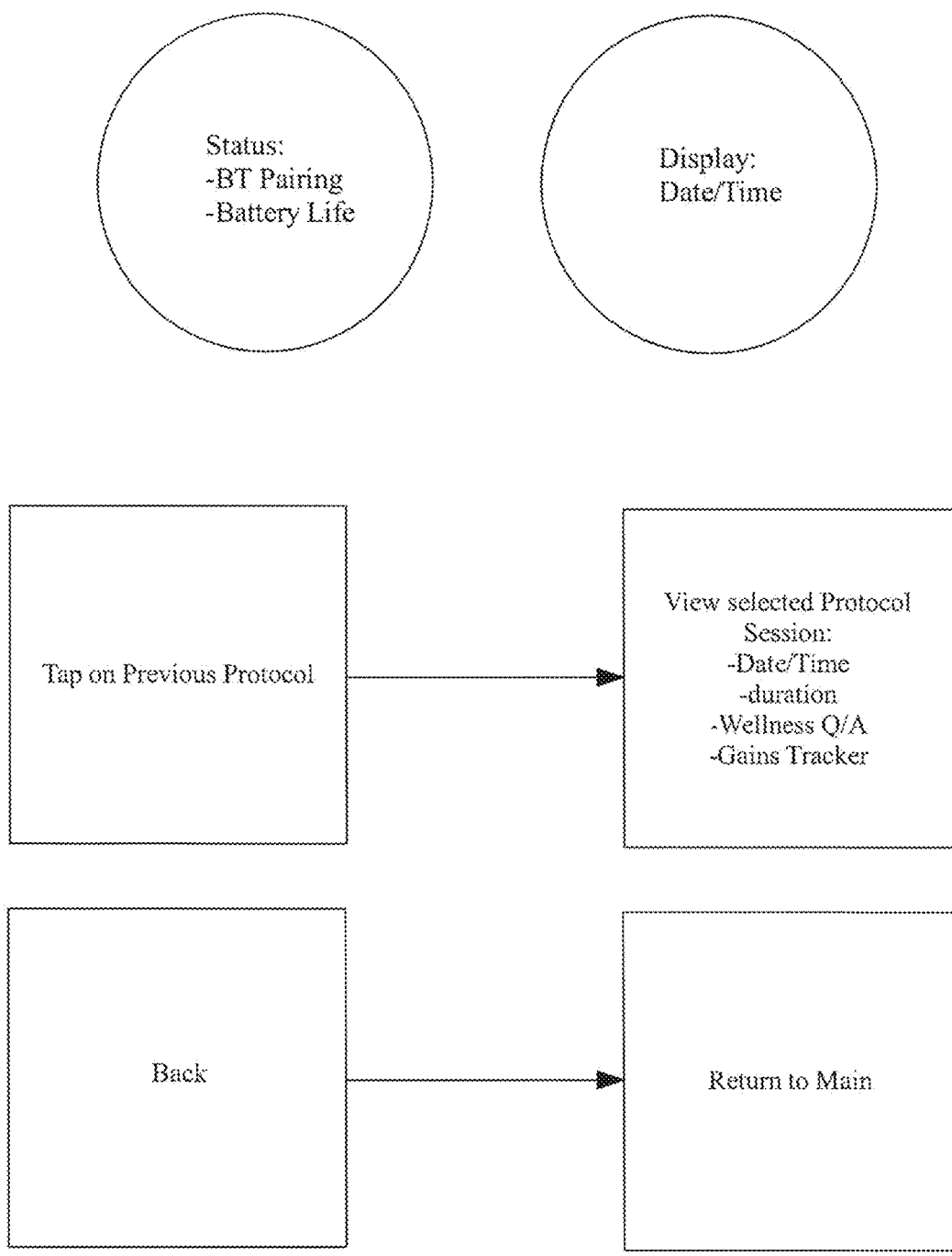
FIG. 55 is a flow chart of options available to the user on the Activity Feed Screen of the GUI.
Figure 56:
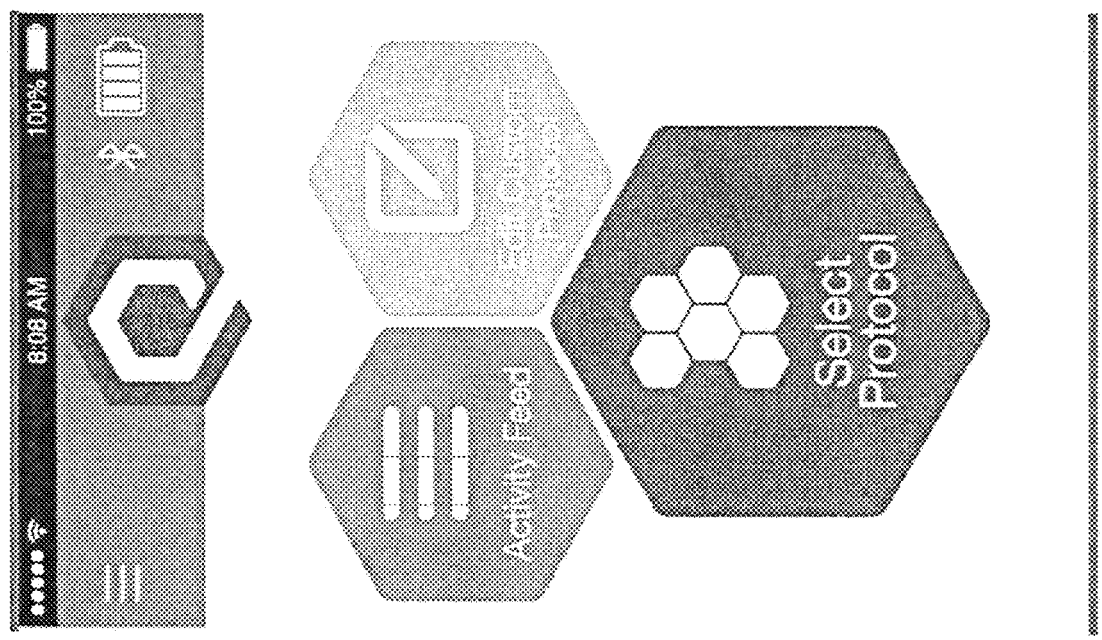
FIG. 56 depicts the Main Screen of the GUI, which may include a select protocol button, an edit custom protocol button, and an activity feed button.
Figure 57:
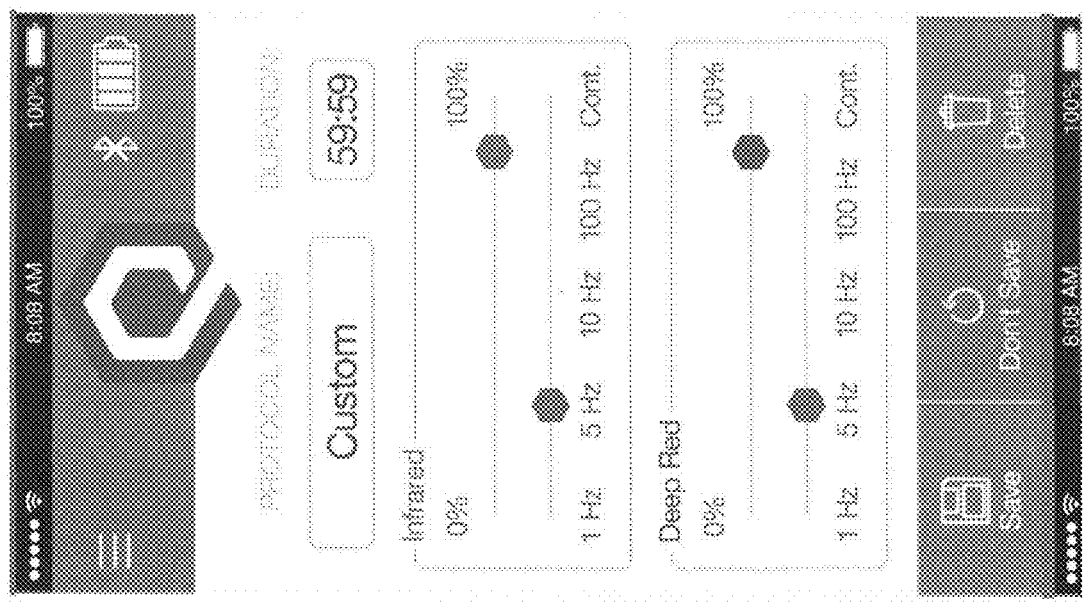
FIG. 57 depicts a Custom Protocol Screen of the GUI, which may include slider buttons that may permit adjustment to treatment parameters, including light intensity.
Figure 58:
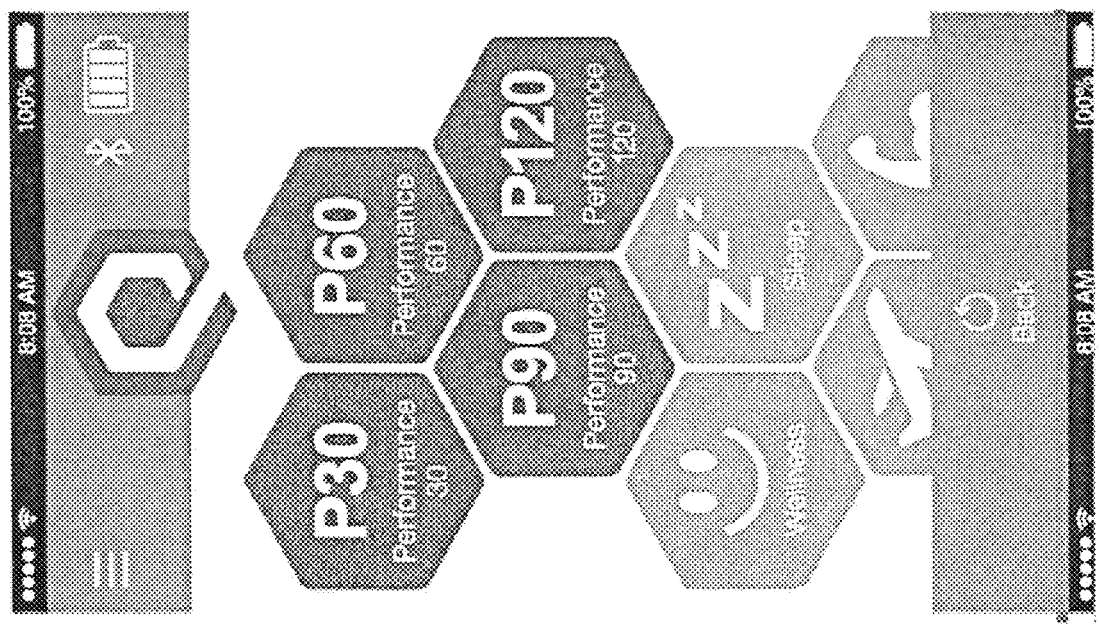
FIG. 58 depicts a protocol selection screen that may permit selection of a protocol from among a plurality of standard treatment protocols, which may include a 30 minute performance protocol, a 60 minute performance protocol, etc.
Figure 59:
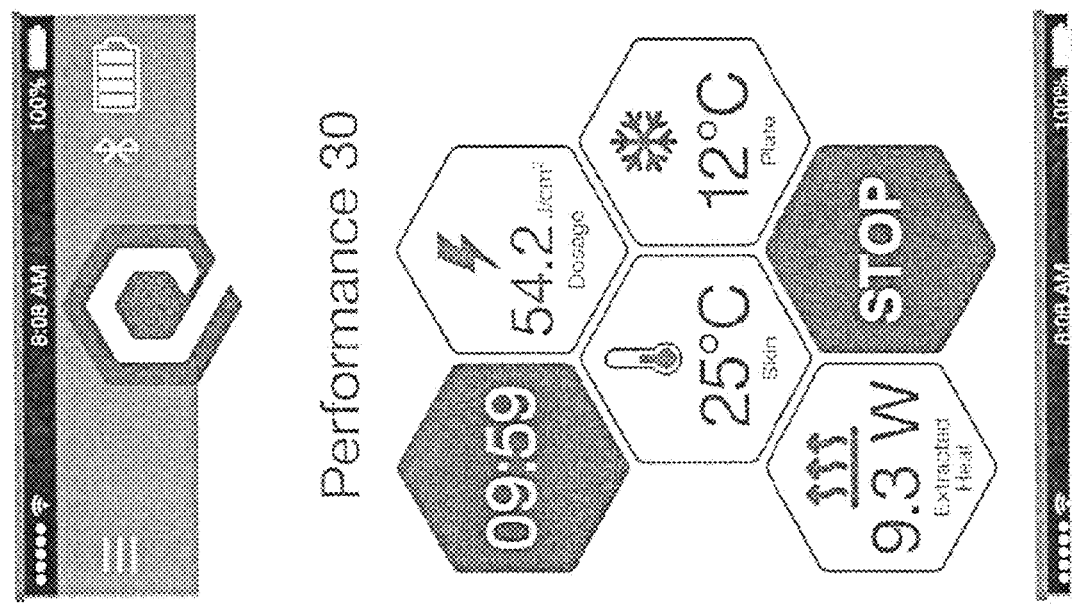
FIG. 59 shows the parameters for the selected protocol, i.e., the Performance 30 protocol.
Figure 60:
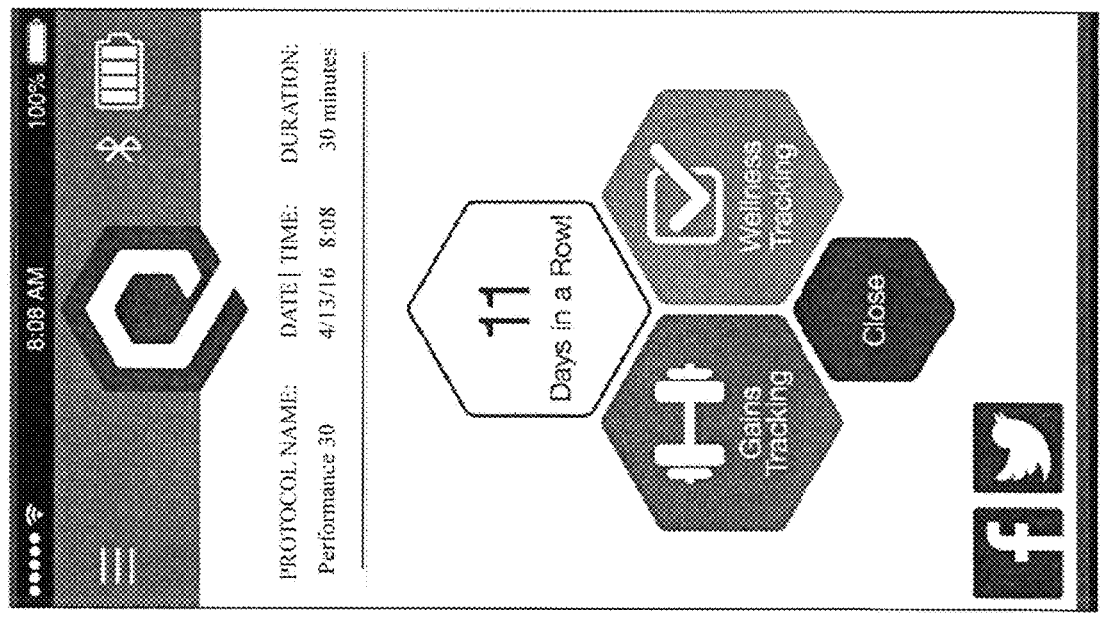
FIG. 60 shows treatment tracking data for the user of the device, and provides buttons that may be toggled for gains tracking and wellness tracking, that may launch those corresponding screens.
Figure 61:
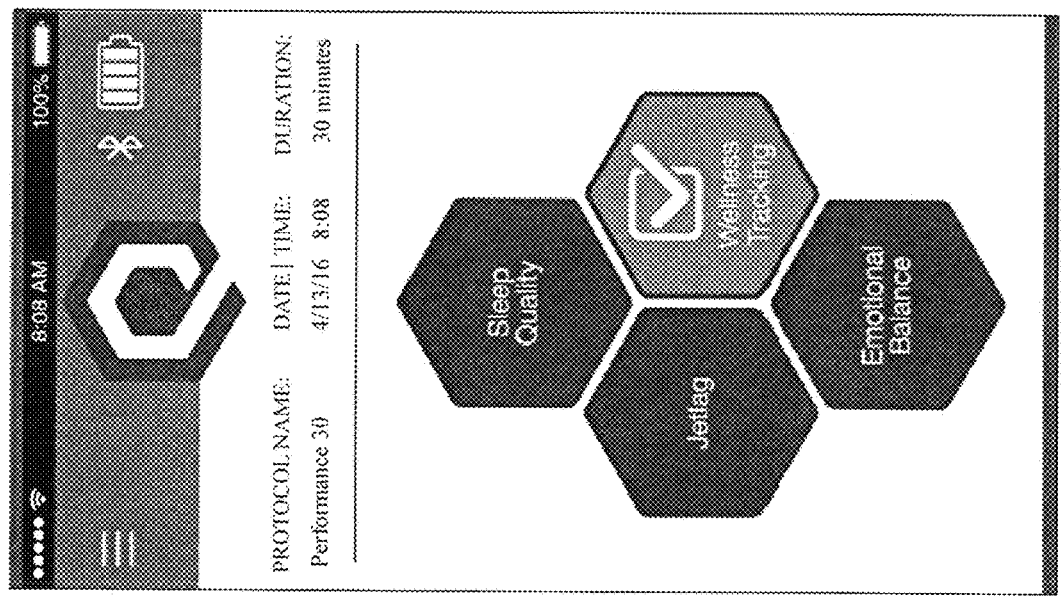
FIG. 61 shows a wellness tracking screen that will be launched by toggling the button for wellness tracking shown in FIG. 60, which tracking screen may provide additional buttons that may be toggled for sleep quality, jet lag, and emotional balance, and which may launch those corresponding screen, and where toggling of the wellness tracking button in FIG. 61 may return the user to the screen of FIG. 60.
Figure 62:
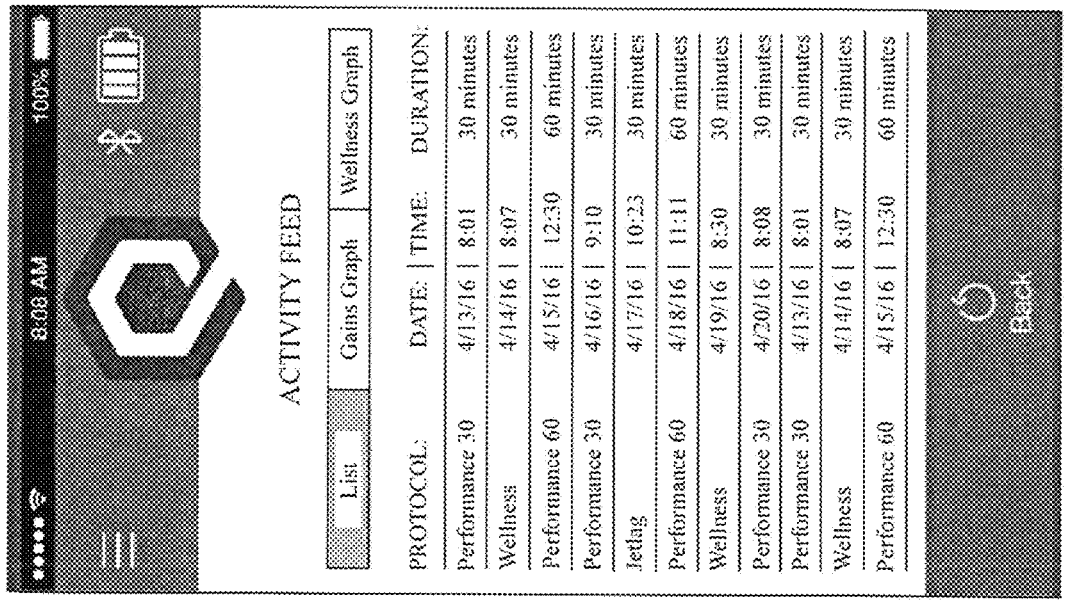
FIG. 62 shows an activity feed log.
Figure 63:
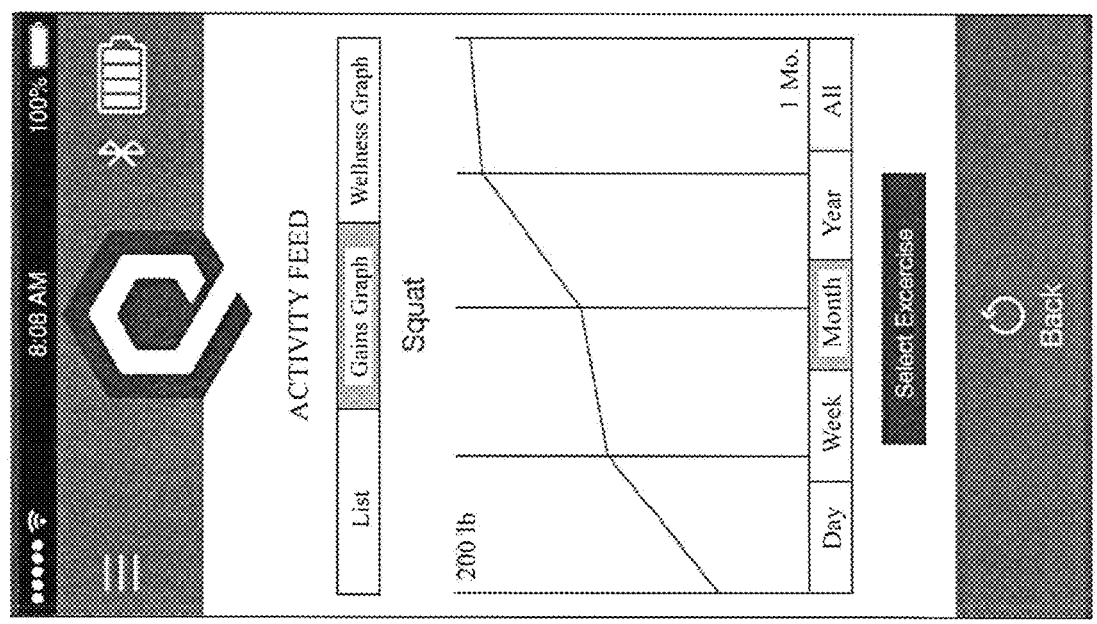
FIG. 63 illustrates an activity feed log showing monthly performance results for the user in performing squats.
Figure 64:
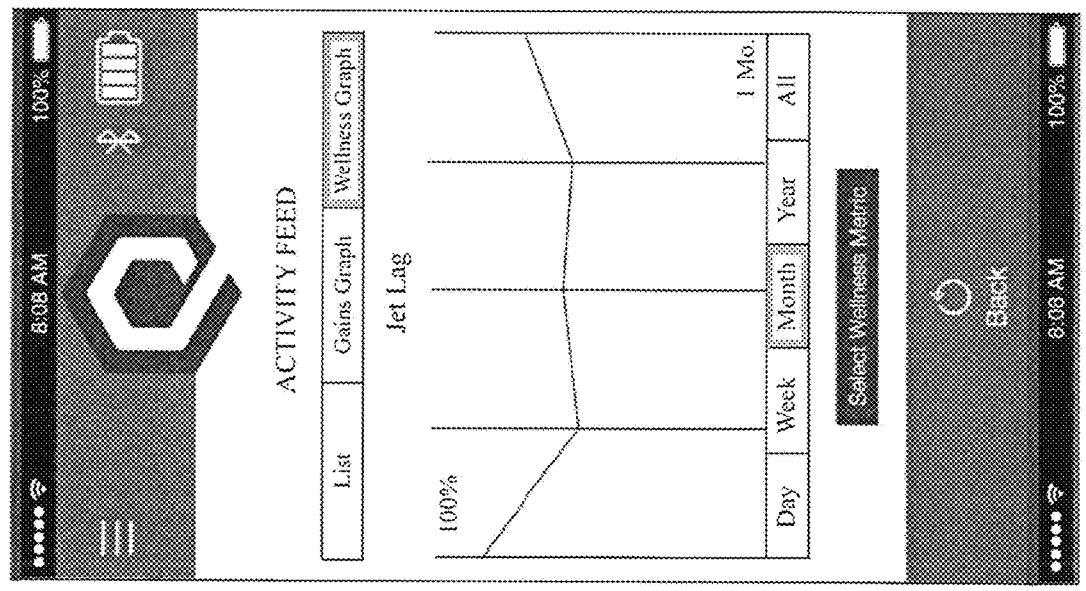
FIG. 64 illustrates a wellness metric log showing monthly performance results for the user in terms of response to jet lag.
Figure 65:
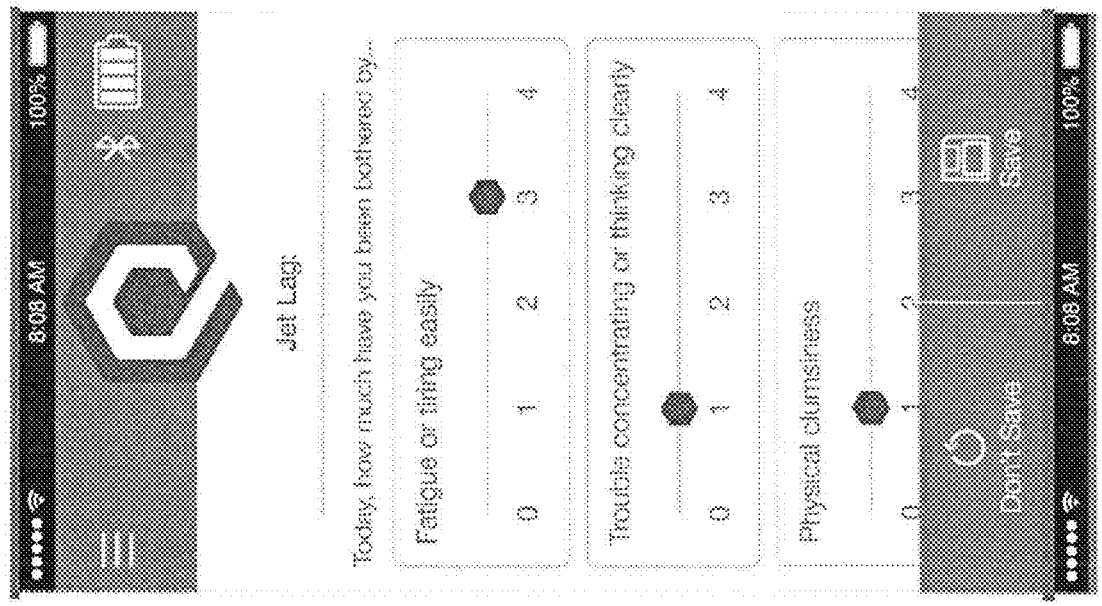
FIG. 65 illustrates a tracking screen with slider buttons for the user to input self-assessment values for the user's degree of fatigue, ability to concentrate, and physical clumsiness.
Figure 66:
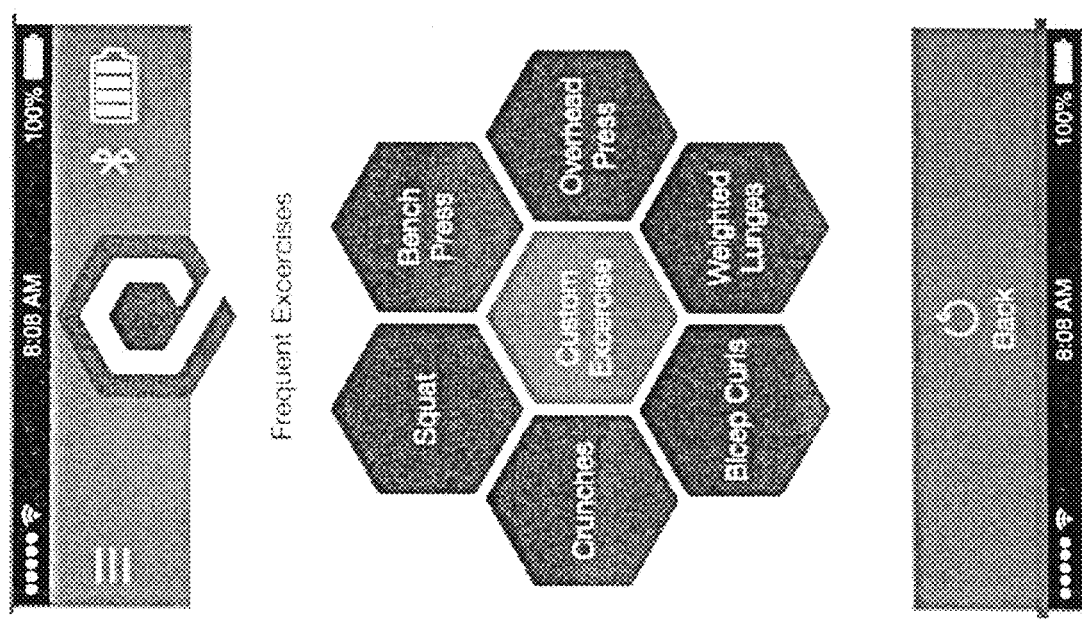
FIG. 66 is a gains tracking screen with buttons for frequently performed exercises permitting entry by the user of performance metrics for each.
Figure 67:
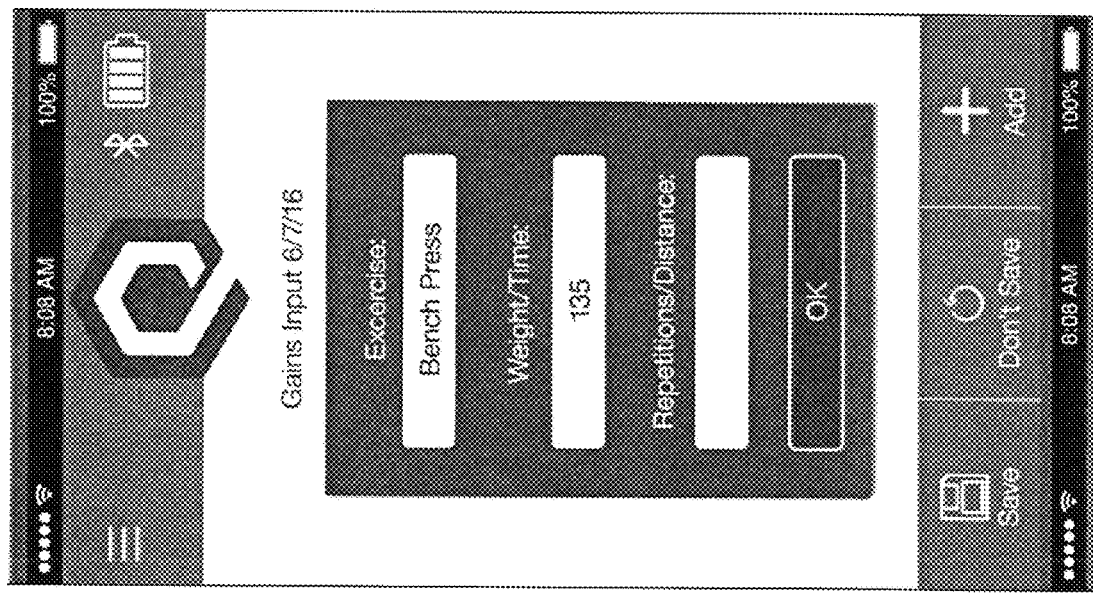
FIG. 67 is a gains input screen launched from the screen of FIG. 66, in which the user may enter metrics for his/her performance with respect to the bench press.
Figure 68:
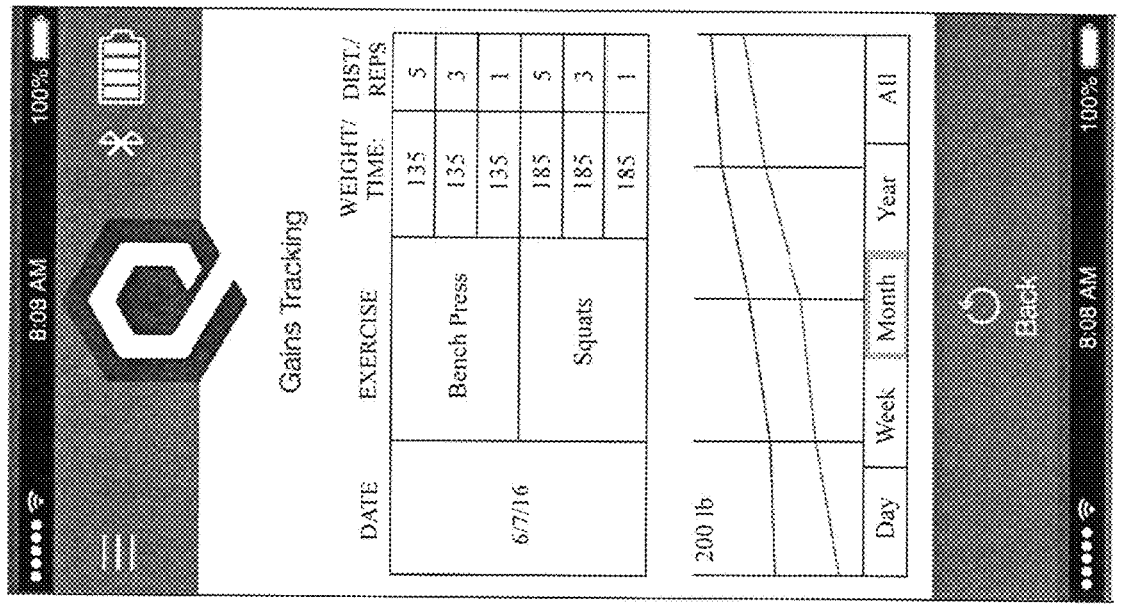
FIG. 68 is a gains tracking screen, in which the user may view metrics for his/her performance in various exercises.
Figure 69:
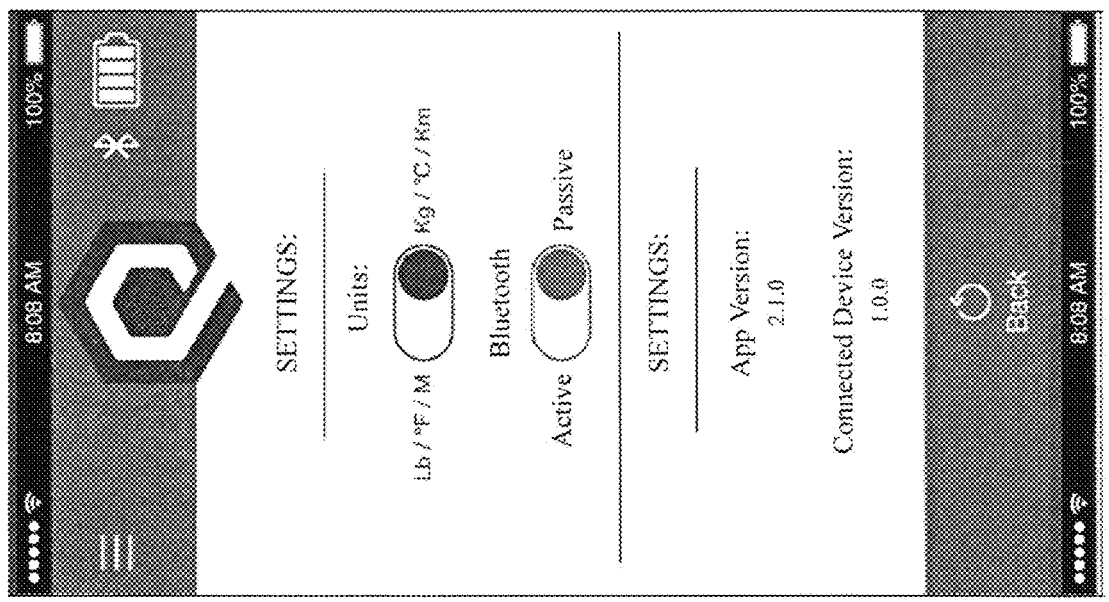
FIG. 69 is a settings screen.

As seen in FIG. 12, the light sources 110, 111, and 112 for the first treatment module 100 may be integrated into a printed circuit board 120 that may be supported in a housing 130, which may be through the use of an extruded body 140. The housing may provide support to the light sources so that they may be roughly ¼ of an inch away from the skin of the user. In another embodiment, the device may be closer or even adjacent to the skin and the light may penetrate at least 10 mm to 30 mm in depth into the skin in the area of the veins, for the red/infrared wavelengths. In this embodiment the treatment area at the depth of at least 15 mm to 30 mm is about 25 square centimeters. The extruded body 140 may incorporate a plurality of openings on a second side 102 of the first treatment module 100, to permit dissipation of heat produced by the lights and electronic components, as illustrated in FIG. 13. The extruded body 140 may terminate at a top plate 141. A window 150 may overlay and protect the light sources 110, 111, and 112. Material selection for the window 150 may be optimized based on transmissivity of the particular wavelengths utilized herein, and based on other relevant characteristics, with some preferred material choices and characteristics being shown in FIGS. 46-47. The window(s) may be made of silica, quartz, borosilicate, polycarbonate, or sapphire, and may preferably be made of polycarbonate because of its favorable qualities with respect to transmissivity, moldability, and cost.

The light sources and electronic components of the first treatment module 100 may be powered using an electrical cord and plug that may be connected to a wall outlet to receive power therefrom. Alternatively, the bracelet 10 may be configured to be powered by a battery 160 to accommodate portable use. Bracelet 10 may be powered by a 2000 mAh, 7.4 V lithium polymer battery 160, to provide for at least one hour of therapeutic blood irradiation, and to also provide the body temperature regulation discussed hereinafter. Power may be provided at 1 hertz up to continuous. Other types of batteries can also be used. Management and budgeting of power from the battery 160 for each of the components is detailed in FIGS. 49 and 50, for the respective light arrangements of FIGS. 32 and 38. The bracelet 10 may be configured for the battery 160 to provide a total of 415 mW to the one or more light sources that emit the light at the 850 nm and the 660 nm wavelengths/ranges, and may provide a total of 335 mW to the light sources that emit the light at the 630 nm, the 532 nm, and the 450 nm wavelengths/ranges.

The second treatment module 200 may have dual functionality, being configured to provide additional selective wavelengths of light specifically directed to vasculature of the wrist (i.e., the radial and ulnar arteries), and to provide body temperature regulation, when and if desired, control of which may be through a selected treatment protocol.

Figure 14:
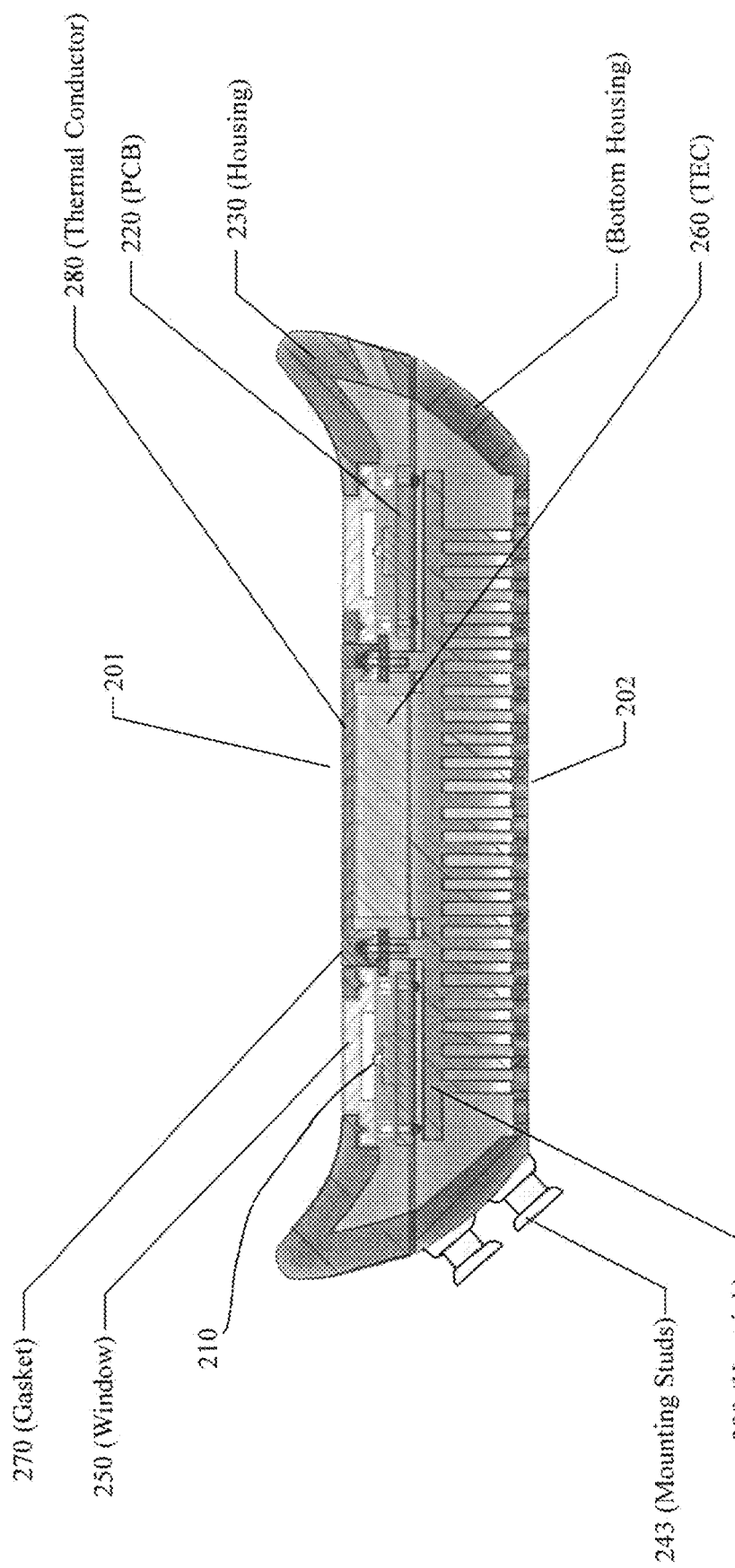
FIG. 14 is a cross-sectional view through the second treatment module.
Figure 26:
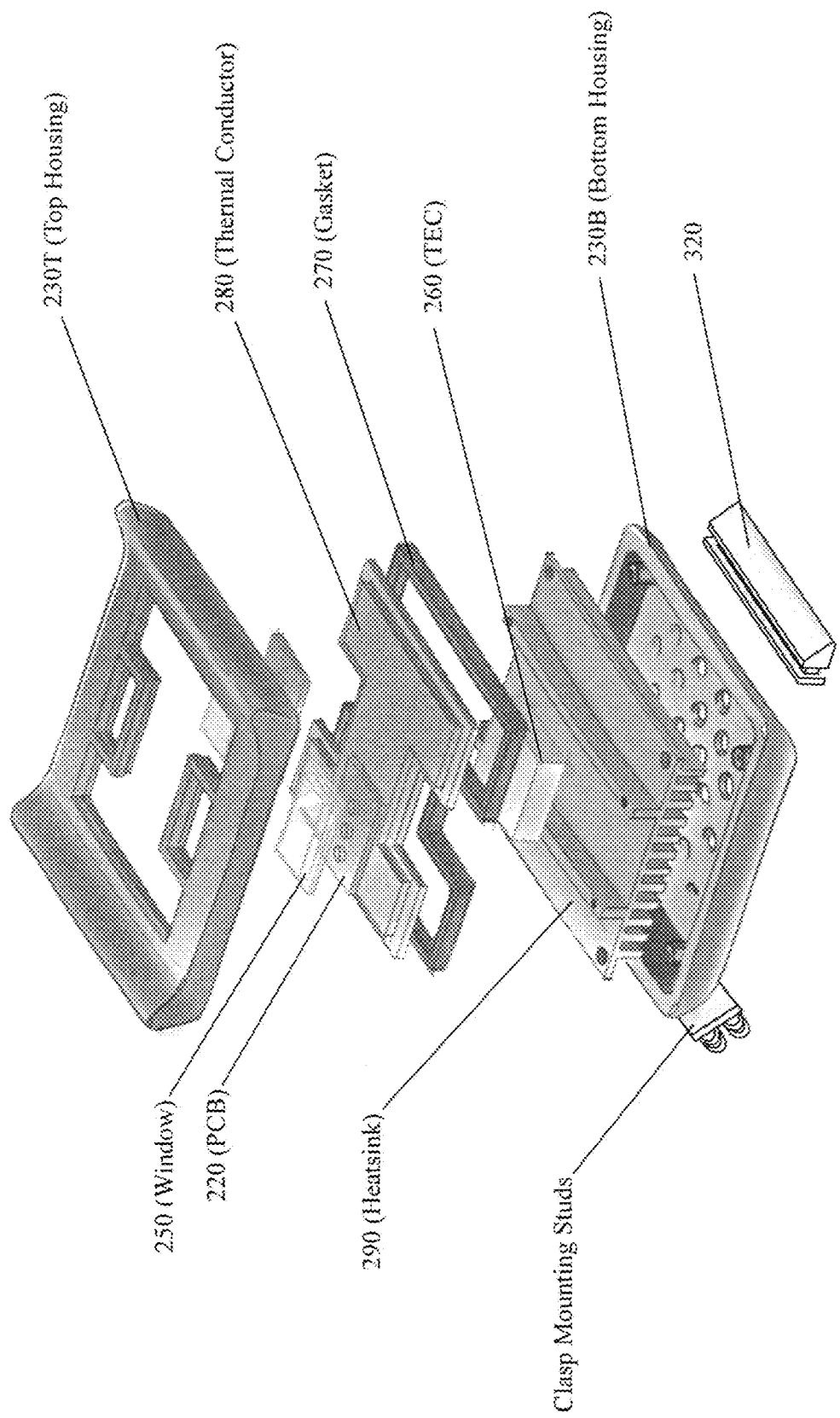
FIG. 26 is an exploded view showing the parts of the second module.
Figure 36:
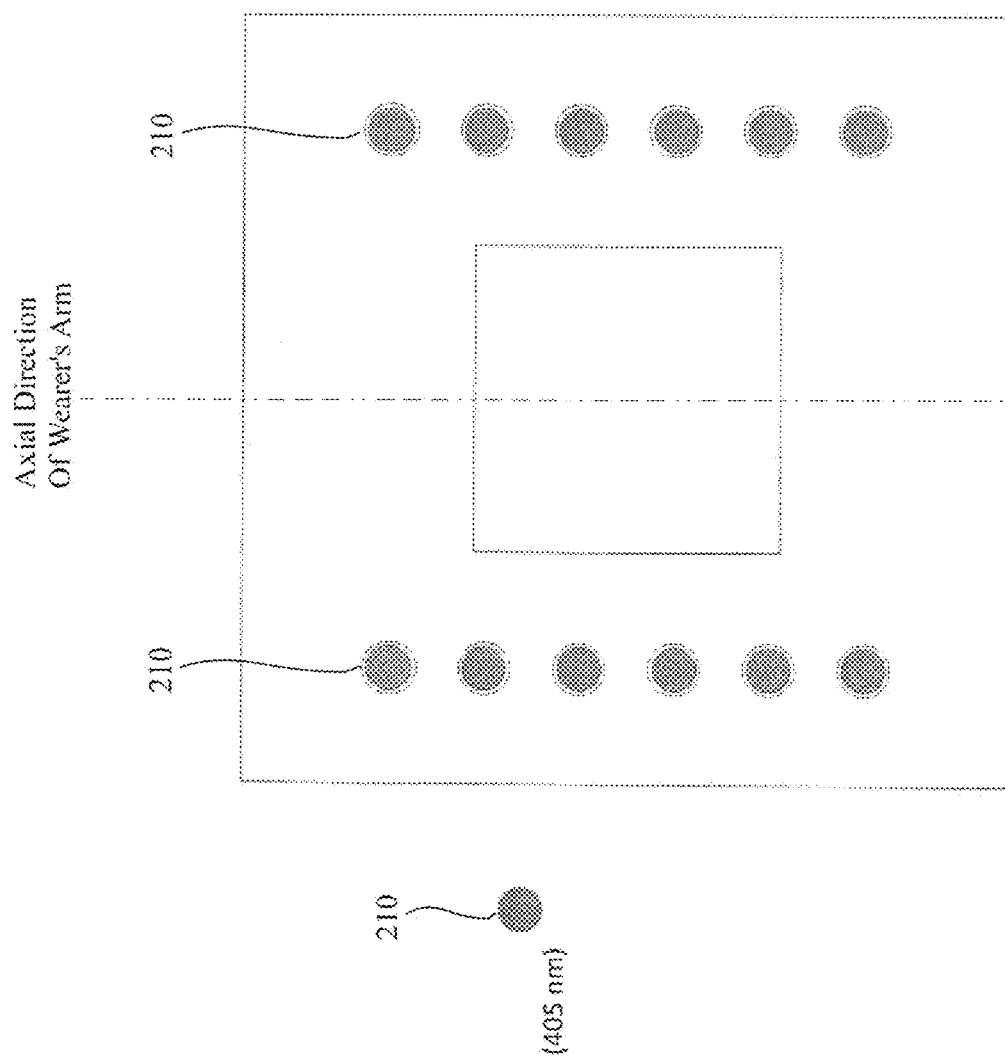
FIG. 36 is a view showing selective placement of the plurality of light sources in the second treatment module, which are configured to provide 405 nm wavelength/ranges of light.
Figure 37:
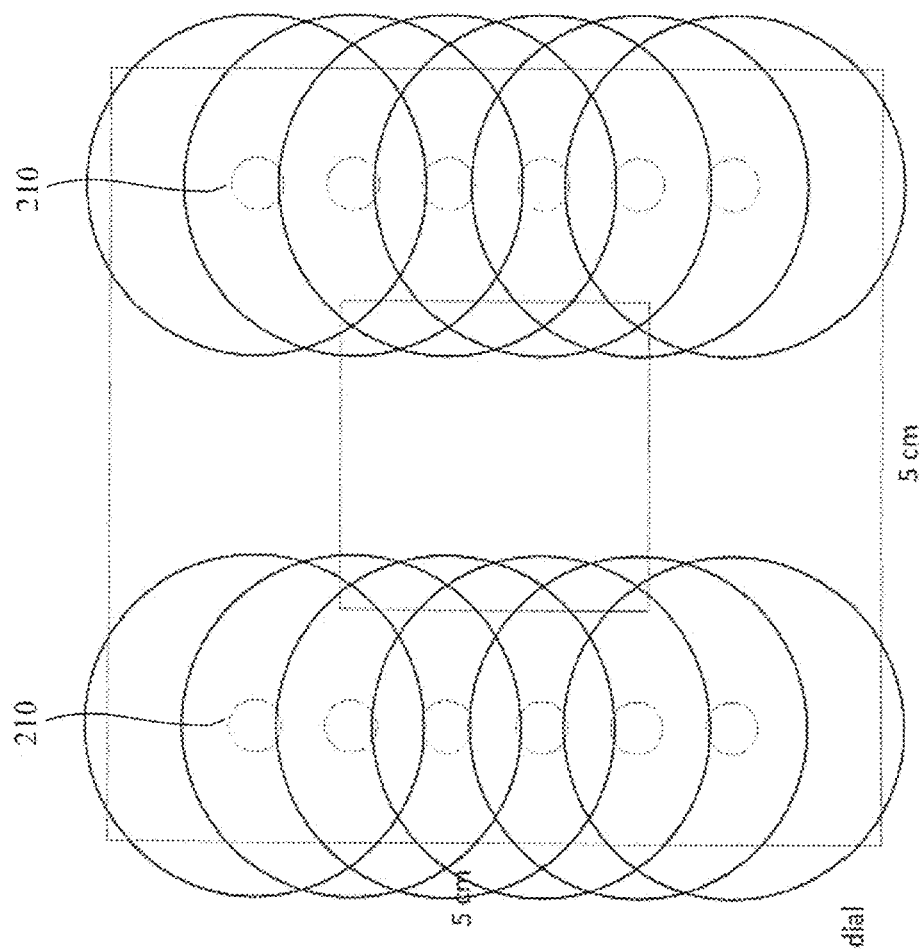
FIG. 37 is a view showing that selective placement of the plurality of light sources in the second treatment module provides 405 nm wavelength/ranges irradiation focused upon each of the radial and ulnar arteries in the wrist.

As seen in FIG. 14 (and the exploded view of FIG. 26), the second treatment module 200 may broadly include one or more light sources configured to emit selective wavelengths of light from a first side 201 of the first treatment module. In one embodiment, the second treatment module 100 may broadly include a plurality of light sources 210 configured to emit light at a range of wavelengths that may preferably be within +/−5 nanometers of 405 nm, and is more preferably within +/−3 nanometers, and is most preferably right at 405 nm. As seen in FIG. 14 and FIG. 36, the light sources 210 for the second treatment module 200 may be integrated into a printed circuit board 120 that may be supported in a housing 230, to provide support to the light sources at a suitable distance away from the skin of the user, which may be roughly ¼ of an inch. The housing 230 may be split into top and bottom housing portions (230T/230B). A peel and stick disposable cushion 170 may be releasably secured to the first side 101 of the first treatment module 100, which may provide for comfortable contact with the wearer's skin, and may constitute a portion of the ¼ inch spacing between the lights and the user's skin surface.

Figure 7:
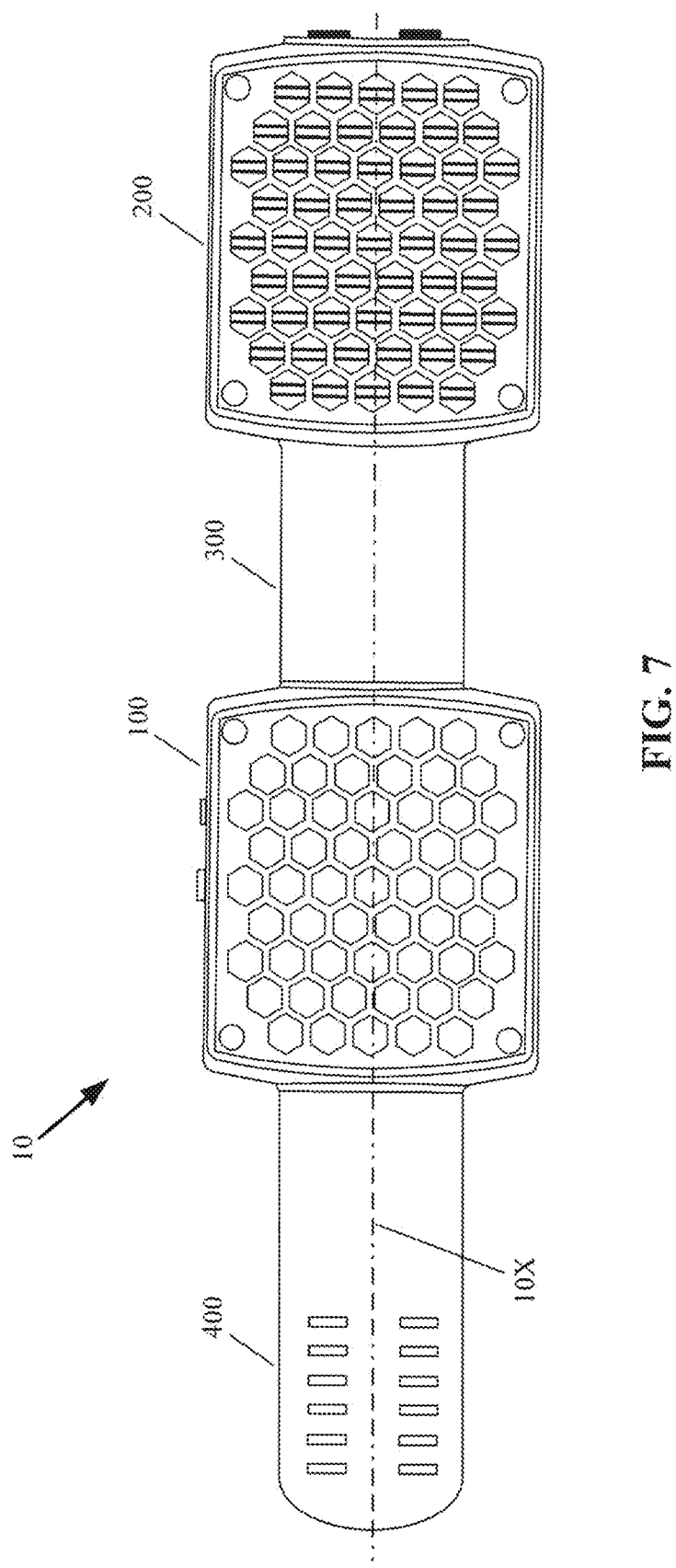
FIG. 7 illustrates a view of the bracelet of FIG. 1, shown with the attachment band detached, and the first and second treatment modules and the connector band and attachment band all stretched out to be in line.
Figure 30A:
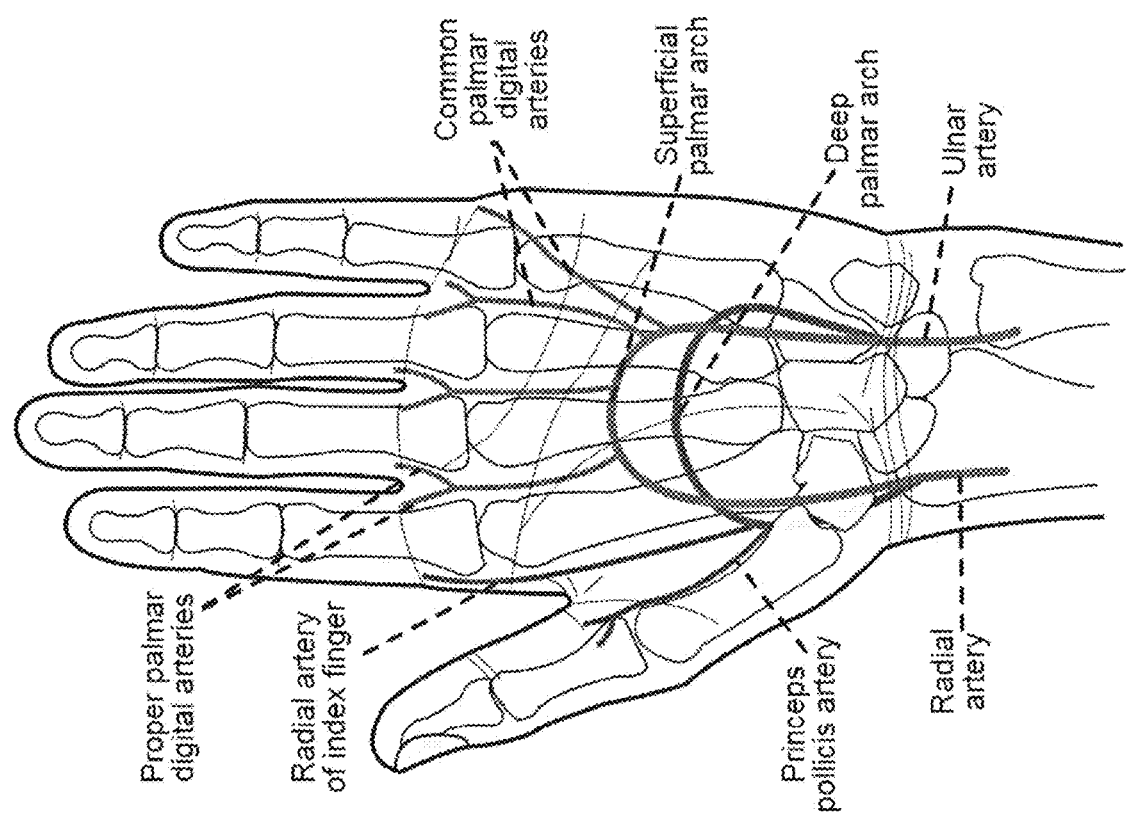
FIG. 30A is a transparent top view of the human hand, showing positioning of the radial and ulnar arteries in the wrist region.
Figure 30B:
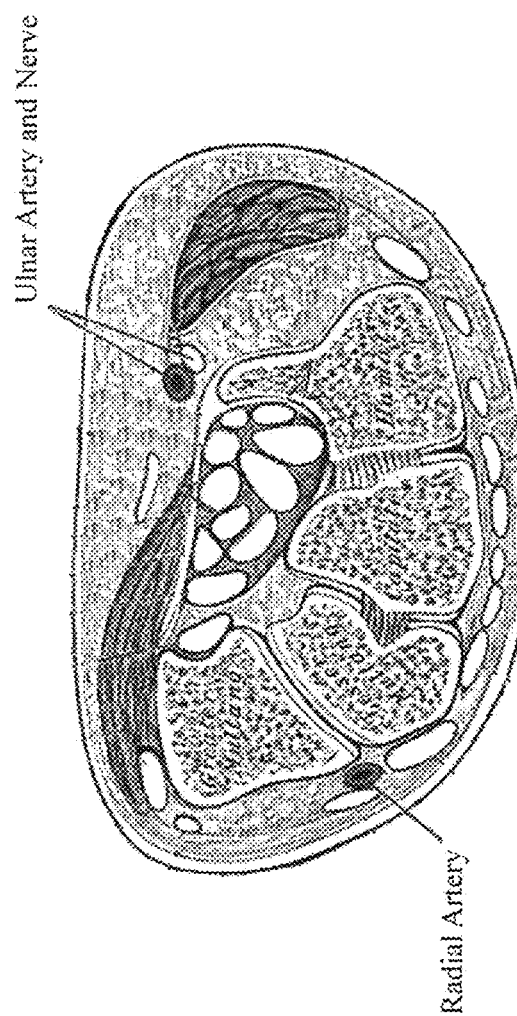
FIG. 30B is a cross-section through the person's wrist showing the general location of the radial and ulnar arteries in the wrist region.
Figures 31, 31A, 31B:
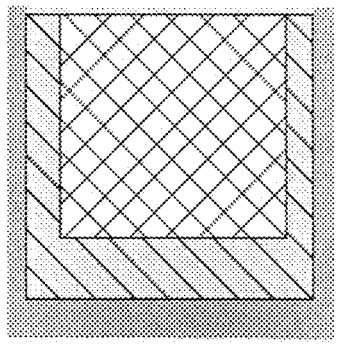
FIG. 31 is a schematic view of the human hand and wrist, showing different size variations therein.
FIG. 31A is a view showing a table listing ideal and max wrist device areas for each of the $95^{th}$ percentile male and the $5^{th}$ percentile female.
FIG. 31B is a view showing a table of device length and width parameters for the three device wrist areas shown in FIG. 31.

In one arrangement of the light sources 210 for the second treatment module 200, as shown in FIG. 36, there may be a first row of six light sources 210 that may be positioned to be parallel to, but spaced apart from, the axis of the second treatment module that is to be aligned with the axial direction of the person's arm (i.e., being in a row oriented to be substantially perpendicular to the axial line 10X in FIG. 7, which is through the center of the connector band 300 and the attachment band 400). There may also be a second row of six light sources 210 that may be positioned in a row that may be parallel to the first row, but positioned on the opposite side of the first side 201. These first and second rows of light sources 210 in the second treatment module 200 may thus be respectively positioned to achieve optimal penetration to the radial and ulnar arteries in the wearer's wrist, which are shown in the cross-sectional and top views of the human hand in FIGS. 30B and 30A. It will be appreciated that other light arrangements are possible with the scope of the present invention. For example the alignment of the lights may be rotated from 0 to 180 degrees in either direction about the person's arm. A window 250 may overlay and protect the light sources 210.

The second treatment module 200 may also broadly include a cooling device 260 that may be configured to draw away heat and thereby cool the first side 201 of the second treatment module 200. The cooling device 260 may be a cooling pack (i.e., a bag or pouch configured to separate water from ammonium nitrate, calcium ammonium nitrate, or urea, whereby agitating the bag/pouch causes mixing of the components to produce an endothermic reaction, and thus cooling), an ice pack, and/or a thermoelectric cooling unit (TEC). Note that use hereinafter of the term TEC within the specification in discussing the cooling provided by the bracelet is merely for convenience, and is not intended to limit the different forms that the cooling device may take. The spaced positioning of the first and second rows of light sources 210 to particularly direct light upon the radial and ulnar arteries may permit placement of the cooling unit 260 therebetween, which may be generally centered within the second treatment module 200. The TEC may be located on a daughter board, and not on the main board (PCB), and may be controlled by a microcontroller.

Figure 15:
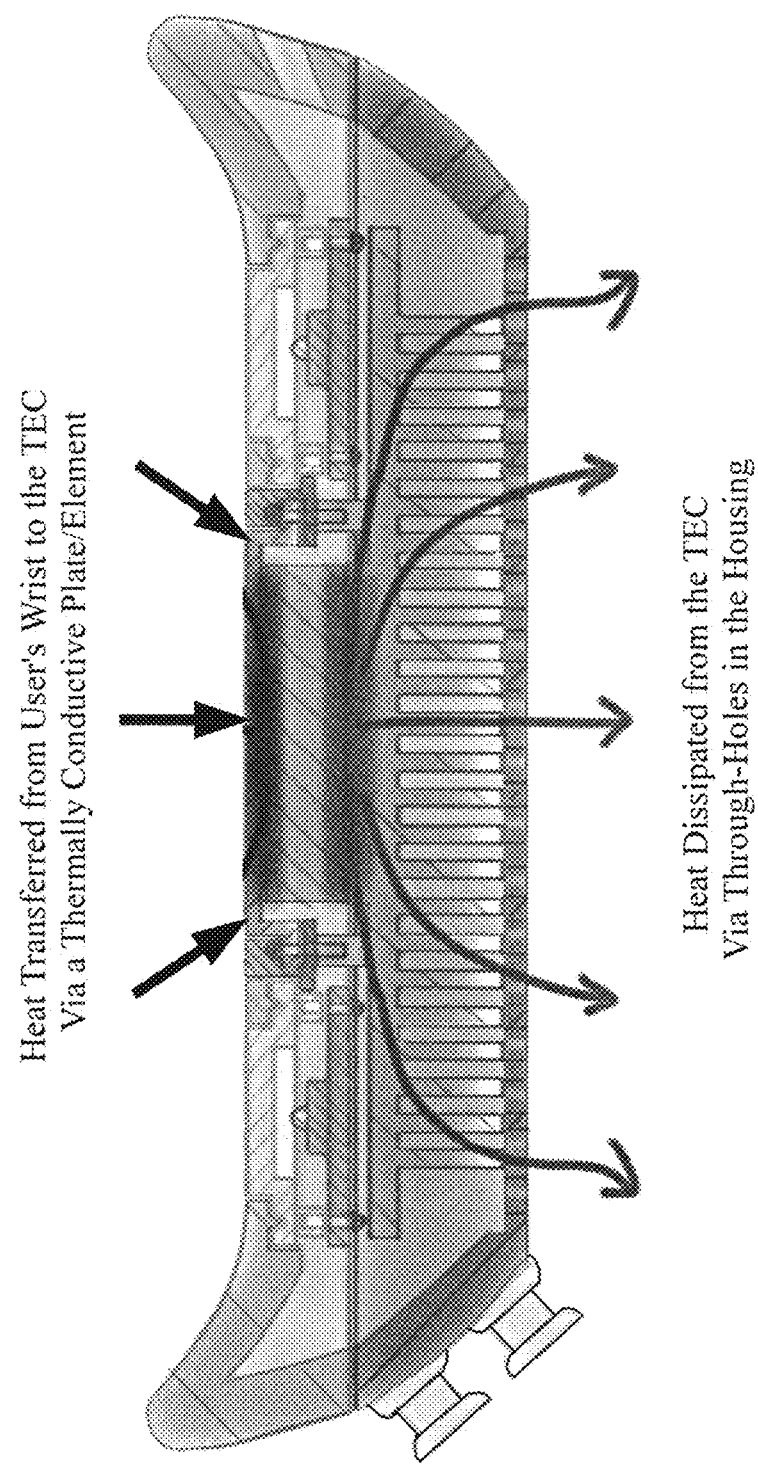
FIG. 15 is the cross-sectional view of FIG. 14, showing heat dissipation from the cooling unit away from a second side of the module, using a heat sink.

The second treatment module 200 may also broadly include a gasket 270 that may be positioned around the sides of the cooling unit 260, and may be thermally insulating to better ensure the directionality of the heat transfer (i.e., prevent leakage of heat around the sides of the cooling unit). Also, a plate 280 may be made of a thermally conductive material and may be positioned on at least a portion of the first side 201 of the second treatment module 200, to more effectively draw heat away from the wearer's wrist and towards the first side of the cooling unit 260. The thermally conductive plate 280, which may be H-shaped, may be positioned to overlie the cooling unit 240, as seen in the cross-sectional view of FIG. 14. A heat sink 290 may furthermore be used to draw heat away the second side of the thermoelectric cooling unit towards a second side 202 of the second treatment module 200, to be dispersed therefrom. In addition, a portion of the bottom housing 230B may also include fins, and may itself serve to conduct heat away from the TEC. The thermal transfer regime established by the second treatment module 200 is illustrated in FIG. 15. Heat is drawn away from the wrist of the user towards the thermally conductive plate 280, and is transferred, using the cooling unit 260, from the plate towards the second side 202 of the second treatment module 200, where it is dispersed therefrom using the plurality of fins of the heat sink 290. A fan (not shown) may also be used to blow air across the fins for increased heat transfer therefrom. The second treatment module 200 may be powered by the battery 160 located in the first treatment module 100, or alternatively, it may be powered by its own dedicated battery.

A peel and stick disposable cushion similar to cushion 170 may also be releasably secured about the periphery of the first side of the second treatment module 200; however, it thereat serves a thermal function. The cushion on the second treatment module 200 may be made of a material that is thermally resistant (i.e., having a low coefficient of thermal conductance), and may serve to increase the efficiency of heat transfer between the wearer's wrist and the TEC, rather than with respect to the surrounding air, which may be prevented by the cushion from flowing over the unit due to movement of the user and his/her arm.

Figure 27:
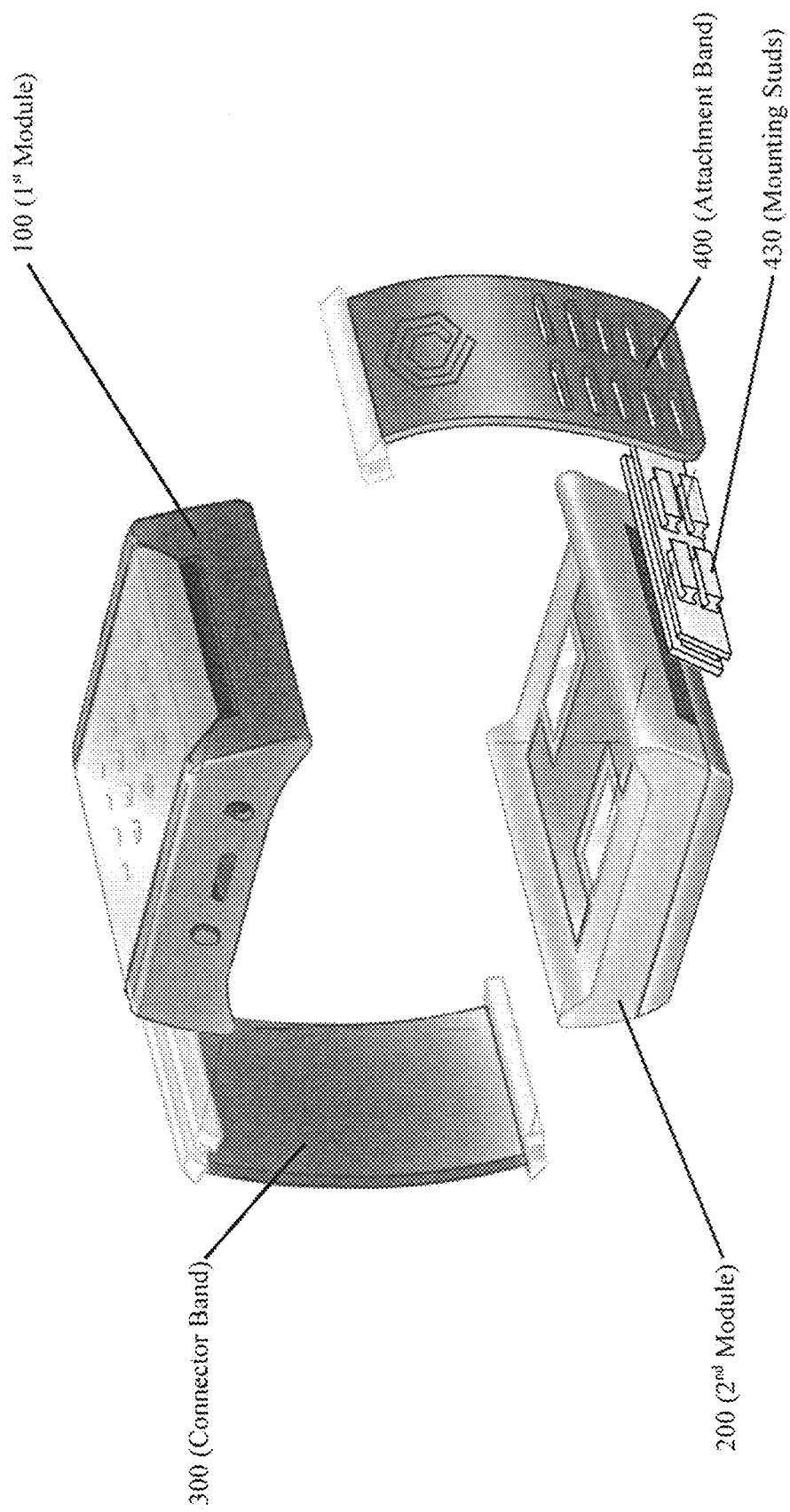
FIG. 27 is an exploded view showing the first module, the second module, the connector band, and the attachment band, prior to assembly.
Figures 28, 28A, 28B, 28C, 28D:
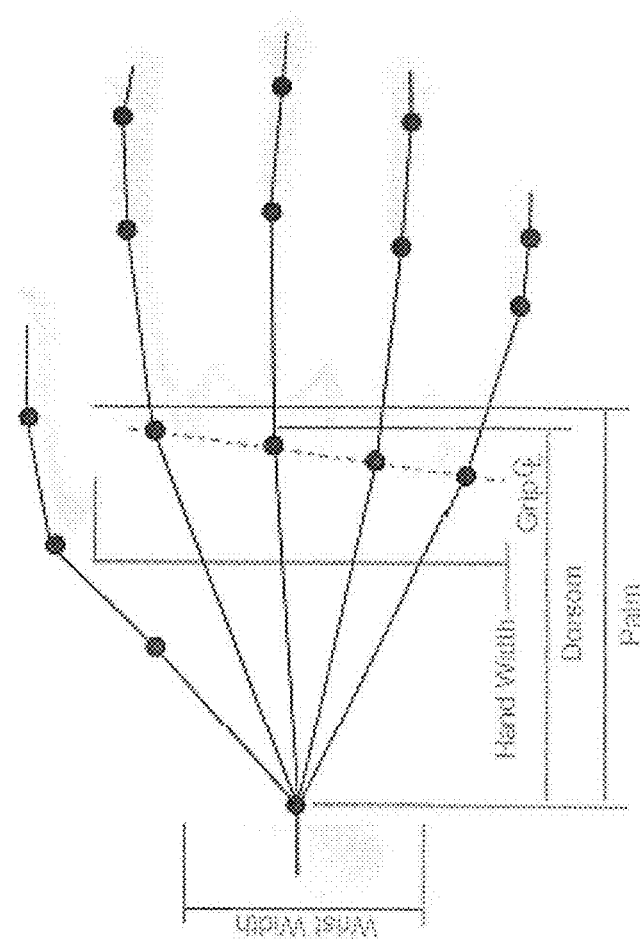
FIG. 28 is a schematic view indicating the distances between certain features of the hand and wrist.
FIG. 28A is a view showing a table of wrist widths for the $25^{th}$, the $50^{th}$, and the $95^{th}$ percentile male and female.
FIG. 28B is a view showing a table of hand widths for the $25^{th}$, the $50^{th}$, and the $95^{th}$ percentile male and female.
FIG. 28C is a view showing a table of dorsum distances for the $25^{th}$, the $50^{th}$, and the $95^{th}$ percentile male and female.

The connector band 300 for spaced coupling of the first treatment module 100 to the second treatment module 200, and the attachment band 400 for releasably/adjustable coupling of the first treatment module to the second treatment module for securement to the wearer's wrist, are shown in the exploded view of FIG. 27.

The connector band 300 is shown in detail in FIGS. 22-24, and may be made of a flexible material, including, but not limited to a thermoplastic elastomer. The connector band may also be made out of an elastomer fabric, which may be able to stretch. The connector band 300 may be further configured, as seen in FIGS. 23-24, to electrically couple the second treatment module to the first treatment module, in which case the TPE may be over-molded over the electrical cables/wiring. First and second rigid plastic interfaces 310/320 may be formed on the first and second ends of the connector band 300, and may be used to respectively couple the band to the housing 130 of the first treatment module, and to the housing 230 of the second treatment module 200. The connector band 300 may be formed in different lengths, as shown in FIG. 23A. Where the second treatment module 200 may have its own dedicated power source and controls, the connector band 300 may be formed for adjusting a length of the band, to accommodate different size wrists for different size users, and may be formed similar to the strap and adjustment clip of U.S. Pat. No. 3,166,761 to Strohm.

The attachment band 400 is shown in detail in FIGS. 16-18, and may be made of a flexible material, including, but not limited to a silicone thermoplastic elastomer. The attachment band may also be made out of an elastomer fabric. The end of the attachment band 400 may have a rigid plastic interface 410 formed thereon and usable to fixedly secure the band to the housing 130 of the first treatment module 100. The attachment band 400 may be molded with eyelets 420 for corresponding attachment to mounting studs 430 that may be secured to the second treatment module 200. As shown in FIG. 17A, the attachment band 400 may be formed in different lengths.

The first treatment module 100 of bracelet 10 may also broadly include an LCD screen, which may be a touch screen, and a microprocessor that may be coupled to the LCD screen, the cooling unit, and to the light sources. Firmware and/or software implemented therein may cause the display of one or more graphical user interface (GUI) screens on the LCD. Exemplary GUI screens are shown in FIGS. 51-61. The screens may permit at least selection by the user of one or more preprogrammed treatment protocols, and/or a customized treatment option, where the customized treatment may permit selection of a treatment time, a cooling temperature, and a light intensity for each of the wavelengths.

Additionally, or alternatively, a smart phone application may be used for remote controlling of each of the parameters that may otherwise be controlled by switches or the firmware controlled by the LCD screen that are physically located on the device itself.

In yet another embodiment, an IR pulse sensor may leverage use of a microprocessor. The IR pulse sensor and other sensors may derive pulse wave characteristics, for example, parameters such as Heart Rate (HR) and Heart Rate Variability (HRV).

In addition, the device may have an accessory port that that may be a charging USB port that can also provide a digital signal and can power via USB protocol, or other light or cooling accessories. For example, it could power an intranasal or intra-auricular LED probe. These accessories may be controlled by a smart phone application or may otherwise be controlled by switches or the firmware controlled by the LCD screen that are physically located on the device itself.

The device may also utilize two temperature sensors in the thermal module. One temperature sensor may be internal and may monitor the temperature of the TEC from a safety standpoint, and may provide feedback to the user via the app (i.e., may serve as a watchdog to ensure the TEC doesn't go out of the expected operating temperature range). The other sensor may be remotely mounted to touch the user's skin to monitor the skin temperature. It may be thermally isolated from the TEC and the thermally conductive material such that the only thermal influence will be the skin (i.e., plastic mounting features may be used). Both of the temperature readings may be reported back to, and monitored by, the user in near-real-time, if they are using the app (i.e., as fast as Bluetooth can transmit and process essentially).

Tests of a prototype were conducted, to test a used for work volume capacity and strength gains, directly. In a warm environment, the test used lower-body large muscle exercises to raise core-body temperature and then tested the work capacity of upper-body large muscles. The independent variable was simultaneous wrist LLLT irradiation and arterio-venous blood cooling. The duration and total workload of lower body exercise was held constant. When work volume capacity gains increase, conditioning gains could also be expected. Frequent physical conditioning commonly leads to plateaus where minimal improvements in strength or work volume can be achieved over time.

During testing of the device, the subject demonstrated a 112% increase in pull-down capacity and a 43% increase in work volume. Strength gains were also measured by increases in the weight that could be bench-pressed only once in the fourth set of a pyramidal workout routine. An increase of over 11% in fourth set weight increases were observed in addition to a 33% increase in bench press work volume, leading to the conclusion that material performance gains were achieved from the use of a wrist-worn, portable device that interfaces only transcutaneously with arterial blood flow. An ARX machine was used to measure gains on both capacity and strength on both upper body exercises.

Figure 73:
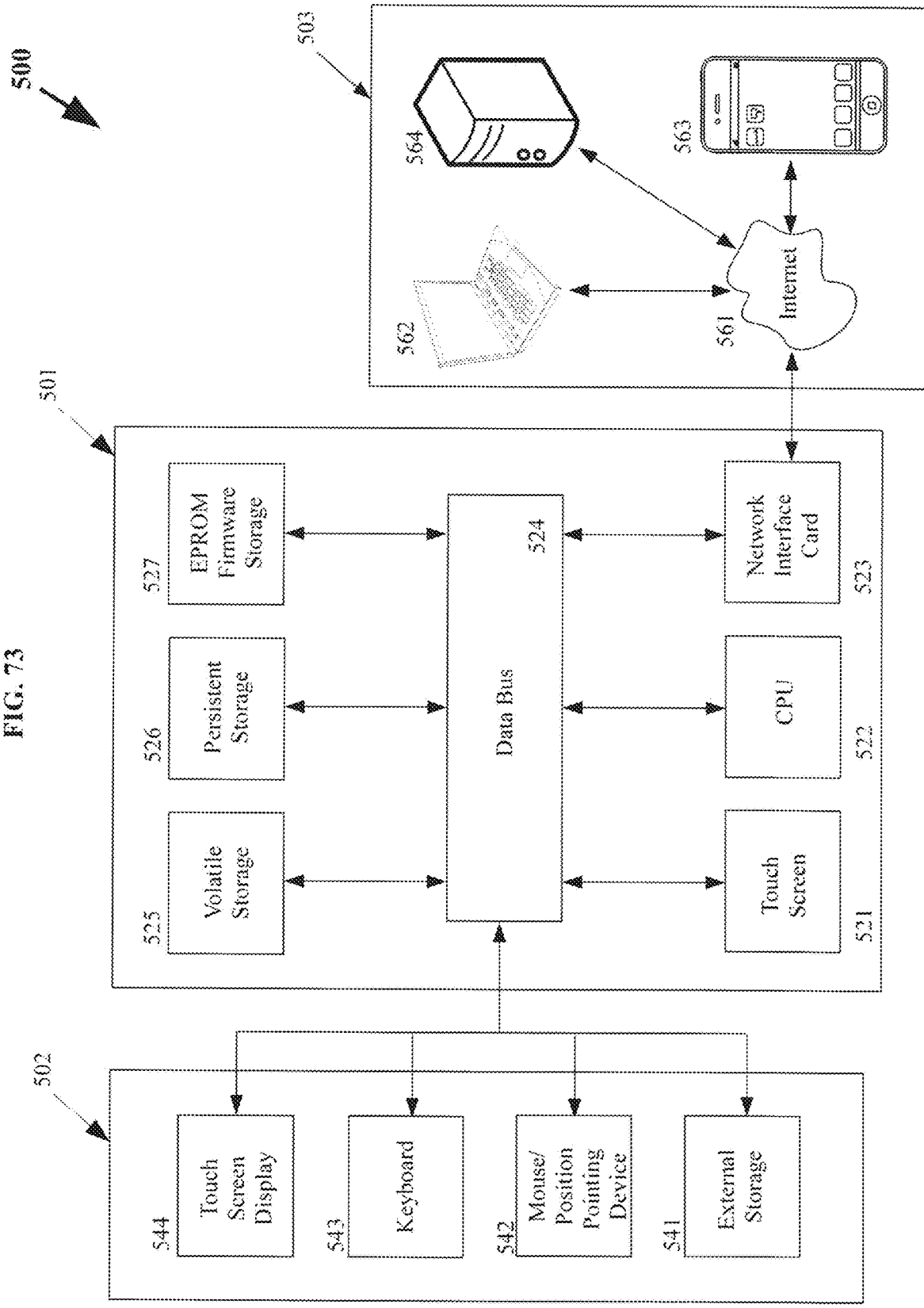
FIG. 73 is a schematic illustration showing an exemplary computing unit capable of being programmed by the instructions of the software of the present invention, and which may include personal computers, cellular phones, and other mobile devices.

Software of the present invention may run on a suitable computing device, such as a server, a tablet, a cell phone, or other mobile smart device, so a description of such an exemplary computer system is hereinafter disclosed, even though a particular embodiment may not require any or all of the described components. Exemplary computer system 500 (i.e., a client device associated with a particular user) is shown schematically in FIG. 73, and which may comprise computing unit 501 interacting with external peripherals 502, such as a separate touch screen display 544, and interacting with network resources 503, including use of the internet 561, and other computers (or other client devices or a server), which may be a laptop computer 562 (i.e., a second client device associated with a second user), a smart phone 563 (i.e., a third client device associated with a third user), a server 564, etc.

The computing unit 501 may include a data bus 524 for communicating information across and among various parts of computing unit 501, and a central processing unit, which may be a microprocessor (hereinafter "processor" or "CPU") 522 coupled with a bus 524 for processing information and performing other computational and control tasks. Computing unit 501 may also include a volatile storage 525, such as a random access memory (RAM) or other dynamic storage device, coupled to bus 524 for storing various information as well as instructions to be executed by processor 522. The volatile storage 525 may also be used for storing temporary variables or other intermediate information during execution of instructions by processor 522. Computing unit 501 may further include a read only memory (ROM) or an erasable programmable memory (EPROM) 527 or other static storage device coupled to bus 524 for storing static information and instructions for processor 522, such as basic input-output system (BIOS), as well as various system configuration parameters. A persistent storage device or non-volatile memory 526, such as a magnetic disk, optical disk, or solid-state flash memory device may be provided and may be coupled to bus 524 for storing information and instructions.

Computing unit 501 may be coupled via bus 524 to an integral display 521, possibly a touch-screen display, for use in displaying information to a user and for interacting therewith. If desired, computing unit 501 may be coupled via bus 524 to an external display screen 544. An external input device 543 (e.g., a standard keyboard) may be coupled to bus 524 for communicating information and command selections to processor 522. A cursor control device 542, such as a mouse, a trackball, or cursor direction keys, may be used for communicating direction information and command selections to processor 522 and for controlling cursor movement on display 544. An external storage device 541 may be connected to the computing unit 501 via bus 524 to provide an extra or removable storage capacity for the computing unit 501, which may be used to facilitate exchange of data with other computer systems.

Some of the techniques herein may be performed by computing unit 501 in response to processor 522 executing one or more sequences of one or more instructions contained in the volatile memory 525. Execution of the sequences of instructions contained in a non-transitory memory may cause processor 522 to perform the process steps described herein. In alternative embodiments, specific hard-wired digital circuitry may be used in place of, or in combination with, software instructions to implement the invention.

The term "computer-readable medium" as used herein refers to any medium that participates in providing instructions to processor 522 for execution. The computer-readable medium is just one example of a machine-readable medium, which may carry instructions for implementing any of the methods and/or techniques described herein. Various forms of computer readable media may contain one or more sequences of one or more instructions for the processor 522 to execute, including non-volatile media (storage device 526), and volatile media (storage device 525). Common forms of computer-readable media include, for example, a floppy disk, a hard disk, magnetic tape, or any other magnetic medium, a CD-ROM, a flash drive, and a memory card.

The computing unit 501 may thus also include a communication interface, such as network interface card 523 coupled to the data bus 522. Communication interface 523 may provide a two-way data communication coupling to a network link that may be connected to a local network. For example, communication interface 523 may be an integrated services digital network (ISDN) card or a modem to provide a data communication connection to a corresponding type of telephone line, or it may be a local area network interface card (LAN NIC) to provide a data communication connection to a compatible LAN.

Network link 523 also typically provides data communication to other network resources. For example, the network link may provide a connection over the internet 561 to the world-wide-web. Thus, the computing unit 501 can access resources located anywhere using the Internet 561. Also, the computing unit 501 may also be accessed by, or communicate with, other computers (e.g. 562), or another smart device (e.g., smartphone 563), generally with permission, and which may be located anywhere with access to the internet 561.

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A bracelet comprising:
   a first treatment module comprising a plurality of light sources configured to emit a plurality of selective wavelengths of light away from a first side of said first treatment module to provide therapeutic blood irradiation;
   a second treatment module comprising a thermoelectric cooling (TEC) unit positioned therein to transfer heat away from a first side of said second treatment module towards a second side of said second treatment module; and a microcontroller to budget an amount of power supplied to said TEC unit to control cooling provided by said thermoelectric cooling unit;
   a band that couples said first treatment module to said second treatment module and is configured to releasably secure said first treatment module and said second treatment module to a dorsal side of the user's wrist and a ventral side of a user's wrist, respectively;
   wherein said plurality of light sources are positioned in at least a first row and a second row in said first treatment module, with said first and second rows oriented to substantially overlie vasculature on the dorsal side of the user's wrist; and
   wherein said second treatment module comprises: a housing; a heat sink and a plurality of fins configured to transfer heat away from said TEC unit toward said second side of said second treatment module; a plate formed of a thermally conductivity material being positioned on at least a portion of said first side of said second treatment module in proximity to a cold side of said TEC unit to transmit heat away from the user's wrist towards the cold side of said TEC unit; a thermally insulating gasket positioned around the sides of said TEC unit to prevent leakage of heat around the sides of said TEC unit; and a thermally insulating cushion positioned on at least a portion of said first side of said second treatment module to prevent heat transfer with respect to surrounding air.

2. The bracelet according to claim 1 further comprising a battery configured to power at least said first treatment module.

3. The bracelet according to claim 2 wherein said battery is a lithium polymer battery configured to provide up to about 2000 mAh at 7.4 V.

4. The bracelet according to claim 2 wherein said battery is configured to provide power for at least one hour of said therapeutic blood irradiation and said cooling.

5. The bracelet according to claim 1 wherein said plurality of light sources of said first treatment module comprises a first plurality of light sources configured to emit a first wavelength of light, a second plurality of light sources configured to emit a second wavelength of light, and a third plurality of light sources configured to emit a third wavelength of light.

6. The bracelet according to claim 5 wherein said first plurality of light sources and said third plurality of light sources are each configured to emit an infrared wavelength of light.

7. The bracelet according to claim 6 wherein said second plurality of light sources are each configured to emit a mixture of red, blue, and green wavelengths of light.

8. The bracelet according to claim 7 further comprising:
an LCD screen; and
firmware configured to display a graphic user interface (GUI) on said LCD screen, to permit selection from one or more preprogrammed treatment protocols and a customized treatment option, wherein said customized treatment option provides for selection of a treatment time, and a cooling temperature.

9. A bracelet comprising:
a first treatment module comprising a plurality of light sources configured to emit a plurality of selective wavelengths of light away from a first side of said first treatment module to provide therapeutic blood irradiation;
a second treatment module comprising a thermoelectric cooling (TEC) unit positioned therein to transfer heat away from a first side of said second treatment module towards a second side of said second treatment module; and a microcontroller to budget an amount of power supplied to said TEC unit to control cooling provided by said thermoelectric cooling unit;
a band that couples said first treatment module to said second treatment module and is configured to releasably secure said first treatment module and said second treatment module to a dorsal side of the user's wrist and a ventral side of a user's wrist, respectively;
wherein said plurality of light sources are positioned in at least a first row and a second row in said first treatment module, with said first and second rows oriented to substantially overlie vasculature on the dorsal side of the user's wrist; and
wherein said second treatment module comprises: a housing with a plurality of openings; a heat sink comprising a plurality of fins configured to transfer heat away from said TEC unit toward said openings in said housing; a thermally insulating material positioned around the sides of said TEC unit to prevent leakage of heat around the sides of said TEC unit, and a thermally insulating cushion positioned on at least a portion of said first side of said second treatment module.

10. The bracelet according to claim 9 wherein said second treatment module comprises a plate formed of a thermally conductivity material, said plate positioned on at least a portion of said first side of said second treatment module in proximity to a cold side of said TEC unit to transmit heat away from the user's wrist towards the cold side of said TEC unit.

11. The bracelet according to claim 9 further comprising a battery configured to power said first and second treatment modules.

12. The bracelet according to claim 11 wherein said battery is a lithium polymer battery configured to provide up to 2000 mAh at 7.4 V.

13. The bracelet according to claim 11 wherein said battery is configured to provide power for at least one hour of said therapeutic blood irradiation and said cooling.

14. The bracelet according to claim 9 wherein said plurality of light sources of said first treatment module comprises a first plurality of light sources configured to emit a first wavelength of light, a second plurality of light sources configured to emit a second wavelength of light, and a third plurality of light sources configured to emit a third wavelength of light.

15. The bracelet according to claim 14 wherein said first plurality of light sources and said third plurality of light sources are each configured to emit an infrared wavelength of light.

16. The bracelet according to claim 15 wherein said second plurality of light sources are each configured to emit a mixture of red, blue, and green wavelengths of light.

17. The bracelet according to claim 9 further comprising:
an LCD screen; and
firmware configured to display a graphic user interface (GUI) on said LCD screen, to permit selection from one or more preprogrammed treatment protocols and a customized treatment option, wherein said customized treatment option provides for selection of a treatment time, and a cooling temperature.

18. The bracelet according to claim 2 wherein said battery is configured to provide power for at least one hour of said therapeutic blood irradiation and said cooling.

* * * * *